(12) United States Patent
Joel et al.

(10) Patent No.: US 7,683,185 B2
(45) Date of Patent: Mar. 23, 2010

(54) HISTONE DEACETYLASE INHIBITORS

(75) Inventors: Simon Joel, London (GB); Charles Marson, London (GB); Pascal Savy, London (GB)

(73) Assignee: Queen Mary & Westfield College, London (GB)

( * ) Notice: Subject to any disclaimer, the term of this patent is extended or adjusted under 35 U.S.C. 154(b) by 339 days.

(21) Appl. No.: 10/535,280

(22) PCT Filed: Nov. 18, 2003

(86) PCT No.: PCT/GB03/05035

§ 371 (c)(1), (2), (4) Date: Jun. 20, 2006

(87) PCT Pub. No.: WO2004/046094

PCT Pub. Date: Jun. 3, 2004

(65) Prior Publication Data
US 2006/0235231 A1 Oct. 19, 2006

(30) Foreign Application Priority Data
Nov. 18, 2002 (GB) ................ 0226855.5

(51) Int. Cl.
C07D 333/56 (2006.01)
C07D 333/72 (2006.01)
C07D 409/02 (2006.01)

(52) U.S. Cl. ............... 549/58; 560/11; 560/12; 562/426; 562/621; 514/575

(58) Field of Classification Search .......... None
See application file for complete search history.

(56) References Cited

U.S. PATENT DOCUMENTS 4,013,776 A * 3/1977 Lafon ............... 514/575
2002/0103192 A1 8/2002 Curtin et al.

FOREIGN PATENT DOCUMENTS

GB 1519147 7/1978

(Continued)

OTHER PUBLICATIONS

G.X. Ma, et al., Synthetic Communications, 1997, 27(14), 2445-2453.*

(Continued)

Primary Examiner—Deborah D Carr
(74) Attorney, Agent, or Firm—Pepper Hamilton LLP

(57) ABSTRACT

The present invention provides histone deacetylase inhibitors of general formula (I), process for the preparation of such compounds and uses of the compounds in medicine.

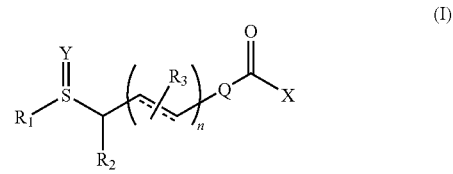

(I)

32 Claims, 11 Drawing Sheets

FOREIGN PATENT DOCUMENTS

| | | | |
|---|---|---|---|
| GB | 2 101 600 | * | 1/1983 |
| GB | 2101600 | | 1/1983 |
| GB | 2101600 A | | 1/1983 |
| JP | 43-012331 | | 5/1968 |
| JP | 51-125228 | | 11/1976 |
| JP | 58-018334 A1 | | 2/1983 |
| WO | WO 01/38322 | | 5/2001 |
| WO | WO 01/42437 | | 6/2001 |
| WO | WO 01/67107 | | 9/2001 |
| WO | WO 01/70675 | | 9/2001 |
| WO | WO 02/07722 | | 1/2002 |
| WO | WO 02/08273 | | 1/2002 |
| WO | WO 02/15921 | | 2/2002 |
| WO | WO 02/30970 | | 4/2002 |
| WO | WO 02/36783 | | 5/2002 |
| WO | WO 02/46129 | | 6/2002 |
| WO | WO 02/50244 | | 6/2002 |
| WO | WO 02/50285 | | 6/2002 |
| WO | WO 02/055688 | | 7/2002 |
| WO | WO 02/060430 | | 8/2002 |
| WO | WO 02/062773 | | 8/2002 |
| WO | WO 02/069947 | | 9/2002 |
| WO | WO 02/076941 | | 10/2002 |

OTHER PUBLICATIONS

Q.B. Cass, et al., Journal of the Chemical Society, Perkin Transactions 1, 1991, (11), 2683-2686.*
T.A. Gourdie, et al., Journal of Medicinal Chemistry, 1990, 33(4), 1177-1186.*
I. Flemming, et al., Tetrahedron Letters, 1979, (34), 3205-3208.*
G. Cai, et al., Journal of the American Chemical Society, 1993, 115(16), 7192-7198.*
A.G.M. Barrett, et al., Journal of Organic Chemistry, 1986, 51(25), 4840-4856.*
R.A. Bunce, et al., Journal of Organic Chemistry, 1993, 58(25), 7143-7148.*
A.S. Kalgutkar, et al., Journal of Medicinal Chemistry, 1998, 41(24), 4800-4818.*
M. Cowart, et al., Journal of Medicinal Chemistry, 1998, 41(14), 2636-2642.*
G. Dannhardt, et al., Die Pharmazie, 1997, 52(6), 428-436.*
Marks et al., "Histone deacetylase inhibitors: inducers of differentiation or apoptosis of transformed cells," *Journal of the National Cancer Institute* (2000) 92(15):1210-1216.
Marks et al., "Histone deacetylases and cancer: causes and therapies," *Nat Rev Cancer* (2001) 1(3):194-202.
Ma et al., "The synthesis of diencarbamates as adept prodrug models," *Synthetic Communications* (1997) 24(14):2445-2454.

Cass et al., "On the preparation and rearrangement of some vinylic sulphoxides," *Journal of the Chemical Society* (1991) No. 11, pp. 2683-2686.
Gourdie et al., "DNA-directed alkylating agents. 1. Structure-activity relationships for acridine-linked aniline mustards: consequences of varying the reactivity of the mustard," *Journal of Medicinal Chemistry* (1990) 33(4):1177-1186.
Flemming et al., "gamma-Sulphenylation of α,β-unsaturated aldehydes, ketones, and esters: the use of 0-silylated dienolates," *Tetrahedron Letters* (1979) No. 34, pp. 3205-3208.
Cai et al., "CD exiton chirality method. New red-shifted chromophores for hydroxyl groups," *Journal of the American Chemical Society* (1993) 115(16):7192-7198.
Barrett et al., "Total synthesis of (+)-milbemycin β3," *Journal of Organic Chemistry* (1986) 51(25):4840-4856.
Bunce et al., "Functionalised carbocycles by tandem dealkoxcarbonylation-Michael addition reactions," *Journal of Organic Chemistry* (1993) 58(25):7143-7148.
Database Accession No. 1969:37237 Caplus Abstract.
Kalgutkar et al., "Covalent modification of cyclooxygenase-2 (COX-2) by 2-acetoxyphenyl alkyl sulfides, a new class of selective COX-2 inactivators," *Journal of Medicinal Chemistry* (1998) 41(24):4800-4818.
Cowart et al., "Nitroaromatic amino acids as inhibitors of neuronal nitric oxide synthase," *Journal of Medicinal Chemistry* (1998) 41(14):2636-2642.
Dannhardt et al., "[2-Aryl-pyrrolo[2,1-b]benzothiazoles as a selective or dual inhibitors of cyclo-oxygenases and 5-lipoxygenases. 21. Non-steroidal anti-inflammatory agents]," *Die Pharmazie* (1997) 52(6):428-436. (German).
Yoshida et al., "Potent and specific inhibition of mammalian histone deacetylase both in vivo and in vitro by trichostatin A.," *Journal of Biological Chemistry* (1990) 265(28):17174-17179.
Fleming, I., et al., Tetrahedron Letters, 1979;20(34):3205-3208.
Cai, G., et al., Journal of the American Chemical Society, 1993I115(16):7192-7198.
Bunce, R. E., et al, Journal of Organic Chemistry, 1993;58(25):7143-7148.
Barrett, A. G. M., et al., Journal of Organic Chemistry, 1986;51(25) 4840-4853.
Kalgutkar, A. S., et al., Journal of Medical Chemistry, 1998;41(24):4800-4818.
Cowart, M., et al., Journal of Medicinal Chemistry, 1998;41(14):2636-2642.
Gourdie, T. A., et al., Journal of Medicinal Chemistry, 1990;33(4):1177-1186.
Ma, G. X., et al, Synthetic Communications, 1997;27(14):2445-2453.
Cass, Q. B., et al., Journal of the Chemical Society, Perkin Transactions 1, 1991;11:2683-2686.

* cited by examiner

| | R² | R³ | R | n |
|---|---|---|---|---|
| 26a | H | H | Me | 1 |

| | R² | R³ | R | n |
|---|---|---|---|---|
| 27a | H | H | Me | 1 |
| 27b | H | H | Et | 2 |

| | R¹³ | R² | R³ | R | n |
|---|---|---|---|---|---|
| 28a | H | H | H | H | 0 |
| 28b | Cl | H | H | Me | 1 |
| 28c | Cl | H | H | Et | 2 |
| 28d | NH₂ | H | H | Me | 1 |
| 28e | NMe₂ | H | H | Me | 1 |
| 28f | NMeR⁴ | H | H | Me | 1 |
| 28g | NHR⁵ | H | H | Me | 1 |
| 28h | Br | H | H | Me | 1 |
| 28i | Ar | H | H | Me | 1 |

28f, 30f, 31f: R⁴ = p-ClC₆H₄CH₂
28g, 29g: R⁵ = p-ClC₆H₄SO₂
28i, 29i: Ar = p-ClC₆H₄

| | R¹³ | R² | R³ | R | n |
|---|---|---|---|---|---|
| 29a | H | H | H | H | 0 |
| 29b | Cl | H | H | H | 1 |
| 29c | NMe₂ | H | H | H | 1 |
| 28g | NHR⁵ | H | H | H | 1 |
| 29i | Ar | H | H | H | 1 |

| | R¹³ | R² | R³ | R | n |
|---|---|---|---|---|---|
| 30a | H | H | H | Me | 0 |
| 30b | Cl | H | H | Me | 1 |
| 30c | Cl | H | H | Et | 2 |
| 30d | H | H | H | H | 0 |
| 30e | NMe₂ | H | H | Me | 1 |
| 30f | NMeR⁴ | H | H | Me | 1 |
| 30i | Ar | H | H | Me | 1 |

| | R¹³ | R² | R³ | n |
|---|---|---|---|---|
| 31a | Cl | H | H | 1 |
| 31b | OMe | H | H | 0 |
| 31c | Cl | H | H | 2 |
| 31e | NMe₂ | H | H | 1 |
| 31f | NMeR⁴ | H | H | 1 |
| 31i | Ar | H | H | 1 |

| | R¹³ | R² | R³ | R |
|---|---|---|---|---|
| 32a | H | H | H | H |
| 32b | H | H | H | Me |

| | R¹³ | R² | R³ |
|---|---|---|---|
| 33a | H | H | H |

FIG. 3 CONT'D

Scheme 5

HISTONE DEACETYLASE INHIBITORS

CROSS-REFERENCE TO RELATED APPLICATIONS

This application is the U.S. National Stage filing of International Application Serial No. PCT/GB2003/005035 filed Nov. 18, 2003, which claims priority to GB 0226855.5 filed Nov. 18, 2002, each of which is incorporated herein by reference in its entirety.

FIELD OF THE INVENTION

The present invention relates to histone deacetylase inhibitors, methods for the synthesis of such compounds, use of the compounds in medicine.

BACKGROUND OF THE INVENTION

A number of recent research reports suggest that chromosome translocations in cancer cells disrupt proteins involved in the process of histone acetylation and de-acetylation, and that these abnormal proteins cause aberrant gene repression. Histones are the protein component of chromatin, which comprises DNA supported by histone octamers to form nucleosomes. These histone proteins have lysine rich tails which when deacetylated become charged and attracted to the DNA backbone. This condenses the chromatin structure such that proteins involved in gene transcription cannot gain access, resulting in transcriptional repression.

It has been proposed that inhibition of histone deacetylase (HDAC) enzymes could relieve such gene repression and reinstate the program of differentiation and apoptosis in a manner analogous to the use of retinoic acid in the treatment of acute promyelocytic leukemia—a form of "transcription therapy" A number of compounds that inhibit HDAC have been described, and several are in phase I and II clinical trials. These compounds have been shown to induce cell cycle arrest, differentiation and cell death in cancer cells growing in vitro and in animal xenograft models. The most potent HDAC inhibitor, Trichostatin A (TSA) was isolated from *Streptomyces hygroscopicus* in the 1970's, as an antifungal antibiotic against *trichophyton*. Although potent in vitro, TSA has limited stability and is therefore not therapeutically useful. Novel compounds with a similar structure, such as suberoylanilide hydroxamate (SAHA), have activity in pre-clinical models, and have shown some anti-cancer activity in phase I studies. However, this compound is also rapidly eliminated, requiring large doses for activity. Other HDAC inhibitors that have been tested in the phase I setting have major side effects (i.e. Depsipeptide), or affect histone acetylation by an indirect mechanism (CI-994). Others are still undergoing early clinical investigation.

Potent, metabolically stable, HDAC inhibitors would be more therapeutically useful than many of those currently in clinical trials.

SUMMARY OF THE INVENTION

A new class of compounds that are inhibitors of HDAC has now been prepared which are believed to be more metabolically stable and more robust to in vivo enzyme attack, in which the compounds are characterised by the presence of an isostere $S(=O)_n$ (in place of $C=O$ in trichostatin (TSA)).

According to a first aspect of the invention, there is provided a compound of general formula (I):

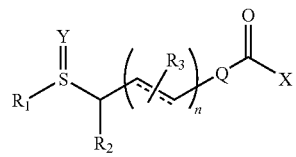

in which:

$R^1$ may be ($C_6$ or $C_{10}$) aryl, ($C_6$ or $C_{10}$) arylalkyl, ($C_6$ or $C_{10}$) heteroaryl, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl or a combination thereof to form a linked or fused ring system, the cyclic moiety being optionally substituted with ($C_1$-$C_{10}$) alkyl, ($C_1$-$C_{10}$) alkenyl, ($C_1$-$C_{10}$) alkynyl, ($C_1$-$C_{10}$) alkoxy, ($C_1$-$C_{10}$) thioalkoxy, hydroxyl, hydroxyl, ($C_1$-$C_{10}$) hydroxylalkyl, halo, ($C_1$-$C_{10}$) haloalkyl, amino, amido, ($C_1$-$C_{10}$) alkylamino, ($C_1$-$C_{10}$) alkylcarbonyloxy, ($C_1$-$C_{10}$) alkoxycarbonyl, ($C_1$-$C_{10}$) alkylcarbonyl, ($C_1$-$C_{10}$) alkylthiocarbonyl, ($C_1$-$C_{10}$) alkylsulfonylamino, aminosulfonyl, ($C_1$-$C_{10}$) alkylsulfinyl, or ($C_1$-$C_{10}$) alkylsulfonyl, $R^2$ and $R^3$ may each independently be hydrogen, ($C_1$-$C_{12}$) alkyl, substituted ($C_1$-$C_{12}$) alkyl, or unsaturated ($C_1$-$C_{12}$) comprising one or more $C=C$ bond or $C\equiv C$ bond, ($C_6$ or $C_{10}$) aryl or ($C_6$ or $C_{10}$) heteroaryl, or a combination thereof to form a linked or fused ring system, or ($C_1$-$C_{10}$) alkyl, ($C_1$-$C_{10}$) alkenyl, ($C_1$-$C_{10}$) alkynyl, ($C_1$-$C_{10}$) alkoxy, ($C_1$-$C_{10}$) thioalkoxy, hydroxyl, hydroxyl, ($C_1$-$C_{10}$) hydroxylalkyl, halo, ($C_1$-$C_{10}$) haloalkyl, cyano, nitro, amino, amido, ($C_1$-$C_{10}$) alkylamino, ($C_1$-$C_{10}$) alkylcarbonyloxy, ($C_1$-$C_{10}$) alkoxycarbonyl, ($C_1$-$C_{10}$) alkylcarbonyl, ($C_1$-$C_{10}$) alkylthiocarbonyl, ($C_1$-$C_{10}$) alkylsulfonylamino, aminosulfonyl, ($C_1$-$C_{10}$) alkylsulfinyl, or ($C_1$-$C_{10}$) alkylsulfonyl, in which the saturated or an unsaturated hydrocarbon chain is optionally interrupted by O, S, NR, CO, C(NR), N(R)SO$_2$, SO$_2$N(R), N(R)C(O)O, OC(O)N(R), N(R)C(O)N(R), OC(O), C(O)O, OSO$_2$, SO$_2$O, or OC(O)O, where R may be independently hydrogen, ($C_1$-$C_{10}$) alkyl, ($C_1$-$C_{10}$) alkenyl, ($C_1$-$C_{10}$) alkynyl, ($C_1$-$C_{10}$) alkoxy, ($C_1$-$C_{10}$) hydroxylalkyl, hydroxyl, ($C_1$-$C_{10}$) halolalkyl, where each of the saturated or unsaturated hydrocarbon chains may be optionally substituted with ($C_1$-$C_{10}$) alkyl, ($C_1$-$C_{10}$) alkenyl, ($C_1$-$C_{10}$) alkynyl, ($C_1$-$C_{10}$) alkoxy, hydroxyl, hydroxyl, ($C_1$-$C_{10}$) hydroxylalkyl, halo, ($C_1$-$C_{10}$) haloalkyl, amino, ($C_1$-$C_{10}$) alkylcarbonyloxy, ($C_1$-$C_{10}$) alkoxycarbonyl, ($C_1$-$C_{10}$) alkylcarbonyl, ($C_1$-$C_{10}$) alkylsulfonylamino, aminosulfonyl, or ($C_1$-$C_{10}$) alkylsulfonyl, or $R^2$ and $R^3$ optionally form a ($C_6$ or $C_{10}$) aryl, ($C_6$ or $C_{10}$) arylalkyl, ($C_6$ or $C_{10}$) heteroaryl ring which may be a 5, 6 or 7-membered carbon ring containing one or more heteroatoms, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl linked ring system, optionally containing up to 3 heteroatoms, e.g. oxygen, nitrogen, sulphur or phosphorous, in which further rings as defined herein may be fused to the ring so formed.

or $R^1$ and $R^2$ optionally form a ($C_6$ or $C_{10}$) aryl, ($C_6$ or $C_{10}$) arylalkyl, ($C_6$ or $C_{10}$) heteroaryl ring which may be a 5, 6 or 7-membered carbon ring containing one or more heteroatoms, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl linked ring system, optionally the ring formed may be further substituted with a group $R^1$ as defined above, or the ring formed may be fused to a further $C_6$ aryl group which may be optionally substituted with a group $R^1$ as defined above, or a group $R^1R^2N$, with $R^1$ and $R^2$ as defined above, in which further rings as defined herein may be fused to the ring so formed, n may be equal to 0, 1 or 2, X may be hydroxyl (—OH), —OR, NHR, hydroxamate (—NHOH), NHOR, NROR, NRNHR, or SR where each group R may independently be hydrogen, $C_1$-$C_6$ alkyl or substituted $C_1$-$C_6$ alkyl, and Y may be 0, 1 or 2 oxygen atoms, or NR where R may be H, OH, OR or a carbon atom, where R maybe $C_1$-$C_6$ alkyl or substituted $C_1$-$C_6$ alkyl.

Q represents

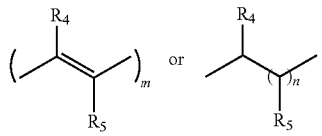

wherein m is an integer from 1 to 4; n is an integer from 1 to 8; and $R^4$ and $R^5$ each independently represents hydrogen, unsubstituted or substituted $C_1$-$C_{10}$ alkyl, an unsaturated hydrocarbon chain of up to ten carbon atoms comprising one or more carbon-carbon double bonds, $C_6$ or $C_{10}$ aryl, a 5- to 10-membered heterocyclic group, $C_1$-$C_{10}$ alkoxy, $C_1$-$C_{10}$ thioalkoxy, hydroxyl, halo, cyano, nitro, amino, amido, ($C_1$-$C_{10}$ alkyl)carbonyloxy, ($C_1$-$C_{10}$ alkoxy)carbonyl, ($C_1$-$C_{10}$ alkyl)carbonyl, ($C_1$-$C_{10}$ alkyl)thiocarbonyl, ($C_1$-$C_{10}$ alkyl)suflonylamino, aminosulfonyl, $C_1$-$C_{10}$ alkylsulfinyl, $C_1$-$C_{10}$ alkylsulfonyl, or a saturated or unsaturated $C_3$-$C_{12}$ hydrocarbon chain interrupted by O, S, NR, CO, C(NR), N(R)SO$_2$, SO$_2$N(R), N(R)C(O)O, OC(O)N(R), N(R)C(O)N(R), OC(O), C(O)O, OSO$_2$, SO$_2$O or OC(O)O where R is as defined above and the saturated or unsaturated hydrocarbon chain is optionally substituted as defined above;

and pharmaceutically acceptable salts thereof.

The compounds of general formula (I) may also include a saturated linkage (with or without substituents, replacing CH=CH in structure (I) adjacent to the COX group. Additionally, the chain linkage (as a whole or in part) may be of any level of saturation, and may incorporate rings fused anywhere onto the chain linking the end group and the COX terminus.

It may be preferred for the definition of the compounds of general formula (I) to be where:

$R^1$ may be ($C_6$ or $C_{10}$) aryl, ($C_6$ or $C_{10}$) arylalkyl, ($C_6$ or $C_{10}$) heteroaryl, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl or a combination thereof to form a linked or fused ring system, the cyclic moiety being optionally substituted with ($C_1$-$C_6$) alkyl, ($C_1$-$C_6$) alkenyl, ($C_1$-$C_6$) alkoxy, ($C_1$-$C_6$) thioalkoxy, hydroxyl, ($C_1$-$C_6$) hydroxylalkyl, halo, ($C_1$-$C_6$) haloalkyl, amino, amido, ($C_1$-$C_6$) alkylamino, ($C_1$-$C_6$) alkylcarbonyloxy, ($C_1$-$C_6$) alkoxycarbonyl, ($C_1$-$C_6$) alkylcarbonyl, ($C_1$-$C_6$) alkylsulfonylamino, $R^2$ and $R^3$ may each independently be hydrogen, ($C_1$-$C_4$) alkyl, substituted ($C_1$-$C_4$) alkyl, or unsaturated ($C_1$-$C_4$) comprising one or more C=C bond or C≡C bond, ($C_6$ or $C_{10}$) aryl or ($C_6$ or $C_{10}$) heteroaryl, or a combination thereof to form a linked or fused ring system, or ($C_1$-$C_4$) alkyl, ($C_1$-$C_4$) alkenyl, ($C_1$-$C_4$) alkynyl, ($C_1$-$C_4$) alkoxy, hydroxyl, ($C_1$-$C_4$) hydroxylalkyl, halo, ($C_1$-$C_4$) haloalkyl, amino, amido, ($C_1$-$C_4$) alkylamino, ($C_1$-$C_4$) alkylcarbonyloxy, ($C_1$-$C_4$) alkoxycarbonyl, ($C_1$-$C_4$) alkylcarbonyl, ($C_1$-$C_4$) alkylsulfonylamino, in which the saturated or an unsaturated hydrocarbon chain is optionally interrupted by O, S, NR, CO, C(NR), N(R)SO$_2$, SO$_2$N(R), N(R)C(O)O, OC(O)N(R), N(R)C(O)N(R), OC(O), C(O)O, OSO$_2$, or SO$_2$O, where R may be independently hydrogen, ($C_1$-$C_4$) alkyl, ($C_1$-$C_4$) alkenyl, ($C_1$-$C_4$) alkynyl, ($C_1$-$C_4$) alkoxy, ($C_1$-$C_4$) hydroxylalkyl, hydroxyl, ($C_1$-$C_4$) halolalkyl, where each of the saturated or unsaturated hydrocarbon chains may be optionally substituted with ($C_1$-$C_4$) alkyl, ($C_1$-$C_4$) alkenyl, ($C_1$-$C_4$) alkynyl, ($C_1$-$C_4$) alkoxy, hydroxyl, ($C_1$-$C_4$) hydroxylalkyl, halo, ($C_1$-$C_4$) haloalkyl, amino, ($C_1$-$C_4$) alkylcarbonyloxy, ($C_1$-$C_4$) alkoxycarbonyl, ($C_1$-$C_4$) alkylcarbonyl, ($C_1$-$C_4$) alkylsulfonylamino, or $R^2$ and $R^3$ optionally form a ($C_6$ or $C_{10}$) aryl, ($C_6$ or $C_{10}$) arylalkyl, ($C_6$ or $C_{10}$) heteroaryl, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl linked or fused ring system, optionally containing up to 3 heteroatoms, e.g. oxygen, nitrogen, sulphur or phosphorous.

or $R^1$ and $R^2$ optionally form a ($C_6$ or $C_{10}$) aryl, ($C_6$ or $C_{10}$) arylalkyl, ($C_6$ or $C_{10}$) heteroaryl, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl linked or fused ring system, optionally the ring formed may be further substituted with a group $R^1$ as defined above, or the ring formed may be fused to a further $C_6$ aryl group which may be optionally substituted with a group $R^1$ as defined above, or a group $R^1R^2N$, with $R^1$ and $R^2$ as defined above, n may be equal to 0, 1 or 2, X may be hydroxyl (—OH), —OR, NHR, hydroxamate (—NHOH), NHOR, NROR, NRNHR, or SR where each group R may independently be hydrogen, $C_1$-$C_4$ alkyl or substituted $C_1$-$C_4$ alkyl, and Y may be 0, 1 or 2 oxygen atoms, or NR where R may be H, OH, OR or a carbon atom, where R may be $C_1$-$C_4$ alkyl or substituted $C_1$-$C_4$ alkyl.

Q represents

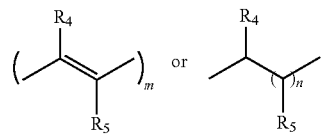

wherein m is an integer from 1 to 4; n is an integer from 1 to 8; and $R^4$ and $R^5$ each independently represents hydrogen, unsubstituted or substituted $C_1$-$C_4$ alkyl, an unsaturated hydrocarbon chain of up to ten carbon atoms comprising one or more carbon-carbon double bonds, $C_6$ or $C_{10}$ aryl, a 5- to 10-membered heterocyclic group, $C_1$-$C_4$ alkoxy, $C_1$-$C_4$ thioalkoxy, hydroxyl, halo, cyano, nitro, amino, amido, ($C_1$-$C_4$ alkyl)carbonyloxy, ($C_1$-$C_4$ alkoxy)carbonyl, ($C_1$-$C_4$ alkyl) carbonyl, ($C_1$-$C_4$ alkyl)thiocarbonyl, ($C_1$-$C_4$ alkyl)suflonylamino, aminosulfonyl, $C_1$-$C_4$ alkylsulfinyl, $C_1$-$C_4$ alkylsulfonyl, or a saturated or unsaturated $C_3$-$C_{12}$ hydrocarbon chain interrupted by O, S, NR, CO, C(NR), N(R)SO$_2$, SO$_2$N(R), N(R)C(O)O, OC(O)N(R), N(R)C(O)N(R), OC(O), C(O)O, OSO$_2$, SO$_2$O or OC(O)O where R is as defined above and the saturated or unsaturated hydrocarbon chain is optionally substituted as defined above.

In a further preferred embodiment, the substituent groups $C_1$-$C_6$ may be replaced by $C_1$-$C_4$, and the groups $C_1$-$C_4$ may be replaced by $C_1$-$C_3$, mutatis mutandis.

A preferred group of compounds within the general formula (I) have the formula (Ia)

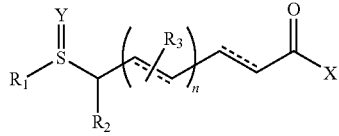
(Ia)

where $R^1$, $R^2$ and $R^3$ have the definitions given above. In a more preferred embodiment the compounds may be defined by formula (Ib)

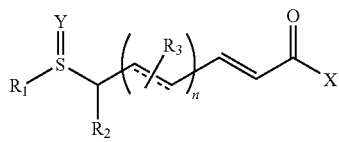
(Ib)

Further preferred groups of compounds within the scope of general formula (I) are (A), (B1), (B2) and (C), where $R^1$, $R^2$, $R^3$, $R^4$ and $R^5$ have the definitions given above and where each group R may independently be hydrogen, $C_1$-$C_6$ alkyl or substituted $C_1$-$C_6$ alkyl.

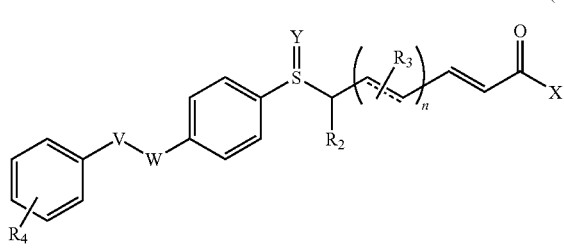
(A)

For type (A) with the scope of substituents and rings etc. as outlined for (I), in particular, V and W may constitute a single bond between the aromatic (or heterocyclic or alicyclic) rings, or they may take the form V=CR and W=N (such that a linkage RC=N is present), or the form V=N and W=CR (such that a linkage N=CR is present), or a saturated version of either of those linkages (with or without alkyl aryl, heterocyclic, or other substituents) or a linkage of the form VW or WV=RRC—O or RRC—S. Additionally, the chain linkage attached to COX may be of any level of saturation, and may incorporate rings fused onto the chain linking the end group and the COX terminus.

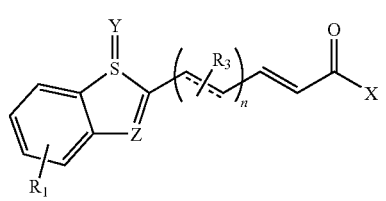
(B1)

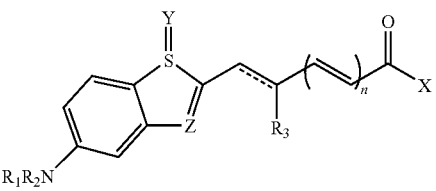
(B2)

For types (B1) and especially to types (B2) both with the scope of substituents and rings already as defined for I above, and n=zero, one or two. However, especially noteworthy for type (B2) are Y=no atom, O or $O_2$ or NR and Z=CR or N and n=zero, one or two and X=NHOH, OH, NROR, CRROH or derivatives or related groups for X, including any combination of the aforementioned groups and substituents for X, Y and Z. Additionally, the chain linkage may be of any level of saturation, and may incorporate rings fused onto the chain linking the end group and the COX terminus. For both (B1) and (B2), Z may be a one atom linkage of N, or C, in which case can be represented by —CH or —CR, or it may also be a two-atom linkage of varying combinations of atoms, in particular C, O, N, S, SO, $SO_2$ and forming part of a saturated, partly saturated, or unsaturated ring.

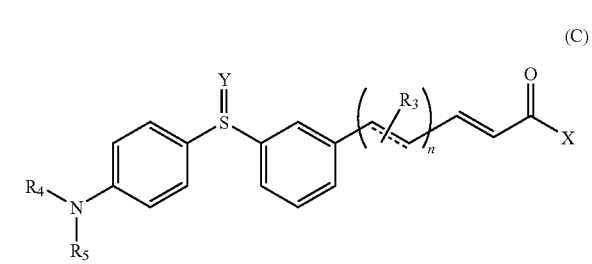
(C)

For type (C), in which Y=no atom, O or $O_2$ or NR and n=zero, one or two and X=NHOH, OH, NROR, CRROH or derivatives or related groups for X, including any combination of the aforementioned groups and substituents for X, Y and Z (although not herein covered by experimental details). Additionally, the chain linkage may be of any level of saturation, and may incorporate rings fused onto the chain linking the end group and the COX terminus.

BRIEF DESCRIPTION OF THE DRAWINGS

Reference in the present application is now made to a number of reaction schemes which are present for the purposes or illustration only and are not to be construed as being limiting on the present invention. Schemes 1, 2 3, 4 and 5 are shown in FIGS. 1 to 5.

DESCRIPTION OF EMBODIMENTS

Figure 1:
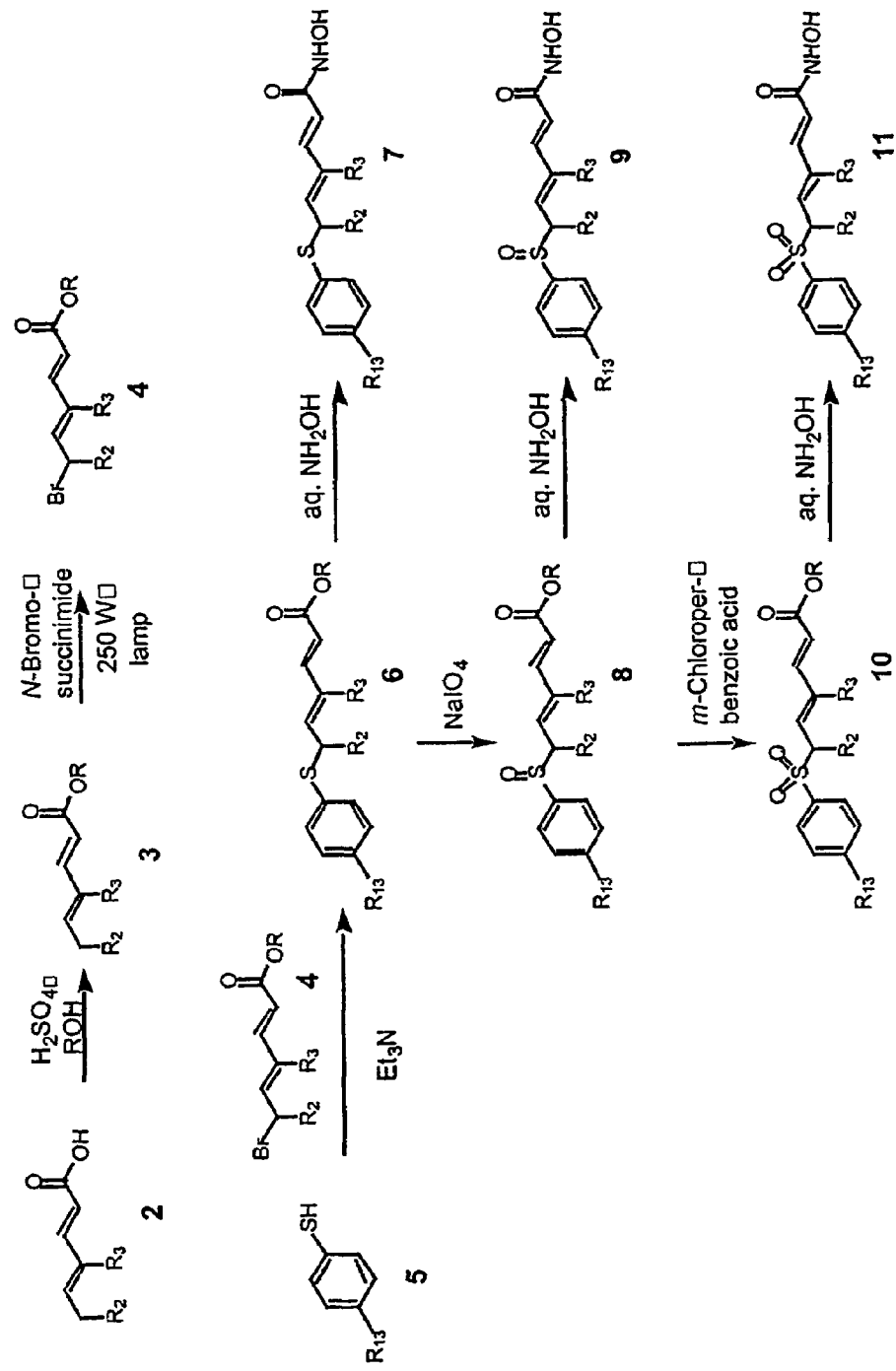
FIG. 1 shows reaction scheme 1.
Figure 1:
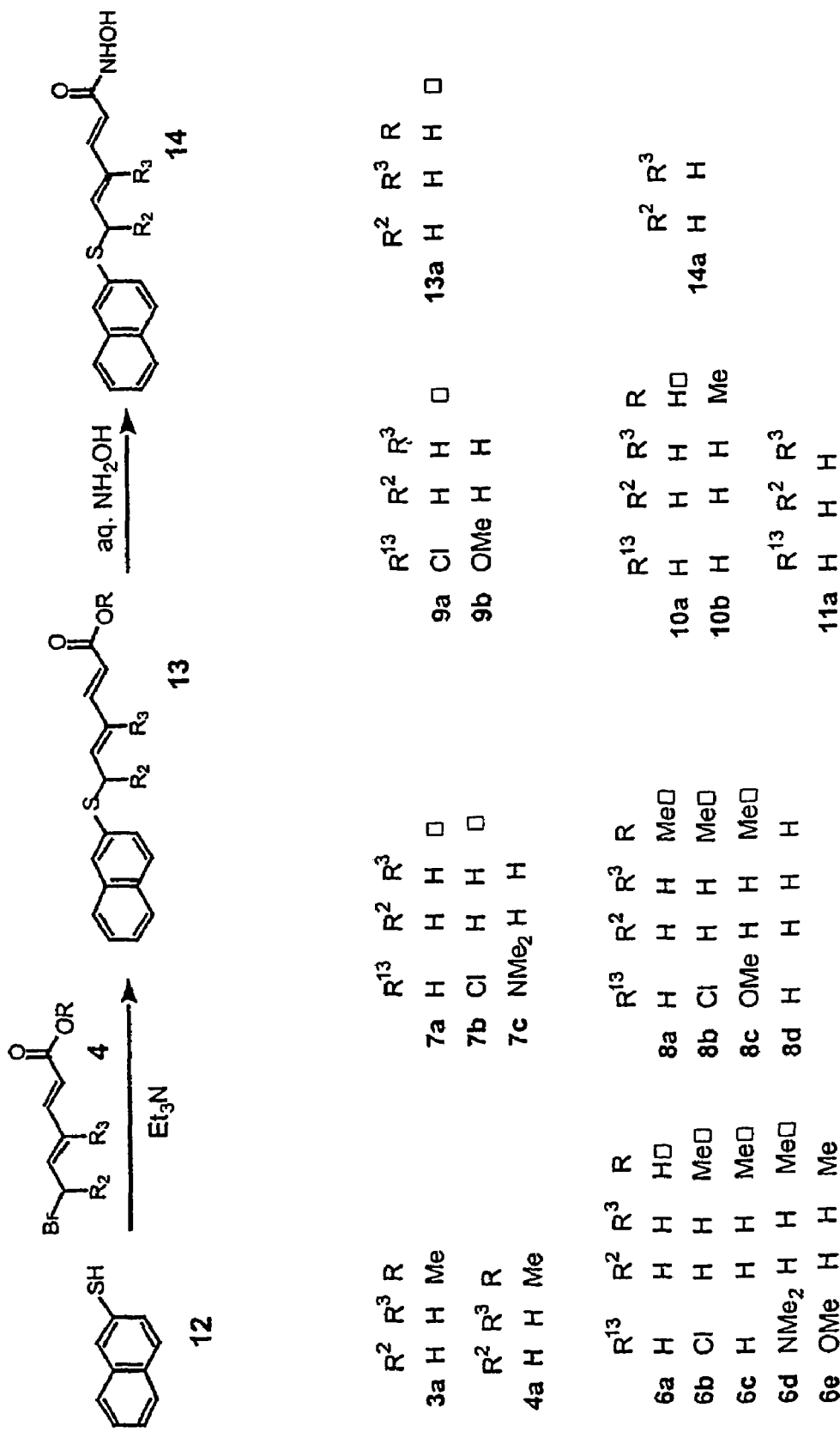
Figure 2:
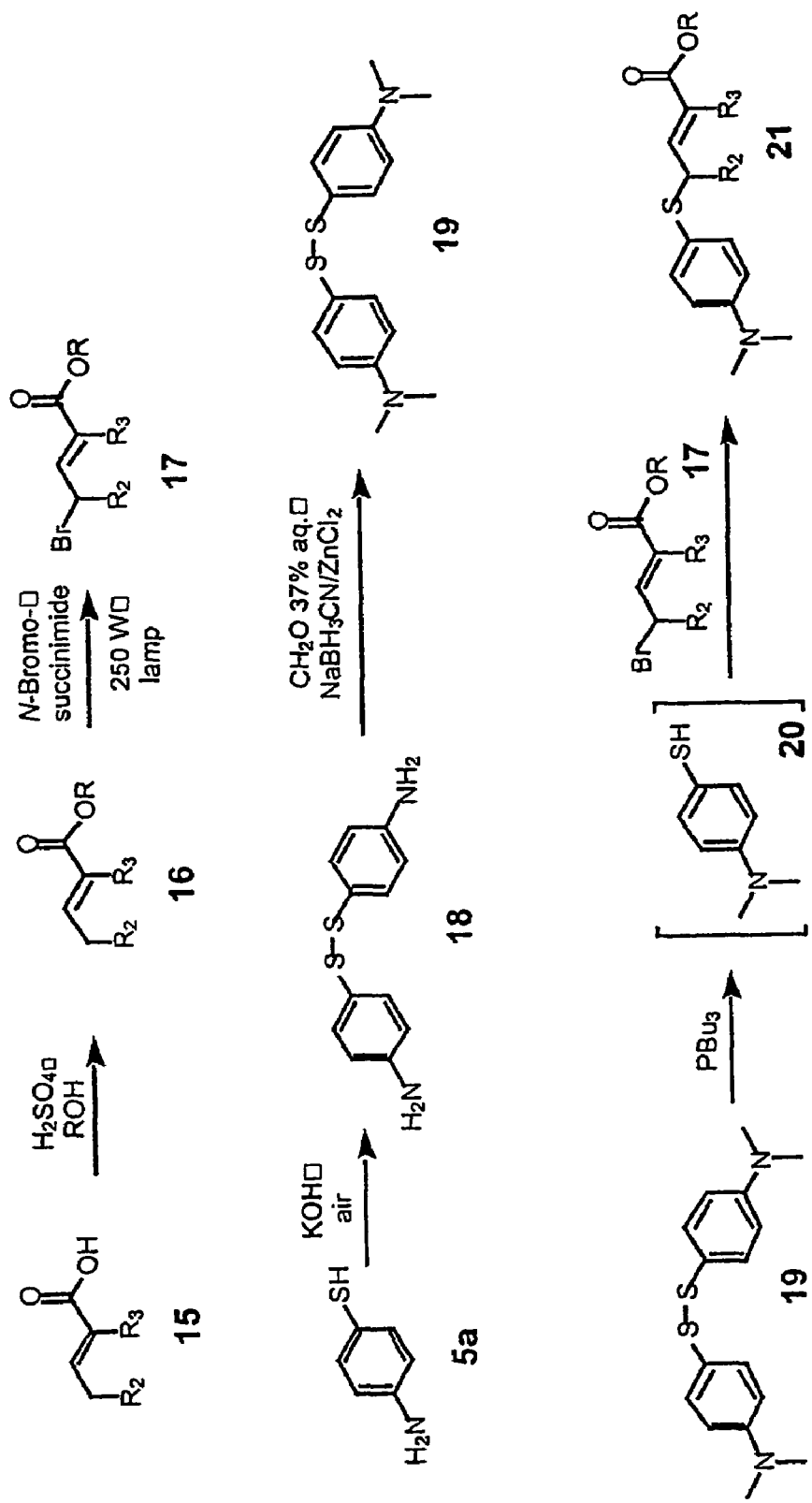
FIG. 2 shows reaction scheme 2.
Figure 2:
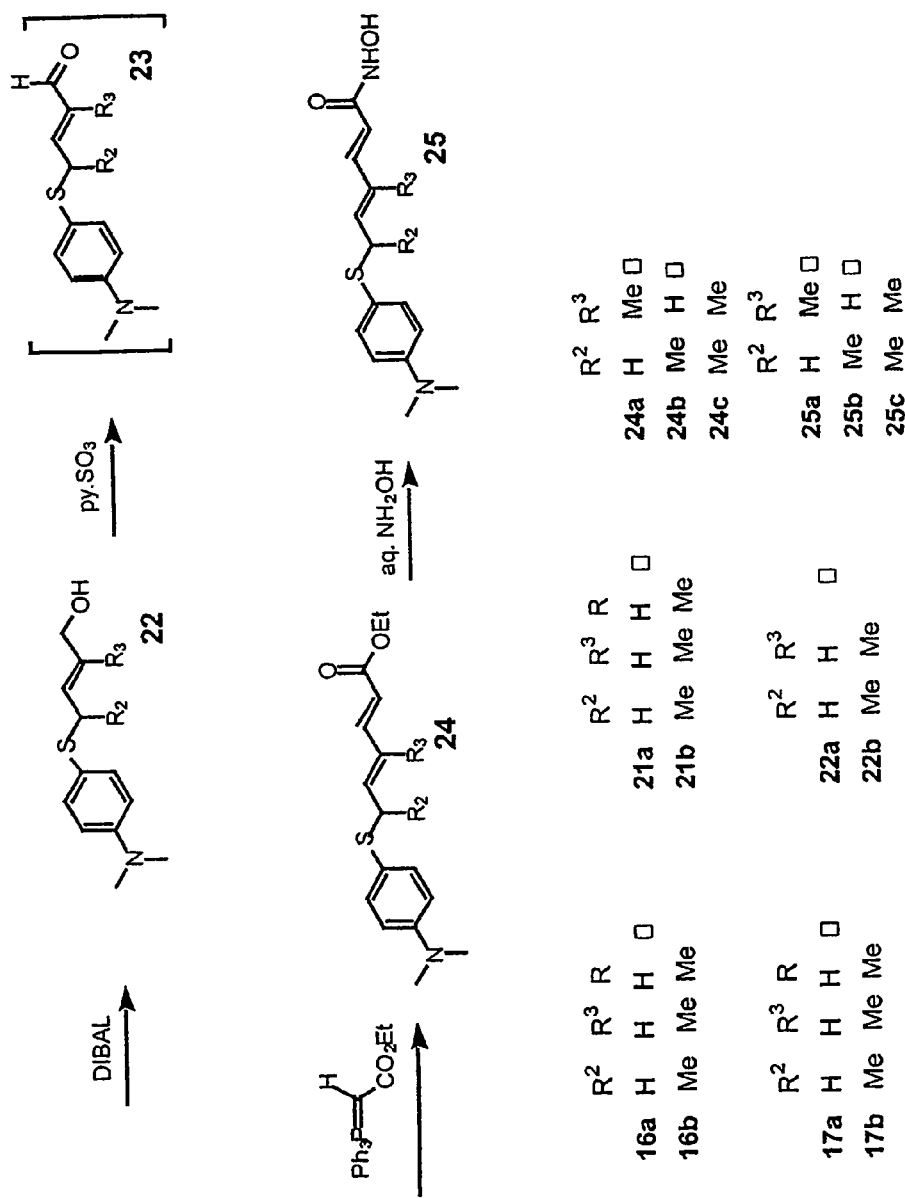
Figure 3:
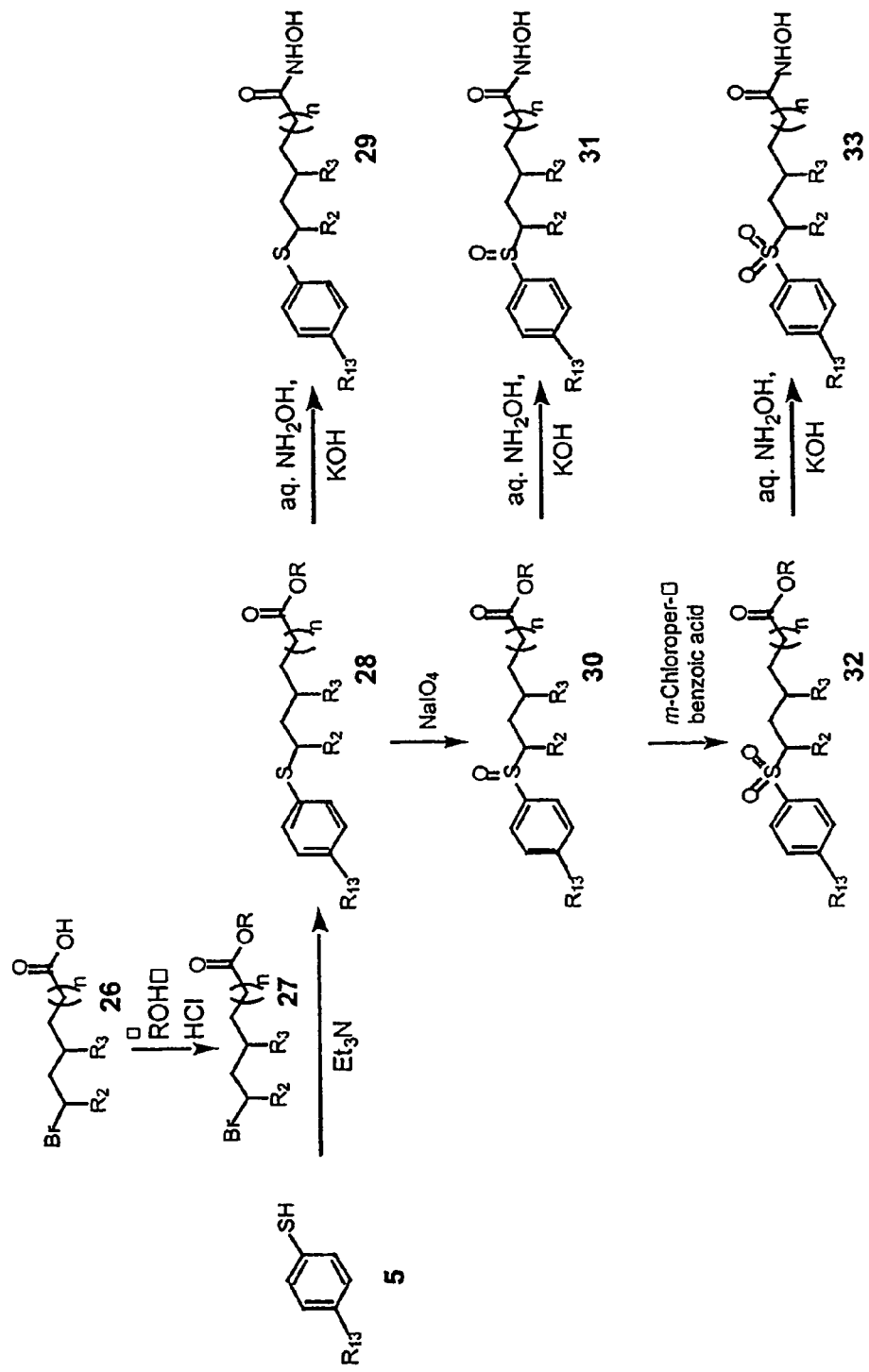
FIG. 3 shows reaction scheme 3.
Figure 4:
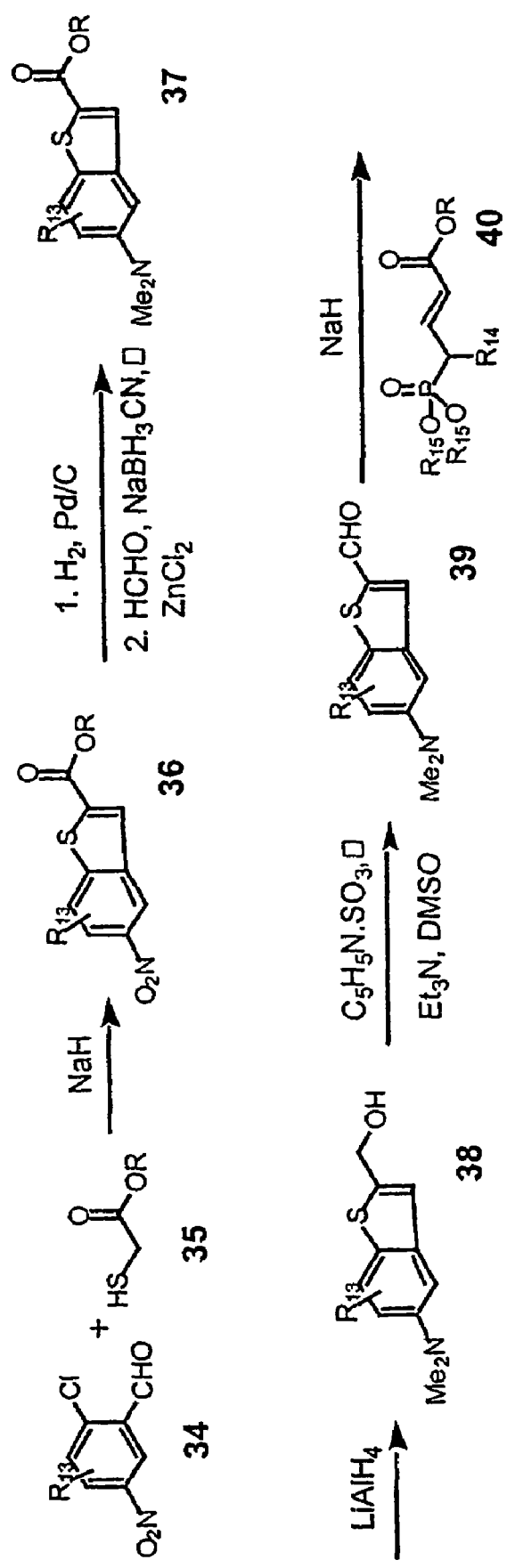
FIG. 4 shows reaction scheme 4.
Figure 4:
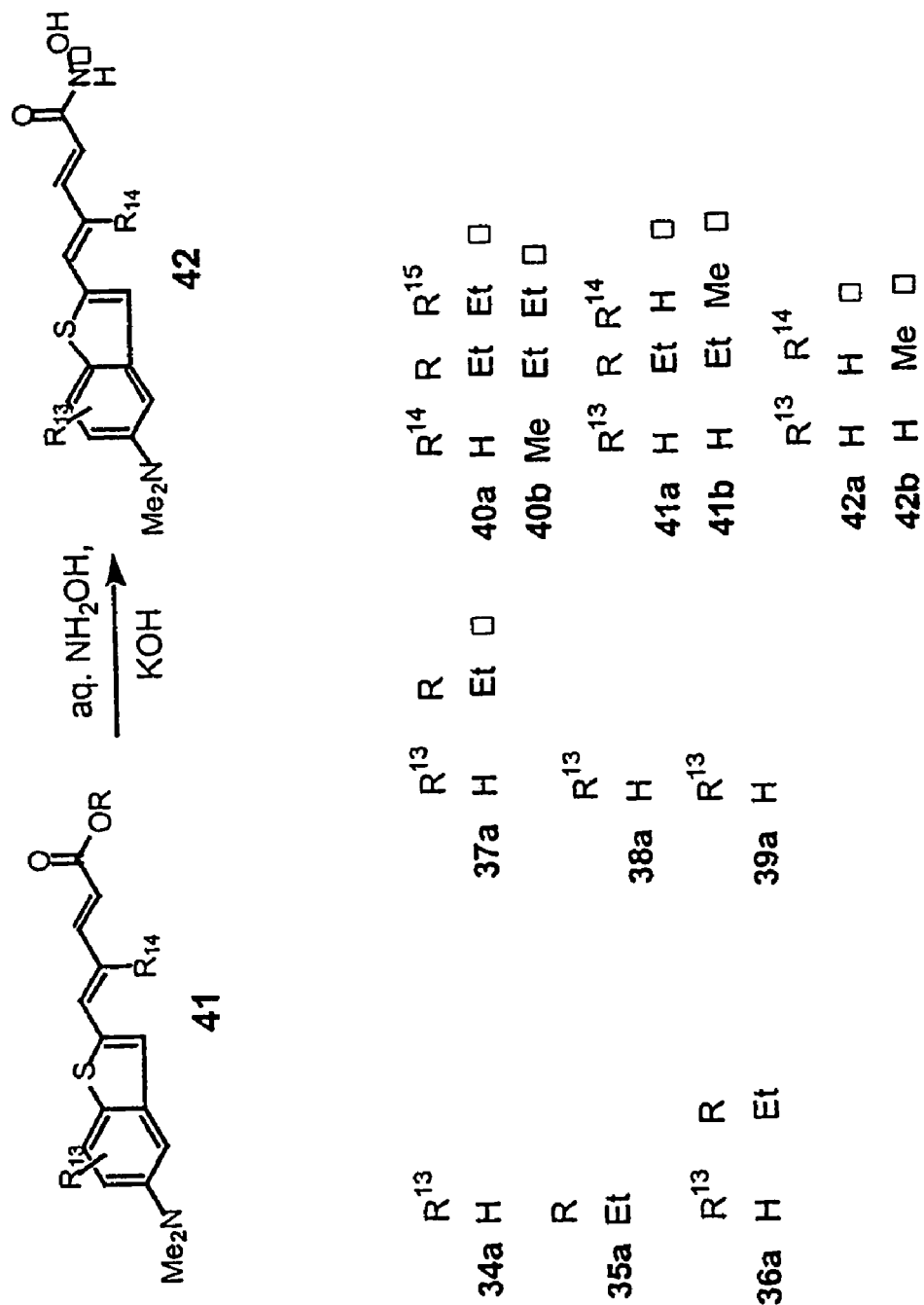
Figure 5:
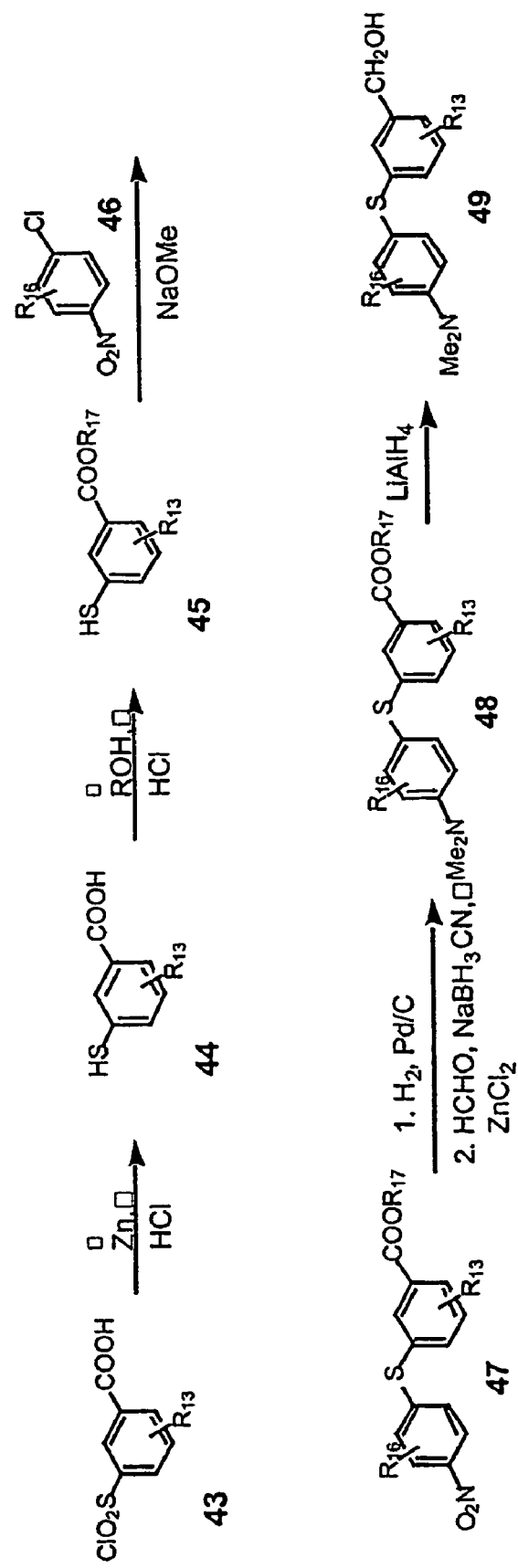
FIG. 5 shows reaction scheme 5.
Figure 5:
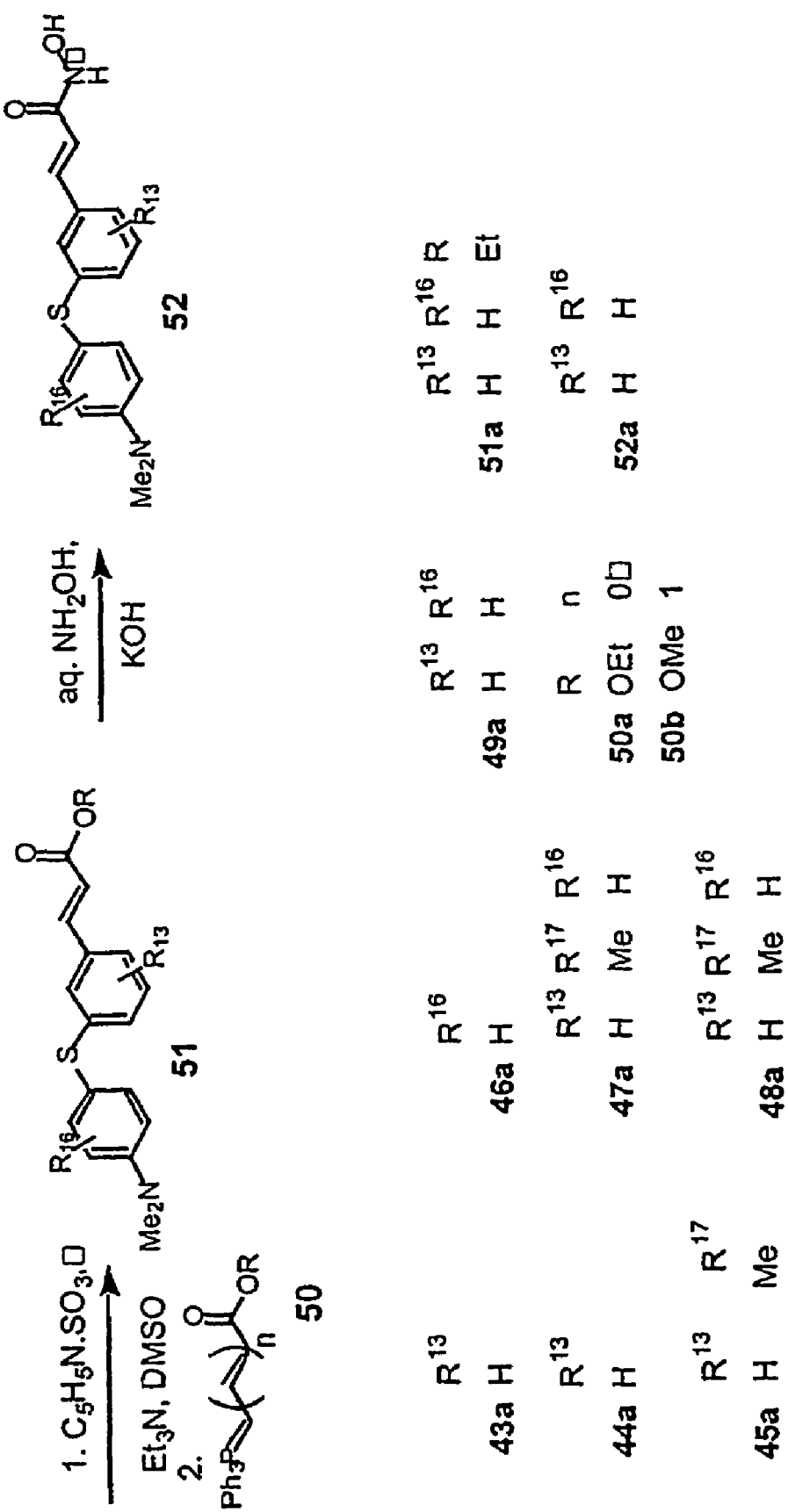
Figure 6:
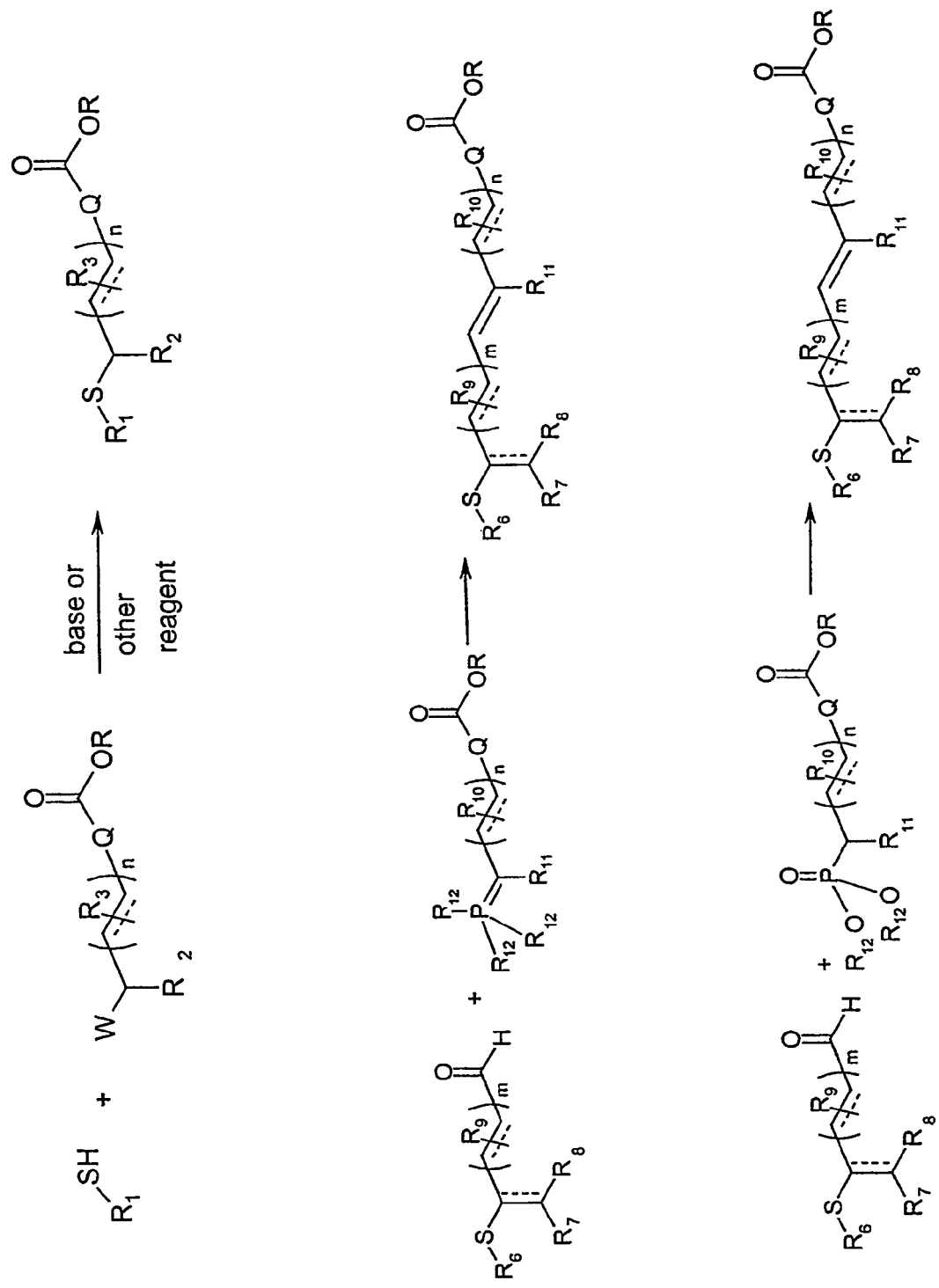
FIG. 6 shows a generalisation of the processes described in the second and third aspects of the invention.

Definitions:

In this specification the term "compound" includes "salt" or "hydrate" unless the context requires otherwise.

As used herein the term "halogen" or its abbreviation "halo" means fluoro, chloro, bromo or iodo.

As used herein the term "hetero" refers to the presence of one or more atoms that are not carbon atoms. Suitable heteroatoms include, oxygen, sulphur, nitrogen or phosphorus, represented as O, S, N and P, respectively.

As used herein the term "$(C_1-C_6)$ alkyl" refers to straight chain or branched chain hydrocarbon groups having from one to six carbon atoms. Illustrative of such alkyl groups are methyl, ethyl, propyl, isopropyl, butyl, isobutyl, sec-butyl, tert-butyl, pentyl, neopentyl, and hexyl. From one to five carbon atoms ($C_1-C_5$), or from one to four carbon atoms ($C_1-C_4$) may be preferred.

As used herein the term "$(C_1-C_{12})$ alkyl" refers to straight chain or branched chain hydrocarbon groups having from one to ten carbon atoms. Illustrative of such alkyl groups are methyl, ethyl, propyl, isopropyl, butyl, isobutyl, sec-butyl, tert-butyl, pentyl, neopentyl, hexyl, heptyl, octyl, nonyl, decyl, undecyl and dodecyl. From one to ten carbon ($C_1-C_{10}$) atoms or from one to six carbon atoms ($C_1-C_6$) may be preferred.

The presence of a partial carbon-carbon bond is indicated in general formula (I) and should be interpreted as showing either a full double bond or a single bond (in which case hydrogen atoms are included to make up the full valency of carbon).

The term "($C_6$ or $C_{10}$)aryl" includes phenyl and naphthyl.

As used herein, the term "$(C_5-C_8)$cycloalkyl" refers to an alicyclic group having from 5 to 8 carbon atoms. Illustrative of such cycloalkyl groups are cyclopentyl and cyclohexyl.

As used herein, the term "$(C_5-C_8)$cycloalkene ring" refers to an alicyclic ring having from 5 to 8 atoms and having in addition one or more double bonds. Illustrative of such cycloalkenyl groups are cyclopentenyl, cyclohexenyl, cycloheptenyl and cyclooctenyl.

In compounds of this invention, the presence of an asymmetric carbon atom gives rise to enantiomers. The presence of several asymmetric carbon atoms give rise to diastereoisomers, each of which consists of two enantiomers, with the appropriate R or S stereochemistry at each chiral centre. The invention is understood to include all such diastereoisomers, optically active enantiomers and mixtures thereof.

The term "suitable salt" refers to a salt prepared by contacting a compound of formula (I) with an acid or base whose counterpart ion does not interfere with the intended use of the compound. Examples include the sodium salt or magnesium salt of a phosphate derivative or the salt formed from a primary, secondary or tertiary amine where the compound of general formula (I) is a carboxylic acid. An example of a primary amine salt can be the cyclohexylammonium salt, a suitable secondary amine salt may be the piperidine salt and a tertiary amine salt may be the triethylamine salt.

References to a substituent group R in the specification define a group that may be independently be hydrogen, $C_1-C_6$ alkyl or substituted $C_1-C_6$ alkyl, or substituted benzyl ($C_6$ aryl). Where more than one group R is used to define a structural formula then each group R may independently have the meanings defined herein.

References to alkylamino include mono-, di-, or tri-nitro substituted carbon atoms unless the context specifies otherwise. References to amido include CONR, where R maybe Hydrogen.

References to a fused ring system include both aromatic and alicyclic ring systems. The ring may be fully or partially saturated or unsaturated.

Unless the context specifies otherwise, substitutions to benzene rings ($C_6$ aryl) may be at the ortho, meta or para positions, although substitution at the para position is preferred.

As used herein, the term "$(C_6-C_{10})$ heteroaryl" refers to a 6 or 10-membered ring system having one or more heteroatoms in the ring.

As used herein, the term "$(C_3-C_8)$ heterocycloalkenyl" refers to a ring system having from 3 to 8 members, preferably 5, 6 or 7 members, in which one or more heteroatoms is present in the ring.

As used herein, the term "$(C_5-C_8)$ heterocycloalkyl" refers to a ring system having from 5 to 8 members, preferably 5, 6 or 7 members, in which one or more heteroatoms is present in the ring.

Preferred compounds falling within the scope of general formula (I) are those in which $R^2$ and $R^3$ are both Hydrogen; $R^2$ is methyl ($CH_3$) and $R^3$ is Hydrogen; $R^2$ is Hydrogen and $R^3$ is methyl ($CH_3$); or $R^2$ and $R^3$ are both methyl ($CH_3$).

Preferably $R^1$ is ($C_6$ or $C_{10}$) aryl, optionally substituted by halo, preferably chlorine, by ($C_1-C_{10}$) alkoxy, preferably methoxy (—$OCH_3$), by ($C_1-C_{10}$) alkylamino, preferably dimethylamino.

Preferably X is —OH, —$OCH_3$, —$OC_2H_5$ or NHOH.

Preferably, Y is represented by one or two oxygen atoms.

When $R^2$ and $R^3$ are both Hydrogen (H), Y is equal to zero oxygen atoms, and n is equal to 1, $R^1$ maybe one of

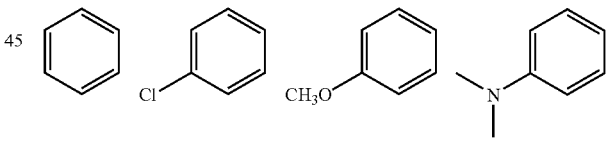

and X may be —OH, —$OCH_3$, —$OC_2H_5$ or NHOH

Examples of such compounds are compounds 6a, 6b, 6c, 6d, 6e, 7b, and 7c.

When $R^2$ and $R^3$ are both Hydrogen (H), Y is equal to one oxygen atom, and n is equal to 1, $R^1$ may be one of

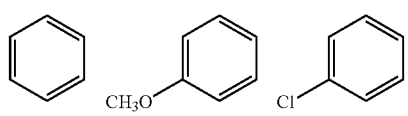

and X may be —OH, —$CH_3$, —$OC_2H_5$ or NHOH.

Examples of such compounds are compounds 8a, 8b, 8c, 8d, 9a, and 9b.

When $R^2$ and $R^3$ are both Hydrogen (H), Y is equal to two oxygen atoms and n is equal to 1, $R^1$ may be one of

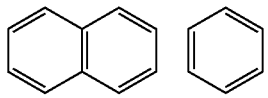

and X may be —OH, —CH$_3$, —OC$_2$H$_5$ or NHOH

Examples of such compounds are compounds 10a, 10b, 11a, 13b, and 14a.

When $R^2$ and $R^3$ are both methyl (CH$_3$), Y is equal to zero oxygen atoms, and n is equal to zero, $R^1$ may be

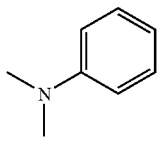

and X may be —OCH$_3$, —OC$_2$H$_5$ or —OH

Examples of such compounds are compounds 21b and 22b.

Particularly, preferred compounds are 6-benzenesulfonyl-hexa-2,4-dienoic acid hydroxamide (compound 11a) and 6-(-4-chlorobenzenesulfinyl)-hexa-2,4-dienoic acid hydroxamide (compound 9a).

Preferred compounds of general formula I include those in which, independently or in any compatible combination:

(6a)

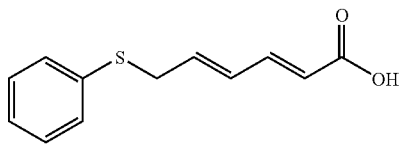

6-Phenylsulfanyl-hexa-2,4-dienoic acid (6b)

6-(4-Chloro-phenylsulfanyl)-hexa-2,4-dienoic acid methyl ester (6c)

6-Phenylsulfanyl-hexa-2,4-dienoic acid methyl ester

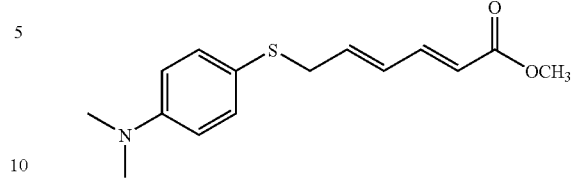

6-(4-Dimethylamino-phenylsulfanyl)-hexa-2,4-dienoic acid methyl ester (6d)

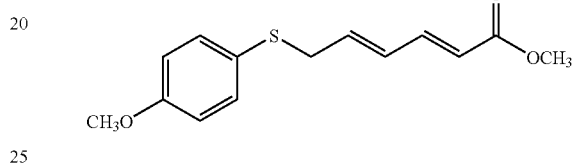

6-(4-Methoxy-phenylsulfanyl)-hexa-2,4-dienoic acid methyl ester (6e)

(7b)

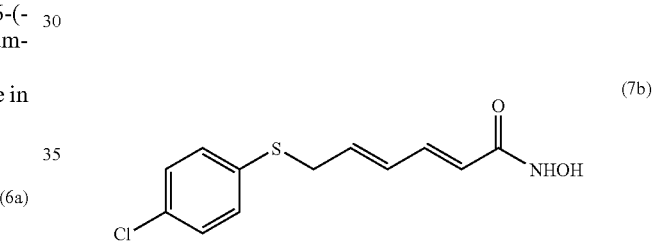

6-(4-Chloro-phenylsulfanyl)-hexa-2,4-dienoic acid hydroxyamide

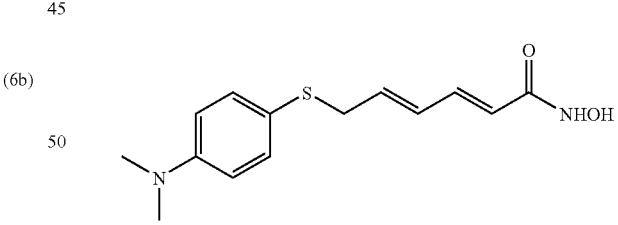

6-(4-Dimethylamino-phenylsulfanyl)-hexa-2,4-dienoic acid hydroxyamide (7c)

(8a)

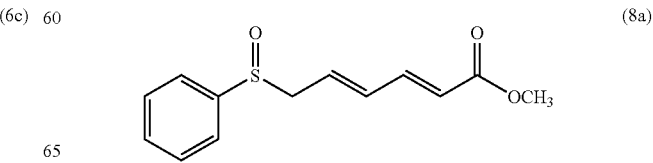

6-Phenylsulfinyl-hexa-2,4-dienoic acid methyl ester

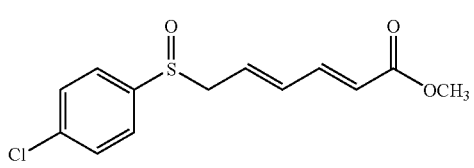
(8b)

6-(4-Chloro-benzenesulfinyl)-hexa-2,4-dienoic acid methyl ester

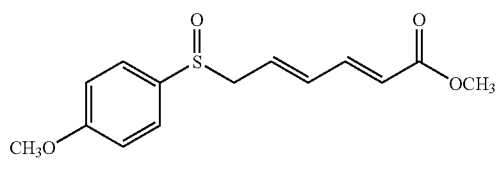
(8c)

6-(4-Methoxy-benzenesulfinyl)-hexa-2,4-dienoic acid methyl ester

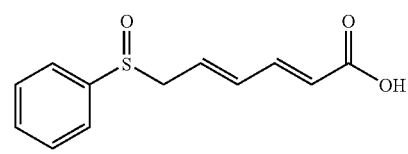

6-Benzenesulfinyl-hexa-2,4-dienoic acid (8d)

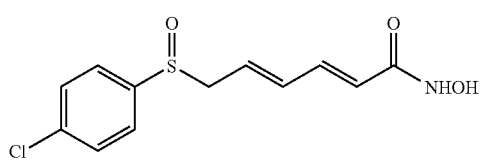
(9a)

6-(4-Chloro-benzenesulfinyl)-hexa-2,4-dienoic acid hydroxyamide

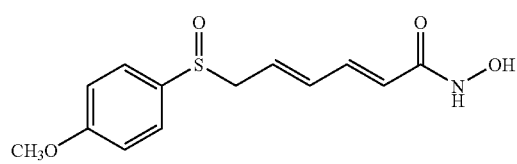
(9b)

6-(4-Methoxy-benzenesulfinyl)-hexa-2,4-dienoic acid hydroxyamide

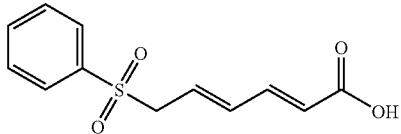
(10a)

6-Benzenesulfonyl-hexa-2,4-dienoic acid

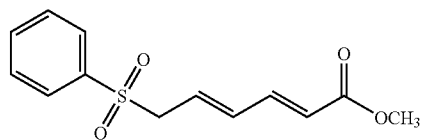
(10b)

6-Benzenesulfonyl-hexa-2,4-dienoic acid methyl ester

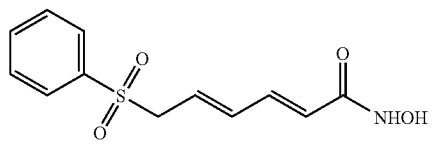

6-Benzenesulfonyl-hexa-2,4-dienoic acid hydroxyamide (11a)

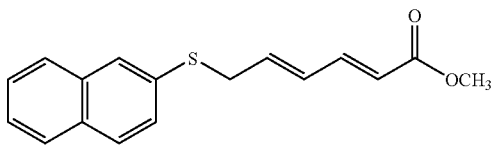

6-(Naphthalen-2-ylsulfanyl)-hexa-2,4-dienoic acid methyl ester (13b)

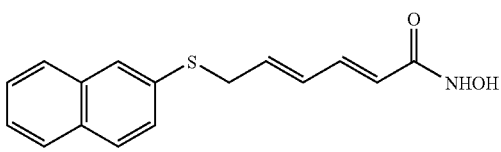

6-(Naphthalen-2-ylsulfanyl)-hexa-2,4-dienoic acid hydroxyamide (14a)

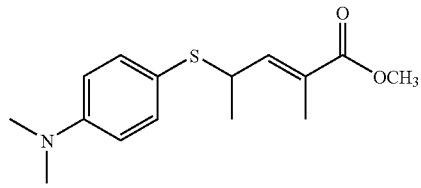

4-(4-Dimethylamino-phenylsulfanyl)-2-methyl-pent-2-enoic acid methyl ester

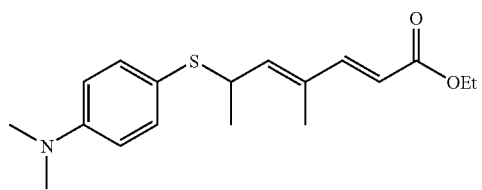

6-(4-Dimethylamino-phenylsulfanyl)-4-methyl-hepta-2,4-dienoic acid ethyl ester

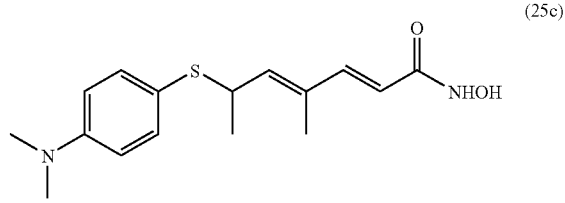

6-(4-Dimethylamino-phenylsulfanyl)-4-methyl-hepta-2,4-dienoic acid hydroxyamide or one of the following compounds,
6-(4-Chloro-phenylsulfanyl)-hexanoic acid methyl ester (28b)
7-(4-Chloro-phenylsulfanyl)-heptanoic acid ethyl ester (28c)
6-(4-Amino-phenylsulfanyl)-hexanoic acid methyl ester (28d)
6-(4-Dimethylamino-phenylsulfanyl)-hexanoic acid methyl ester (28e)
6-(4-((4-Chlorobenzyl)-methylamino)-phenylsulfanyl)-hexanoic acid methyl ester (28f)
6-(4-(4-Chlorobenzenesulfonylamino)-phenylsulfanyl)-hexanoic acid methyl ester (28g)
6-(4-Bromo-phenylylsulfanyl)-hexanoic acid methyl ester (28h)
6-(4'-Chloro-biphenyl-4-ylsulfanyl)-hexanoic acid methyl ester (28i)
6-(4-Chloro-phenylsulfanyl)-hexanoic acid hydroxyamide (29b)
6-(4-Dimethylamino-phenylsulfanyl)-hexanoic acid hydroxamide (29c)
6-(4-(4-Chlorobenzenesulfonylamino)-phenylsulfanyl)-hexanoic acid hydroxamide (29g)
6-(4'-Chloro-biphenyl-4-ylsulfanyl)-hexanoic acid hydroxamide (29i)
6-(4-Chloro-benzenesulfinyl)-hexanoic acid methyl ester (30b)
7-(4-Chloro-benzenesulfinyl)-heptanoic acid ethyl ester (30c)
6-(4-Dimethylamino-benzenesulfinyl)-hexanoic acid methyl ester (30e)
6-(4-((4-Chlorobenzyl)-methylamino)-benzenesulfinyl)-hexanoic acid methyl ester (30f)
6-(4'-Chloro-biphenyl-4-ylsulfinyl)-hexanoic acid methyl ester (30i)
6-(4-Chloro-benzenesulfinyl)-hexanoic acid hydroxyamide (31a)
7-(4-Chloro-benzenesulfinyl)-heptanoic acid hydroxyamide (31c)
6-(4-Dimethylamino-benzenesulfinyl)-hexanoic acid hydroxyamide (31e)
6-(4-((4-Chlorobenzyl)-methylamino)-benzenesulfinyl)-hexanoic acid hydroxamide (31f)
6-(4'-Chloro-biphenyl-4-sulfinyl)-hexanoic acid hydroxyamide (31i)
(2E,4E)-5-(5-Dimethylamino-benzo[b]thiophen-2-yl)-penta-2,4-dienoic acid ethyl ester (41a)
(2E,4E)-5-(5-Dimethylaminobenzo[b]thiophen-2-yl)-penta-2,4-dienoic acid hydroxamide (42a)
(E)-3-(3-(4-Dimethylamino-phenylsulfanyl)-phenyl)-acrylic acid ethyl ester (51a.
(E)-3-(3-(4-Dimethylamino-phenylsulfanyl)-phenyl)-N-hydroxy-acrylamide (52a)

In an alternative embodiment of the invention, the substituted carbonyl group -COX shown in general formula (I) may be replaced with —CH$_2$OH. An example of such a compound of this type is,

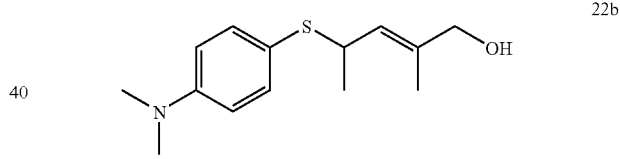

4-(4Dimethylamino-phenylsulfanyl)-2-methyl-pent-2-en-1-ol

According to a second aspect of the invention there is provided a process for the preparation of a compound of general formula (I), comprising the addition of a compound of general formula (II) to general formula (III),

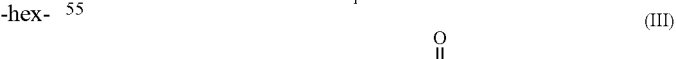

optionally followed by hydrolysis, or oxidation then hydrolysis, where W is a leaving group that may be a halogen atom (e.g. bromine, chlorine, iodine), or benzene sulphonate, para-toluenesulphonate, trifluoromethylsulphonate.

Hydrolysis may be suitably carried out under alkaline conditions, for example with aqueous hydroxylamine, or aqueous hydroxylamine in the presence of an alkali metal hydroxide in aqueous solution, e.g. sodium hydroxide, or potassium hydroxide. Oxidation may be carried out using a peracid, for example meta-choloroperoxybenzoic acid, or sodium periodate.

A preferred embodiment of the process of this aspect of the invention may comprise the addition of a compound of general formula (5) to general formula (4),

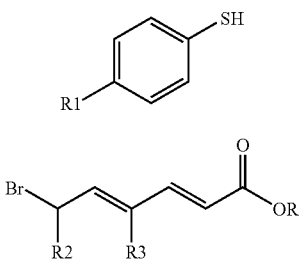

optionally followed by hydrolysis, or oxidation then hydrolysis.

A preferred embodiment of the process of this aspect of the invention may comprise the addition of a compound of general formula (20) to a compound of general formula (17),

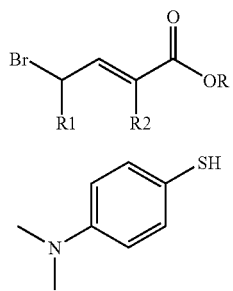

optionally followed by hydrolysis, or oxidation then hydrolysis.

Another preferred embodiment of the process of this aspect of the invention may comprise the addition of a compound of general formula (5) to a compound of general formula (27)

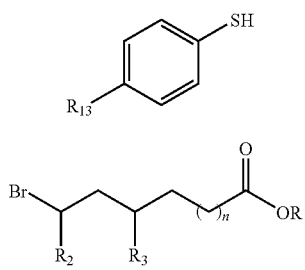

optionally followed by hydrolysis, or oxidation then hydrolysis. $R^{13}$ may be as for $R^2$ defined above.

It may also be desired to further derivatise compounds prepared according to the process of this aspect of the invention by further reacting the aldehyde compound corresponding to the product of the addition of a compound of general formula (II) to general formula (III), with a stabilised phosphorous ylid compound.

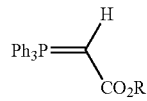

or the reaction may be carried out using a compound of the formula, in which $R^{12}$ may as defined for $R^{15}$ herein

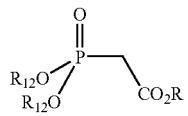

Suitably, the stabilised phosphorous ylid compound is (triphenylphosphanylidene)-acetic acid ethyl ester.

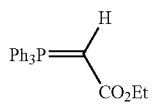

$R^{14}$ may be hydrogen, $(C_1-C_6)$ alkyl, preferably methyl or ethyl, or phenyl, or a 5-, 6- or 7-membered heterocycle ring (heterocycloalkyl or heterocycloalkenyl), as defined above, or a substituted derivative thereof.

$R^{15}$ may be hydrogen, $(C_1-C_6)$ alkyl, preferably methyl or ethyl, or phenyl, or a 5-, 6- or 7-membered heterocycle ring (heterocycloalkyl or heterocycloalkenyl), as defined above, or a substituted derivative thereof.

$R^{17}$ may be as defined for R above.

According to a third aspect of the invention, there is provided a process for the preparation of a compound of general formula (I), comprising the addition of a compound of general formula (IV) to general formula (Va) or (Vb),

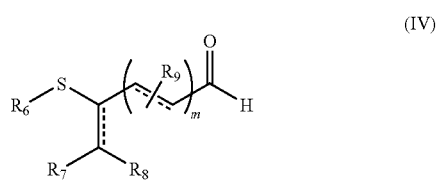

(IV)

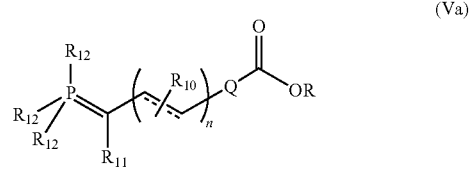

(Va)

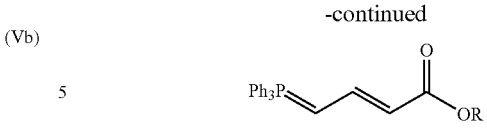

(Vb)

optionally followed by hydrolysis, or oxidation then hydrolysis.

$R^6$ may as defined for $R^1$ above $R^7, R^8, R^9$, and $R^{10}$, may each independently be as defined for $R^2$ above.

$R^{11}$ may as for $R^{14}$ defined herein $R^{12}$ may be as for $R^{15}$ as defined herein.

$R^6$ and $R^7$ can be fused as for $R^1$ and $R^2$ as defined above.

$R^8$ and $R^9$ can be fused as defined for $R^2$ and $R^3$ as defined above.

A preferred embodiment of the process of this aspect of the invention may comprise the addition of a compound of general formula (39) to a compound of general formula (40)

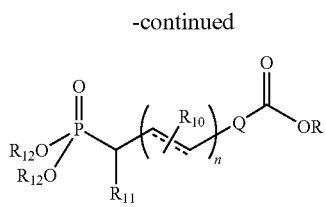

39

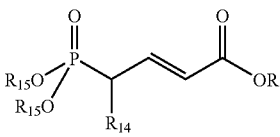

40 or a compound of general formula (50)

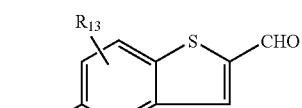

50 optionally followed by hydrolysis, or oxidation then hydrolysis.

A preferred embodiment of the process of this aspect of the invention may comprise the addition to a compound of general formula (50) the aldehyde obtained by oxidation of a compound of general formula (49)

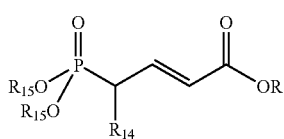

49

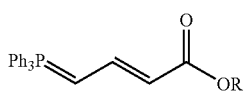

50 or a compound of general formula (40)

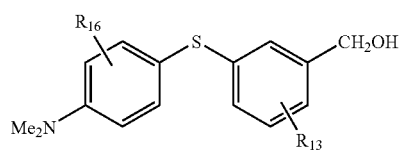

40 optionally followed by hydrolysis, or oxidation then hydrolysis.

Synthetic Routes.

In all Schemes and in the experimental section, all the C=C double bonds that form part of the chain attached to the hydroxamic acid were isolated as the trans-isomer or trans-trans isomer ($R^1$ and $R^2$, or $R^2$ and $R^3$ are ignored for the purpose of the stereochemical description 'trans' used above). In Scheme 1 is shown a general route to hydroxamic acid derivatives containing a sulfide (type 7), a sulfoxide (type 9) and a sulfone (type 11) linkage. Those types can be accessed through a sequence involving addition of a thiol 5 to an unsaturated bromo ester 4 (or similar chloro or iodo derivative) to give an ester 6 which can be oxidised to 8 using sodium metaperiodate (or similar oxidising agent such as hydrogen peroxide). The corresponding sulfones 10 can be prepared either by oxidation of 6 or 8, usually using a peracid, such as meta-chloroperoxybenzoic acid. Reaction of 6, 8 or 10 with hydroxylamine (usually an aqueous solution, but otherwise a salt such as hydroxylamine hydrochloride together with a base, typically sodium hydroxide or potassium hydroxide). The unsaturated bromo esters 4 were prepared by bromination of the corresponding esters 3, usually using N-bromosuccinimide together with a sun lamp of 250 W (i.e. in the range 100 to 500 W for small-scale reactions). Such brominations can also be performed using a peroxide initiator such as dibenzoyl peroxide. The esters 3 can be conveniently prepared by treating the corresponding carboxylic acid 2 with the appropriate alcohol (ROH) in the presence of sulfuric acid (or other catalyst).

Although a sequence of general utility is implied in Scheme 1, compounds of particular interest include $R^2=R^3=H$; $R^2=Me$, $R^3=H$; $R^2=H$, $R^3=Me$ and $R^2=R^3=Me$ for the set of compounds 2-4 and 6-11, 13 and 14.

Scheme 1 is intended to include aromatic and heteroaromatic rings, single, fused or poly-condensed ring systems without limitation (in place of the single benzene ring shown for compounds 5-11) and with or without a wide variety of substituents. As an example, 2-naphthalenethiol 12 was shown to react with bromo ester 4 to give ester 13 which was reacted with aqueous hydroxylamine to give hydroxamic acid 14. Hydroxamic acids of type 7, 9, 11 and 14 are of particular interest as inhibitors of histone deacetylase. Some of the corresponding carboxylic acids 6, 8, 10 and 13 are also inhibitors of histone deacetylase.

In Scheme 2 is shown a general route to hydroxamic acid derivatives containing an N,N-dimethylamino group (e.g.

25), and the corresponding esters (e.g. 24) from which they are made. Hydrolysis of esters such as 24 provides the corresponding carboxylic acids which may also be inhibitors of histone deacetylase. The hydroxamic acid derivatives such as 25 are especially noteworthy as inhibitors of histone deacetylase, and they possess close structural analogies to the trichostatin A, a potent inhibitor of histone deacetylase. Scheme 2 is illustrated with an N,N-dimethylamino group, but is intended to include a wide range of substituents attached to nitrogen, including but not limited to monoalkyl, dialkyl, alkyl together with aryl, diaryl, one or more heterocyclic substituents and a wide variety of other substituents with unsaturated and/or heteroatom functionality. The synthetic route of Scheme 2 is intended to apply to additional substituents in either the ortho- or para-positions, or both. It is also intended to apply to more than one such amino (or similar N-substituent) placed at a combination of two or more of the ortho-, meta- or para-positions as appropriate.

A principal feature of Scheme 2 is the reductive amination of a carbonyl compound (illustrated with formaldehyde, but applicable to a wide variety of carbonyl compounds) with the disulfide 18 followed by a cleavage using tri-n-butylphosphine (or other phosphine) to give in situ the thiol 20 which is reacted with an unsaturated bromo ester 17 to give the sulfide 21. Reduction of 21 is conveniently achieved using di-isobutylaluminium hydride (DIBAL) to give the alcohol 22 which is treated with pyridine-sulfur trioxide complex to give the aldehyde 23 which need not be isolated and which is reacted in situ with a stabilised phosphorus ylid such as (triphenylphosphanylidene)-acetic acid ethyl ester to give 24 or a related sulfide that is reacted with hydroxylamine (or a salt or other derivative of hydroxylamine) to give the hydroxamic acid such as 25. The route in Scheme 2 is particularly effective for the incorporation of amino and other nitrogen-containing substituents. The scope of the reductive amination is such that the aromatic amino group (ArNH$_2$) may be reacted first with one aldehyde or ketone under reductive conditions, and the resulting secondary amine then reacted with a second aldehyde or ketone (which may be the same as the first aldehdye or ketone or different from it), again under reductive conditions.

In Scheme 3 is shown a general route to hydroxamic acid derivatives containing a sulfide (type 29), a sulfoxide (type 31) and a sulfone (type 33) linkage. Those types can be accessed through a sequence involving addition of a thiol 5 to a bromo ester 27 (or similar chloro or iodo derivative) to give an ester 28 which can be oxidised to 30 using sodium metaperiodate (or similar oxidising agent such as hydrogen peroxide). The corresponding sulfones 32 can be prepared either by oxidation of 28 or 30, usually using a peracid, such as meta-chloroperoxybenzoic acid. Reaction of 28, 30 or 32 with hydroxylamine in the presence or absence of alkali, typically potassium hydroxide or sodium hydroxide (usually an aqueous solution, but otherwise a salt such as hydroxylamine hydrochloride together with a base, typically sodium hydroxide or potassium hydroxide). The bromo esters 27 can be conveniently prepared by treating the bromo acids 26 with the appropriate alcohol (ROH) in the presence of sulfuric acid (or other catalyst).

A useful feature of Scheme 3 is the reductive amination of a carbonyl compound (illustrated with formaldehyde, but applicable to a wide variety of carbonyl compounds) with the compounds 28 that possess an aromatic amino group (e.g. $R^{13}$=NH$_2$). The general procedure of reductive amination using a combination of formaldehyde or its equivalent with another aldehyde, especially an aromatic or heteroaromatic aldehyde, has been worked out and is exemplified in the conversion of amine 28d into the tertiary amine 28f (using p-chlorobenzaldehyde and formaldehyde). The incorporation of such a procedure into Scheme 3 is particularly effective for the incorporation of amino and other nitrogen-containing substituents. The scope of the reductive amination is such that the aromatic amino group (ArNH$_2$) may be reacted first with one aldehyde or ketone under reductive conditions, and the resulting secondary amine then reacted with a second aldehyde or ketone (which may be the same as the first aldehyde or ketone or different from it), again under reductive conditions. Thus, types 28 where $R^1$ or other aryl substituent is amino (NH$_2$) can be converted into their derivatives that contain a secondary or tertiary amine, and those amino esters may then be hydrolysed to the corresponding carboxylic acids or converted into the corresponding hydroxamic acids by methods described herein.

A notable optional feature of Scheme 3 is the possibility of coupling a substituent on the aromatic (or heteroaromatic) ring with a boronic acid by means of a Suzuki reaction, usually catalysed by palladium in ligated form. An example is the conversion of bromo compound 28h into the biphenylyl derivative 28i. Several other metal-catalysed coupling processes of 28h, or similar such compounds (chloride, O-trifluoromethanesulfonate etc.) can be envisaged, notably Heck reactions and related processes. Such metal-catalysed processes could also be carried out at an earlier stage, prior to reaction with the alkyl halide such as 27 (probably with suitable protection at sulfur).

Scheme 3 is intended to include aromatic and heteroaromatic rings, single, fused or poly-condensed ring systems without limitation (in place of the single benzene ring shown for compounds 26-33) and with or without a wide variety of substituents. Hydroxamic acids of types 29, 31 and 33 are of particular interest as inhibitors of histone deacetylase. Some of the corresponding carboxylic esters 28, 30 and 32, and/or their corresponding carboxylic acids are also likely to be inhibitors of histone deacetylase.

Although a sequence of general utility is implied in Scheme 3, compounds of particular interest include $R^2$=$R^3$=H; $R^2$=Me, $R^3$=H; $R^2$=H, $R^3$=Me and $R^2$=$R^3$=Me and with n=1 or 2 for the set of compounds 26-33.

In Scheme 4 is shown a general route to hydroxamic acid derivatives containing an N,N-dimethylamino group attached to a benzothiophene ring (e.g. 42), and the corresponding esters (e.g. 41) from which they are made. Hydrolysis of esters such as 41 provides the corresponding carboxylic acids that may also be inhibitors of histone deacetylase. Scheme 4 is illustrated with an N,N-dimethylamino group, but is intended to include a wide range of substituents attached to nitrogen, including but not limited to monoalkyl, dialkyl, alkyl together with aryl, diaryl, one or more heterocyclic substituents and a wide variety of other substituents with unsaturated and/or heteroatom functionality. The synthetic route of Scheme 4 is intended to apply to additional substituents on either ring, or on both. It is also intended to apply to more than one such amino (or similar N-substituent) placed at various positions.

A principal feature of Scheme 4 is the reductive amination of a carbonyl compound (illustrated with formaldehyde, but applicable to a wide variety of carbonyl compounds) with the nitro compound 36. Although not illustrated as such in Scheme 4, the general procedure of reductive amination using a combination of formaldehyde or its equivalent with another aldehyde, especially an aromatic or heteroaromatic aldehyde, has been worked out and is exemplified in the conversion of amine 28d into the tertiary amine 28f (using p-chlorobenzaldehyde and formaldehyde). Reduction of 37 or a secondary or tertiary amine in which the dimethylamino group has been replaced by other substituents is conveniently achieved using lithium aluminium hydride to give the alcohol 38 which is treated with pyridine-sulfur trioxide complex to give the aldehyde 39 which is reacted with a phosphonate (40) (or as appropriate a stabilised phosphorus ylid such as (triphenylphosphanylidene)-acetic acid ethyl ester (or a vinylogous homologue, especially n=1)) to give 41 or a related benzothiazole that is reacted with hydroxylamine in the presence or absence of alkali, typically potassium hydroxide or sodium hydroxide (usually an aqueous solution, but otherwise a salt such as hydroxylamine hydrochloride together with a base, typically sodium hydroxide or potassium hydroxide), to give the hydroxamic acid such as 42. The route in Scheme 4 is particularly effective for the incorporation of amino and other nitrogen-containing substituents. The scope of the reductive amination is such that the aromatic amino group ($ArNH_2$) may be reacted first with one aldehyde or ketone under reductive conditions, and the resulting secondary amine then reacted with a second aldehyde or ketone (which may be the same as the first aldehyde or ketone or different from it), again under reductive conditions.

Scheme 4 is intended to include aromatic and heteroaromatic rings, single, fused or poly-condensed ring systems without limitation (in place of the single substituent $R^1$ shown for compounds 34, 36-39, 41 and 42) and with or without a wide variety of substituents. Hydroxamic acids of types 42 are of particular interest as inhibitors of histone deacetylase. Some of the corresponding carboxylic esters and/or their corresponding carboxylic acids are also likely to be inhibitors of histone deacetylase.

Although a sequence of general utility is implied in Scheme 4, compounds of particular interest include $R^{15}$=H or Me and with n=1 or 2 for the set of compounds 41 (R=H, methyl or ethyl) and 42. Also of interest are the same compounds but with a partly saturated chain, with or without substituents additional to those given in type 41 and 42. For example, a saturated or partly saturated phosphonate or phosphonium ylid when reacted with 39 would give a partly saturated system corresponding to 41 which could be converted into the hydroxamic acids corresponding to 42. Alternatively, selective reduction of 41 at the site adjacent to the benzothiazole ring could be achieved, perhaps with a silane-acid reagent such as $Et_3SiH$-TFA. Lastly, fully saturated chains could be obtained by catalytic hydrogenation, typically using hydrogen and a catalyst of palladium on carbon (or other reduction method or different reducing system) of the double bonds in 41. The esters so obtained could then be reacted converted by the methods previously outlined into the saturated chain hydroxamic acids corresponding to 42.

In Scheme 5 is shown a general route to hydroxamic acid derivatives containing a sulfide (type 52). Those types can be accessed through a sequence involving addition of a thiol 45 to a p-chloro nitro aromatic or heteroaromatic compound (and its related halo or other displaceable substituent analogues) such as 46 to give a sulfide 47 whose nitro group can be reduced to amino which either by isolation or preferably in situ can be reductively aminated according to the procedures and scope described above. Thus, the general procedure of reductive amination using a combination of formaldehyde or its equivalent with another aldehyde, especially an aromatic or heteroaromatic aldehyde, has been worked out and is exemplified in the conversion of amine 47a into the tertiary amine 48a (using and formaldehyde). The scope of the reductive amination is such that the aromatic amino group ($ArNH_2$) may be reacted first with one aldehyde or ketone under reductive conditions, and the resulting secondary amine then reacted with a second aldehyde or ketone (which may be the same as the first aldehyde or ketone or different from it), again under reductive conditions.

Reduction of amine 48 or a secondary or tertiary amine in which the dimethylamino group has been replaced by other substituents is conveniently achieved using lithium aluminium hydride (but also possibly by other reducing agents and not excluding the possibility of catalytic reduction) to give the alcohol 49 which is treated with pyridine-sulfur trioxide complex to give the aldehyde corresponding to 49 which (preferably in situ) is reacted with a stabilised phosphorus ylid 50 such as (triphenylphosphanylidene)-acetic acid ethyl ester (or a vinylogous homologue, especially n=0 or 1) to give 51 or a related sulfide that is reacted with hydroxylamine in the presence or absence of alkali, typically potassium hydroxide or sodium hydroxide (usually an aqueous solution, but otherwise a salt such as hydroxylamine hydrochloride together with a base, typically sodium hydroxide or potassium hydroxide), to give the hydroxamic acid such as 52.

It is expected that sulfoxides and sulfones corresponding to 51 can be prepared by oxidation, principal using a peracid, such as meta-chloroperoxybenzoic acid; but also possibly by other reagents such as dioxiranes or air and a catalyst that may or may not contain a metal, salts of a metal or a combination of metals or their salts or metals with salts. Further it is expected that a number of the sulfoxides and/or sulfones corresponding to 51 (especially $R^4$=H, Me or Et) and the sulfoxides and/or sulfones corresponding to 52 will significantly inhibit histone deacetylase.

The esters 45 can be conveniently prepared by treating the carboxylic acids 44 with the appropriate alcohol (ROH) in the presence of sulfuric acid (or other catalyst). The carboxylic acids 44 can be conveniently prepared by treating the carboxylic acids 43 with a mixture of zinc and hydrochloric acid. (A metal other than zinc could also be suitable, including iron and also tin).

Scheme 5 is intended to include aromatic and heteroaromatic rings, single, fused or poly-condensed ring systems without limitation, (in place of the single benzene ring shown for compounds 43-46 and/or in place of one or other or both of the benzene rings shown for compounds 47-52) and with or without a wide variety of substituents in any of those cases.

Although a sequence of general utility is implied in Scheme 5, compounds of particular interest for the set of compounds 51 (R=H, methyl or ethyl) and similarly for 52, those being likely to be inhibitors of histone deacetylase, especially the latter. Also of interest are the same compounds but with a partly or fully saturated chain, with or without substituents additional to those given in type 51 and 52. For example, a saturated or partly saturated phosphonate or phosphonium ylid when reacted with 49 would give a partly saturated system corresponding to 51 that could be converted into the hydroxamic acids corresponding to 52. Alternatively, selective reduction of 51 (n=2) at the site adjacent to the (hetero)aromatic ring could be achieved, perhaps with a silane-acid reagent such as $Et_3SiH$-TFA. Lastly, fully saturated chains could be obtained by catalytic hydrogenation, typically using hydrogen and a catalyst of palladium on carbon (or other reduction method or different reducing system) of the double bonds in 51. The esters so obtained could then be reacted converted by the methods previously outlined into the saturated chain hydroxamic acids corresponding to 42.

In the above reaction schemes, reference is made to the use of a stabilised phosphorous ylid or a phosphonate compound (e.g. 40 or 50) and either can be used if appropriate. It will also be apparent that the phosphorous ylid or a phosphonate compound can be increased in carbon chain length so as to increase the overall carbon chain length of the final product as desired.

According to a fourth aspect of the invention, there is provided a pharmaceutical composition comprising a compound of general formula (I), and optionally a pharmaceutically acceptable adjuvant and/or diluent.

The medicament will usually be supplied as part of a sterile, pharmaceutical composition which will normally include a pharmaceutically acceptable carrier. This pharmaceutical composition may be in any suitable form, (depending upon the desired method of administering it to a patient).

It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions)

Suitable excipients for tablets or hard gelatine capsules include lactose, maize starch or derivatives thereof stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6):318 (1986).

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastiles and mouth washes. Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the substance of the present invention can vary between wide limits, depending upon the disease or disorder to be treated, the age and condition of the individual to be treated, etc. and a physician will ultimately determine appropriate dosages to be used.

The dosage depends on a variety of factors including the age, weight and condition of the patient and the route of administration. The dosage for a particular patient will be determined by a physician. Typically, however, the dosage adopted for each route of administration when a compound of the invention is administered to adult humans is 0.001 to 500 mg/kg, most commonly in the range of 0.01 to 100 mg/kg, body weight, for instance, 0.01 to 50 mg/kg. Such a dosage may be given, for example, from 1 to 5 times daily by bolus infusion, infusion over several hours and/or repeated administration. The dosage and timing of administration of, for example, another chemotherapeutic or antineoplastic agent which may be given to a cancer patient with a compound of the invention will similarly be dependent on a variety of factors and will be determined by a physician.

A compound of formula (I) or a pharmaceutically acceptable salt thereof is formulated for use as a pharmaceutical composition also comprising a pharmaceutically acceptable carrier or diluent. The compositions are typically prepared following conventional methods and are administered in a pharmaceutically suitable form. Preferred pharmaceutical compositions are sterile and pyrogen-free. Further the pharmaceutical compositions provided by the invention typically contain a compound of the invention which is a substantially pure optical isomer.

Compositions suitable for oral administration may, if required, contain a colouring or flavouring agent. Typically, a capsule or tablet comprises from 5 to 500 mg, preferably 10 to 500 mg, more preferably 15 to 100 mg, of a compound of formula (I) or a pharmaceutically acceptable salt thereof.

This dosage may be repeated as often as appropriate. If side effects develop the amount and/or frequency of the dosage can be reduced, in accordance with normal clinical practice.

According to a fifth aspect of the invention there is provided a compound of general formula (I) for use in medicine.

Without wishing to be bound by theory, it is believed that the diseases in which the compounds of the present invention may find greatest application in medical treatment will be in the field of cancer. For example, in the treatment of cancerous tumour growths, particularly solid tumours.

Therapeutic substances of the present invention may be used in the treatment of a human or non-human animal. The treatment may be prophylactic or may be in respect of an existing condition. For example, in the treatment of cancer, including breast cancer, colon cancer, colorectal cancer, esophageal cancer, glioma, lung small and non-small cell cancers, leukaemia neuroblastoma, prostate cancer, thoracic cancer, melanoma, ovarian cancer, cervical cancer and renal cancer; cardiac hypertrophy, as well as haematological disorders including hemoglobinopathies, thalessmia, and sickle cell anemia, auto-immune diseases, such as arthritis, Huntington's disease, and neurological conditions, such as Alzheimer's disease, and genetic-related metabolic disorders, such as cystic fibrosis, peroxisome biogenesis disorders and adrenoleukodystrophy. HDAC inhibitors have been proposed for stimulating hematopoietic cells ex vivo, ameliorating protozoal parasitic infection, accelerating wound healing and protecting hair follicles. Thus the substances of the present invention may be used in the manufacture of a medicament for the treatment of one or more of the above-mentioned diseases/disorders.

A preferred use in accordance with this aspect is the use of a compound of general formula (I) in the manufacture of a medicament for the treatment of cancer.

A compound of the invention may be used in combination with another chemotherapeutic or antineoplastic agent in the treatment of cancer. For example, mitoxantrone, Vinca alkaloids, such as vincristine and vinblastine, anthracycline antibiotics such as daunorubicin and doxorubicin, alkylating agents such as chlorambucil and melphalan, taxanes such as paclitaxel, anti-folates such as methotrexate and tomudex, epipodophyllotoxins such as etoposide, camptothecins such as irinotecan and its active metabolite SN-38 and DNA methylation inhibitors.

The compounds of the present invention may therefore be administered as a kit of parts with a chemotherapeutic or anti-neoplastic agent as defined above as a combined preparation for simultaneous, separate or sequential use in treating cancer. The compound of the invention may be administered together or, if separately, in any order as determined by a physician.

This aspect of the invention therefore extends to a method of treatment of an individual suffering from a disease condition, the method comprising administering to the individual a therapeutically effective amount of a compound of general formula (I).

According to a seventh aspect of the present invention, there is provided a method of inhibition of histone deacetylase activity in an individual suffering from a disease condition, the method comprising administering to the individual a therapeutically effective amount of a compound of general formula (I).

The inhibition may be defined as any reduction in the activity of histone deacetylase activity in the individual. The reduction may be from an elevated level of activity to a normal level in the subject, or it may even be a reduction to below what would be considered as the normal activity in the subject.

Preferred features for the second and subsequent aspects of the invention are as for the first aspect mutatis mutandis.

The invention will now be further described by way of reference to the following Examples which are provided for the purposes of illustration only and are not to be construed as being limiting on the invention.

EXAMPLES

Syntheses of Preferred Compounds

Experimental Section

Starting materials were purchased from Avocado or Aldrich and used as supplied, unless otherwise stated.

(5Acetylamino-1-carbamoyl-pentyl)-carbamic acid tert-butyl ester.

To a solution of triethylamine (0.8 mL, 5.8 mmol) in DMF (35 mL) was added N-acetyl-L-lysine (1.0 g, 5.3 mmol). After 15 minutes, di-tert-butyl dicarbonate (1.27 g, 5.8 mmol) was added to the slurry. After a further sixteen hours, the clear solution was concentrated under reduced pressure to give an oil. Water was added together with enough saturated aqueous sodium hydrogen carbonate to dissolve the oil. The basic solution was washed three times with diethyl ether to remove any unreacted di-tert-butyl dicarbonate. The aqueous solution was then cooled to 0° C. and acidified with concentrated hydrochloric acid (10 M). The oily mixture was extracted three times with ethyl acetate. The residual organic layer was then washed with brine, dried over anhydrous $MgSO_4$, filtered and concentrated under reduced pressure to give the pure title compound as a white powder.

[(S)-5-Acetylamino-1-(4-methyl-2-oxo-2H-chromen-7-ylcarbamoyl)-pentyl]-carbamic acid-tert-butyl ester was prepared as described in: Hoffmann, K.; Brosch, G.; Loidl, P.; Jung, M. Pharmazie, 2000, 55, 601.

Hexa-2,4-dienoic acid methyl ester (3a).

To a solution of sorbic acid (1.12 g, 10 mmol) in dry methanol (50 mL) was added dropwise a solution of trimethylsilyl chloride (2M, 12 mL) in $CH_2Cl_2$. After stirring for 16 hours, the mixture was concentrated under reduced pressure to give a pale yellow oil that was purified by flash chromatography (9:1 60-80° C. petroleum ether:diethyl ether) to give the title compound (1.23 g, 99%) as a colourless oil.

6-Bromohexa-2,4-dienoic acid methyl ester (4a).

A mixture of methyl sorbate (1.26 g, 10 mmol) and N-bromosuccinimide (1.98 g, 11.0 mmol) in chlorobenzene was irradiated with a 250 W sunlamp so as to achieve a state of reflux for 4 hours. The (cooled) mixture was then evaporated under reduced pressure to give a brown oil which was purified by column chromatography (9:1 60-80° C. petroleum ether: diethyl ether) to give the title compound (1.33 g, 65%) as a clear oil.

6-Phenylsulfanyl-hexa-2,4-dienoic acid (6a).

To a solution of 6-phenylsulfanyl-hexa-2,4-dienoic acid methyl ester (0.34 g, 1.45 mmol) in methanol (5 mL) were added aqueous sodium hydroxide (1M, 5 mL, 5 mmol) and distilled water (20 mL). The stirred mixture was heated at reflux for 1 hour, allowed to cool to 20° C., and then concentrated under reduced pressure to about 10 mL. The aqueous solution was washed with diethyl ether (50 mL) and then poured onto a mixture of ethyl acetate (50 mL) and hydrochloric acid (2M, 10 mL) at 0° C. The mixture was shaken, the organic layer was separated and washed successively with saturated aqueous sodium hydrogen carbonate (25 mL), distilled water (25 mL), and brine (25 mL), then dried over anhydrous $MgSO_4$, filtered and concentrated under reduced pressure to give a pale yellow solid that was recrystallised from diethyl ether/hexanes to give the title compound (0.30 g, 93%) as a white solid, mp 108-110° C.

6-(4-Chlorophenylsulfanyl)-hexa-2,4-dienoic acid methyl ester (6b).

To a solution of 6-bromohexa-2,4-dienoic acid methyl ester (1.03 g, 5 mmol), triethylamine (1.4 mL, 10 mmol) and tert-butylammonium iodide (92 mg, 0.25 mmol) in freshly distilled THF (25 mL) was added 4-chlorothiophenol under an atmosphere of nitrogen. The mixture was stirred at reflux for 2 hours after which it was concentrated under reduced pressure. The oil was dissolved in, ethyl acetate (100 mL) and then washed successively with saturated aqueous sodium hydrogen carbonate (50 mL), distilled water (50 mL) and brine (50 mL). The organic layer was then dried over anhydrous $MgSO_4$, filtered and concentrated under reduced pressure to give an oil that was purified by flash chromatography (1:9 diethyl ether:40-60° C. petroleum ether). The resulting yellow solid was recrystallised from diethyl ether/40-60° C. petroleum ether to give the title compound (0.85 g, 63%) as a white solid, mp 75-77° C.

6-Phenylsulfanyl-hexa-2,4-dienoic acid methyl ester (6c).

To a solution of 6-bromohexa-2,4-dienoic acid methyl ester (0.57 g, 2.8 mmol) and thiophenol (0.28 mL, 2.8 mmol) was added triethylamine (0.43 mL, 3.1 mmol), dropwise, under an atmosphere of nitrogen. The mixture was stirred at 20° C. for one hour. The slurry was then filtered and the filtrate was washed with aqueous sodium hydroxide (1 M) then with brine. The organic layer was dried over anhydrous $MgSO_4$, filtered and concentrated under reduced pressure. The residue was subjected to column chromatography (9:1 60-80° C. petroleum ether:diethyl ether) to give the title compound (0.93 g, 88%) as a clear oil.

6-(4-Dimethylamino-phenylsulfanyl)-hexa-2,4-dienoic acid methyl ester (6d).

To a solution of 6-bromo-hexa-2,4-dienoic acid methyl ester (1.15 g, 5.6 mmol) and 4-dimethylamino-benzenethiol (0.86 g, 5.6 mmol) in tetrahydrofuran (30 mL) was added dropwise triethylamine (1.6 mL, 11.4 mmol) under an atmosphere of argon. The mixture was stirred at 20° C. for 30 minutes, then filtered. The filtrate was concentrated under reduced pressure and the residue was dissolved in ethyl acetate (100 mL). This solution was washed with saturated aqueous sodium hydrogen carbonate (50 mL), demineralised water (50 mL) and brine (50 mL). The organic layer was dried over anhydrous $MgSO_4$, filtered and concentrated under reduced pressure to give a yellow oil that was purified by column chromatography (9:1 to 7:3 60-80° C. petroleum ether:diethyl ether, all eluant containing 1% triethylamine by volume). The solid was recrystallised from diethyl ether/ petroleum ether to give the title compound (1.0 g, 64%) as a white solid, mp 68-70° C.

6-(4-Methoxy-phenylsulfanyl)-hexa-2,4-dienoic acid methyl ester (6e).

To a solution of 6-bromo-hexa-2,4-dienoic acid methyl ester (1.50 g, 7.3 mmol) and 4-methoxythiophenol (0.93 mL, 7.3 mmol) in tetrahydrofuran (40 mL) was added dropwise triethylamine (1.1 mL, 8.0 mmol) under an atmosphere of argon. The mixture was stirred at 20° C. for one hour, then filtered. The filtrate was concentrated under reduced to pressure and the residue was dissolved in ethyl acetate (50 mL). This solution was washed with saturated aqueous sodium hydrogen carbonate (25 mL), demineralised water (25 mL) and brine (25 mL). The organic layer was dried over anhydrous $MgSO_4$, filtered and concentrated under reduced pressure to give a yellow oil that was purified by column chromatography ((9:1 to 8:2 40-60° C. petroleum ether:diethyl ether) to give the title compound as a colourless oil (1.6 g, 86%).

6-(4-Chlorophenylsulfanyl)-hexa-2,4-dienoic acid hydroxyamide (7b).

To a solution of the 6-(4-chlorophenylsulfanyl)-hexa-2,4-dienoic acid methyl ester (0.44 g, 1.64 mmol) in distilled THF (9.0 mL) containing 50% aqueous hydroxylamine (1.0 ml, 15.2 mmol) was added at 0° C. a solution of potassium hydroxide in methanol (1M, 2.6 mL, 2.6 mmol) over a period of 30 minutes. After stirring at 0° C. for 1 h, distilled water (9.0 mL) was added and the mixture was made neutral by dropwise addition of concentrated hydrochloric acid (10 M) at 0° C. The aqueous solution was extracted with ethyl acetate (3×30 mL) and the combined extracts were dried over anhydrous $MgSO_4$, and evaporated to dryness. The residue was recrystallised from acetone to give the title compound (0.21 g, 48%) as a pale brown powder, mp 120-122° C. (decomp).

6-(4-Dimethylamino-phenylsulfanyl)-hexa-2,4-dienoic acid hydroxyamide (7c).

To a solution of 6-(4-dimethylamino-phenylsulfanyl)-hexa-2,4-dienoic acid methyl ester (0.556 g, 2.0 mmol) in distilled THF (10 mL) containing aqueous hydroxylamine (50%, 1.21 mL, 18.4 mmol) was added at 0° C. a solution of potassium hydroxide in methanol (1M, 2.8 mL, 2.8 mmol) over a period of 30 minutes. After stirring the mixture at 0° C. for an additional hour, distilled water (10 mL) was added and the mixture was made neutral by dropwise addition of concentrated hydrochloric acid (10 M) at 0° C. The solution was then extracted with ethyl acetate (2×50 mL), and the combined extracts were dried over anhydrous $MgSO_4$, and evaporated to dryness. The solid residue was recrystallised from ethyl acetate to give the title compound (0.24 g, 43%) as a white solid.

6-Benzenesulfinyl-hexa-2,4-dienoic acid methyl ester (8a).

To a solution of 6-phenylsulfanyl-hexa-2,4-dienoic acid methyl ester (0.336 g, 1.43 mmol) in methanol (17 mL) was added dropwise at 0° C. a solution of sodium metaperiodate (0.37 g, 1.72 mmol) in distilled water (6 mL). The mixture was allowed to warm to 20° C. and then heated at reflux for 5 hours. The solution was concentrated under reduced pressure to give an oil that was dissolved in ethyl acetate (20 mL). The organic layer was washed with saturated aqueous sodium hydrogen carbonate (10 mL), distilled water (10 mL) and then brine. The organic layer was dried over anhydrous $MgSO_4$, filtered and concentrated under reduced pressure to give an oil that was purified by flash chromatography (1:2 to 1:1 to 2:1 ethyl acetate:60-80 ° C. petroleum ether). The resulting powder was recrystallised from diethyl ether to give the title compound (0.29 g, 81%) as a white solid, mp 82-84° C.

6-(4-Chloro-benzenesulfinyl)-hexa-2,4-dienoic acid methyl ester (8b).

To a solution of 6-(4-chlorophenylsulfanyl)-hexa-2,4-dienoic acid methyl ester (0.396 g, 1.47 mmol) in methanol (20 mL) was added dropwise at 0° C. a solution of sodium metaperiodate (0.37 g, 1.72 mmol) in distilled water (10 mL). The mixture was allowed to warm to 20° C., then heated at reflux for 5 hours. The solution was concentrated under reduced pressure to give an oil that was dissolved in ethyl acetate (20 mL). The organic layer was washed with saturated aqueous sodium hydrogen carbonate (10 mL), distilled water (10 mL), then with brine. The organic layer was then dried over anhydrous $MgSO_4$, filtered and concentrated under reduced pressure to give an oil that was purified by flash chromatography (2:8 ethyl acetate:40-60° C. petroleum ether). The resulting powder was recrystallised from ethylacetate/40-60° C. petroleum ether to give the title compound (0.32 g, 77%) as a white solid.

6-(4-Methoxybenzenesulfinyl)-hexa-2,4-dienoic acid methyl ester (8c).

To a solution of 6-(4-methoxybenzenesulfanyl)-hexa-2,4-dienoic acid methyl ester (1.0 g, 3.8 mmol) in methanol (8 mL) was added at 0° C. a solution of sodium metaperiodate (0.856 g, 4.0 mmol) in water (8 mL). The mixture was stirred at reflux for 1 h, allowed to cool to 20° C. then extracted with ethyl acetate (3×50 mL). The combined extracts were washed with saturated aqueous sodium hydrogen carbonate (25 mL), distilled water (25 mL) and brine (25 mL), dried over anhydrous $MgSO_4$, and evaporated to dryness. The residue was purified by column chromatography (1:1 to 8:2 ethyl acetate: 40-60° C. petroleum ether) to give the title compound (0.92 g, 87%) as a pale yellow oil.

6-Benzenesulfinyl-hexa-2,4-dienoic acid (8d).

To a solution of 6-benzenesulfinyl-hexa-2,4-dienoic acid methyl ester (0.243 g, 0.97 mmol) in methanol (2.0 mL) were added a solution of aqueous sodium hydroxide (1M. 4.0 mL, 4 mmol) and distilled water (10 mL). After stirring at reflux for one hour, the mixture was allowed to cool to 20° C. and was concentrated under reduced pressure. The solution was washed with diethyl ether (25 mL) and then poured onto a mixture of ethyl acetate (20 mL) and hydrochloric acid (2M, 5 mL) at 0° C. The mixture was shaken, and the organic layer separated and washed successively with saturated aqueous sodium hydrogen carbonate (10 mL), distilled water (10 mL), brine (10 mL), then dried over anhydrous $MgSO_4$, filtered and concentrated under reduced pressure to give a pale yellow solid that was recrystallised from ether/hexanes to give the title compound (0.204 g, 89%) as a white solid.

6-(4-Chlorobenzenesulfinyl)-hexa-2,4-dienoic acid hydroxyamide (9a).

To a solution of the 6-(4-chlorobenzenesulfinyl)-hexa-2,4-dienoic acid methyl ester (0.80 g, 2.79 mmol) in distilled THF (15 mL) containing an aqueous solution of hydroxylamine (50%/o, 1.7 ml, 25.8 mmol) was added at 0° C. a solution of potassium hydroxide in methanol (1M, 4.5 ml, 4.5 mmol) over a period of 30 minutes. After stirring at 0° C. for 1 hour, distilled water (15 mL) was added and the mixture was made neutral by dropwise addition of concentrated hydrochloric acid (10 M) at 0° C. The aqueous solution was extracted with ethyl acetate (3×50 mL) and the combined extracts were dried over anhydrous $MgSO_4$, and evaporated to dryness. The residue was recrystallised from acetone to give the title compound (0.45 g, 56%) as a pale brown powder, mp 159° C. (decomp).

6-(4-Methoxybenzenesulfinyl)-hexa-2,4-dienoic acid hydroxyamide (9b).

To a solution of 6-(4-methoxybenzenesulfinyl)-hexa-2,4-dienoic acid methyl ester (0.32 g, 1.14 mmol) in distilled THF (6 mL) containing an aqueous solution of hydroxylamine (50%, 0.7 ml, 10.6 mmol) was added at 0° C. a solution of potassium hydroxide in methanol (1M, 1.8 ml, 1.8 mmol) over a period of 30 minutes. After stirring at 0° C. for 1 hour, distilled water (6 mL) was added and the mixture was made neutral by dropwise addition of concentrated hydrochloric acid (10 M) at 0° C. The aqueous solution was extracted with ethyl acetate (3×20 mL) and the combined extracts were dried over anhydrous $MgSO_4$, and evaporated to dryness. The residue was recrystallised from acetone to give the title compound (0.11 g, 34%) as a pale brown powder, mp 145-147° C. (decomp).

6-Benzenesulfonyl-hexa-2,4-dienoic acid (10a).

To a solution of the 6-benzenesulfonyl-hexa-2,4-dienoic acid methyl ester (0.70 g, 2.60 mmol) in methanol (8 mL) were added a aqueous sodium hydroxide 1M, 6.0 mL, 6 mmol) and distilled water (20 mL). After stirring at reflux for 1 hour, the mixture was allowed to cool to 20° C. and was concentrated under reduced pressure. The aqueous solution was washed with diethyl ether (50 mL) and then poured onto a mixture of ethyl acetate (50 mL) and hydrochloric acid (2M, 5 mL) at 0° C. The organic layer was washed successively with saturated aqueous sodium hydrogen carbonate (20 mL), distilled water (20 mL), and brine (20 mL), then dried over anhydrous $MgSO_4$, filtered and concentrated under reduced pressure to give a pale yellow solid that was recrystallised from ethyl acetate to give the title compound (0.58 g, 87%) as a white solid, mp 148-150° C.

6-Benzenesulfonyl-hexa-2,4-dienoic acid methyl ester (10b).

A mixture of 6-bromohexa-2,4-dienoic acid methyl ester (0.41 g, 2.0 mmol), sodium benzene sulfinate (0.33 g, 2.0 mmol) and tetra-n-butylammonium iodide (37 mg, 0.1 mmol) was heated at reflux in dry THF (10 mL) under an atmosphere of nitrogen for 2 hours. The resulting slurry was allowed to cool to 20° C. and filtered. The filtrate was concentrated under reduced pressure to give an oil that was dissolved in ethyl acetate (20 mL). This solution was washed successively with saturated aqueous sodium hydrogen carbonate (10 mL), distilled water (10 mL), then with brine (10 mL). The organic layer was dried over anhydrous $MgSO_4$, filtered and concentrated under reduced pressure to give an oil that was purified by flash chromatography (7:3 to 1:1 to 1:1 60-80° C. petroleum ether:diethyl ether) to give a solid that was recrystallised to give the title compound (0.39 g, 73%) as white crystals, mp 105° C.

6-Benzenesulfonyl-hexa-2,4-dienoic acid hydroxyamide (11a).

To a solution of 6-benzenesulfonyl-hexa-2,4-dienoic acid (0.292 g, 1.15 mmol) in dry dichloromethane (5 mL) was added dropwise oxalyl chloride, at 0° C. under an atmosphere of argon. One drop on dimethylformamide was then added. After stirring at 2020 C. for one hour, a solution of aqueous hydroxylamine (50%, 0.17 mL, 2.5 mmol) in tetrahydrofuran (5 mL) was added. The mixture was stirred for an additional hour and concentrated under reduced pressure to give a yellow foam that was purified by column chromatography (8:2 ethyl acetate:40-60° C. petroleum to 100% ethyl acetate). The title compound (91 mg, 31%) was obtained as a white foam.

6-(Naphthalen-2-ylsulfanyl)-hexa-2,4-dienoic acid methyl ester (13b).

To a solution of 6-bromo-hexa-2,4-dienoic acid methyl ester (1.57 g, 7.66 mmol) and 2-thionaphthol (1.35 g, 8.42 mmol) in diethyl ether (40 mL) was added dropwise triethylamine (1.40 mL, 10.0 mmol) under an atmosphere of argon. The mixture was stirred for one hour 20° C. and filtered. The filtrate was washed saturated aqueous sodium hydrogen carbonate (25 mL), demineralised water (25 mL) and brine (25 mL). The organic layer was dried over anhydrous $MgSO_4$, filtered and concentrated under reduced pressure to give a yellow oil that was purified by column chromatography (9:1 to 8:2 40-60° C. petroleum ether:diethyl ether). Recrystallisation from diethyl ether/petroleum ether afforded the title compound (1.9 g, 88%) as a white solid, mp 73-75° C.

6-(Naphthalen-2-ylsulfanyl)-hexa-2,4-dienoic acid hydroxyamide (14a).

To a solution of 6-(naphthalen-2-ylsulfanyl)-hexa-2,4-dienoic acid methyl ester (0.505 g, 1.78 mmol) in distilled THF (10 mL) containing 50% aqueous hydroxylamine (1.08 mL, 16.4 mmol) was added at 0° C. a solution of potassium hydroxide in methanol (1M, 2.5 ml, 2.5 mmol) over a period of 30 minutes. After stirring the mixture at 0° C. for an additional hour, distilled water (10 mL) was added and the mixture was made neutral by dropwise addition of concentrated hydrochloric acid (10 M) at 0° C. The solution was extracted with ethyl acetate (2×50 mL), and the combined extracts were dried over anhydrous $MgSO_4$, and evaporated to dryness. The solid residue was recrystallised from ethyl acetate to give the title compound (0.315 g, 62%) as a white solid.

2-Methylpent-2-enoic acid methyl ester (16b).

A mixture of 2-methylpent-2-enoic acid (5.0 g, 44 mmol) and sulfuric acid (0.5 mL) in methanol (250 mL) was heated at reflux for 16 hours. The solution was allowed to cool down to 20° C. and concentrated under reduced pressure. The residue was dissolved in ethyl acetate (100 mL) and washed with saturated aqueous sodium hydrogen carbonate (2×50 mL), distilled water (50 mL), then with brine (50 mL). The organic layer was dried over anhydrous $MgSO_4$, filtered and concentrated under reduced pressure to give the title compound (5.1 g, 91%) as a colourless oil.

4-Bromo-2-methylpent-2-enoic acid methyl ester (17b).

A solution of 2-methylpent-2-enoic acid methyl ester (1.20 g, 9.37 mmol) and N-bromosuccinimide (1.83 g, 10.2 mmol) in dry carbon tetrachloride (15 mL) irradiated with a 250 W sunlamp so as to achieve a state of reflux for 2.5 hours. After cooling, the succinimide was filtered off, the carbon tetrachloride was evaporated, and the product was distilled over a short path under reduced pressure to give the title compound (1.60 g, 82%) as a colourless oil.

4(N,N-Dimethylamino)phenyl disulfide (19).

To a stirred solution of 4-aminophenyl disulfide (2.50 g, 10 mmol) in methanol (60 mL) containing 37% aqueous formaldehyde (25 mL, 62.5 mmol) at 20° C. was added a solution of sodium cyanoborohydride (2.60 g, 40 mmol) and zinc chloride (2.74 g, 20 mmol) in methanol (100 mL). After stirring at 20° C. for 2 h, the solution was dissolved in NaOH (0.1 M, 100 mL) and most of the methanol was evaporated under reduced pressure. The aqueous solution was extracted with ethyl acetate (3×200 mL) and the combined extracts were washed with water then with brine, dried over anhydrous $MgSO_4$, and evaporated to dryness. The residue was recrystallised from methanol to a give the title compound (2.48 g, 81%) as a yellow solid.

4-Dimethylamino-benzenethiol (20).

To a stirred solution of 4-(N,N-dimethylamino)phenyl disulfide (0.855 g, 2.81 mmol) in a mixture of dioxane (10 mL) and demineralised water (2.5 mL) at 20° C. was added tri-n-butylphosphine (0.75 mL, 2.89 mmol). After stirring at 20° C. for 30 minutes, the mixture was concentrated under reduced pressure. The residue was dried by co-evaporation with toluene (3×10 mL) to afford a clear oil containing the title compound (2.81 mmol) which was used without any further purification.

4-(4-Dimethylaminophenylsulfanyl)-2-methylpent-2-enoic acid methyl ester (21b).

To a solution of 4-bromo-2-methylpent-2-enoic acid methyl ester (0.414 g, 2.0 mmol) in dry benzene (4 mL) under an atmosphere of argon was added a solution of triethylamine (0.28 mL, 2.0 mmol) and 4-dimethylamino-benzenethiol (0.306 g, 2.0 mmol) in dry benzene (2 mL). The mixture was stirred at 20° C. for 2 hours (TLC monitoring). The solvent was then removed under reduced pressure to give a yellow oil that was purified by column chromatography (20:79:1 diethyl ether:60-80° C. petroleum ether:triethylamine) to give the title compound (0.53 g, 95%) as a colourless oil.

4-(4-Dimethylaminophenylsulfanyl)-2-methylpent-2-en-1-ol (22b).

To a solution of 4-(4-dimethylaminophenylsulfanyl)-2-methylpent-2-enoic acid methyl ester (0.279 g, 1.0 mmol) in dry THF (4 mL) at 0° C. was added dropwise a solution of di-isobutylaluminium hydride in toluene (1M, 3.0 mL, 3.0 mmol), under an atmosphere of argon. After stirring at 0° C. for one hour (TLC monitoring), the mixture was quenched by addition of methanol (0.5 mL: CAUTION), then water (0.3 mL), 5% aqueous sodium hydroxide solution (0.3 mL) and lastly 30% aqueous sodium potassium tartrate (4 mL). The mixture was stirred for 2 hours at 20° C., then extracted with diethyl ether (3×10 mL). The combined organic layers were dried over anhydrous $MgSO_4$, filtered and evaporated to give the title compound (0.22 g, 88%) as a colourless oil.

6-(4-Dimethylaminophenylsulfanyl)-4-methylhepta-2,4-dienoic acid ethyl ester (24c).

To a solution of 4-(4-dimethylamino-phenylsulfanyl)-2-methylpent-2-en-1-ol (0.739 g, 2.94 mmol) and triethylamine (3.8 mL, 27.1 mmol) in dimethyl sulfoxide (10 mL) was added sulfur trioxide-pyridine complex 50% (2.76 mg, 8.68 mmol) in dimethyl sulfoxide (10 mL). The mixture was stirred at 20° C. for 10 minutes (TLC monitoring) and ice-water (50 mL) was added. The mixture was extracted with diethyl ether (50 mL). The ethereal layer was washed with water (3×25 mL) then with brine (25 mL), dried over anhydrous $MgSO_4$, filtered and concentrated under reduced pressure. The resulting yellow oil was dissolved in dichloromethane (15 mL) and (triphenylphosphanylidene)-acetic acid ethyl ester was added in one portion. The mixture was gently heated at reflux for 24 h under an atmosphere of argon. The solvent was removed under reduced pressure and the crude material was purified by column chromatography (10:89:1 diethyl ether:40-60° C. petroleum ether:triethylamine) to give the title compound (0.71 g, 76%) as a colourless oil.

6-(4-Dimethylamino-phenylsulfanyl)-4-methylhepta-2,4-dienoic acid hydroxyamide (25c).

To a solution of 6-(4-dimethylaminophenylsulfanyl)-4-methylhepta-2,4-dienoic acid ethyl ester (0.576 g, 1.80 mmol) in dry THF (10 mL) was added at 0° C. an aqueous solution of hydroxylamine (50%, 1.1 mL, 16.6 mmol). To this mixture was added a solution of potassium hydroxide in methanol (1M, 2.9 mL, 2.9 mmol) over a period of 40 minutes at 0° C. The mixture was stirred at 20° C. for 16 hours, and water (10 mL) was then added. The solution was acidified to pH 5 by addition of concentrated hydrochloric acid (10 M, CAUTION), then extracted with ethyl acetate (50 mL). The organic layer was washed with brine (25 mL), dried over anhydrous $MgSO_4$, filtered and concentrated under reduced pressure. The yellow oil was dissolved in a mixture of 1:1 diethyl ether:methanol (20 mL) and 20 drops of concentrated hydrochloric (10 M) were added. The crude mixture was evaporated to dryness to give an oil that was triturated with a mixture of diethyl ether and ethanol to give the title compound (0.34 g, 52%) as an off-white solid, mp 177-178° C. (decomp).

6-Bromohexanoic acid methyl ester (27a).

To a solution of acetyl chloride (1.0 mL, 14 mmol) in methanol (150 mL) at 0° C. was added a solution of 6-bromohexanoic acid (10.0 g, 51 mmol) in methanol (50 mL). The mixture was heated at reflux for 2 hours, then allowed to cool down to room temperature and concentrated under reduced pressure. The residue was dissolved in ethyl acetate (150 mL) and washed consecutively with saturated aqueous sodium hydrogen carbonate (2×50 mL), distilled water (50 mL), and brine (50 mL). The organic layer was dried over anhydrous $MgSO_4$, filtered and concentrated under reduced pressure to give the title compound (10.3 g, 96%) as a colourless oil.

6(4-Chloro-phenylsulfanyl)-hexanoic acid methyl ester (28b).

To a solution of 6-bromohexanoic acid methyl ester (2.1 g, 10 mmol), triethylamine (1.6 mL, 11 mmol) and tert-butylammonium iodide (200 mg, 0.54 mmol) in freshly distilled THF (30 mL) was added 4-chlorothiophenol (1.45 g, 10 mmol) under an atmosphere of argon. The mixture was stirred at reflux for 2 hours after which it was concentrated under reduced pressure. The oil was dissolved in ethyl acetate (100 mL) and then washed successively with saturated aqueous sodium hydrogen carbonate (50 mL), distilled water (50 mL) and brine (50 mL). The organic layer was then dried over anhydrous $MgSO_4$, filtered and concentrated under reduced pressure to give an yellow oil that was purified by flash chromatography (1:9 diethyl ether:40-60° C. petroleum ether). The title compound was obtained as a colourless oil (2.5 g, 93%).

7-(4-Chloro-phenylsulfanyl)-heptanoic acid ethyl ester (28c).

To a solution of 7-bromoheptanoic acid ethyl ester (2.5 mL, 12.8 mmol) and triethylamine (2 mL, 14.3 mmol) in dichloromethane (10 mL) was added 4-chlorothiophenol (1.86 g, 12.8 mmol) under an atmosphere of argon. The mixture was stirred at reflux for 2 hours after which it was concentrated under reduced pressure. The oil was dissolved in ethyl acetate (50 mL) and then washed successively with saturated aqueous sodium hydrogen carbonate (25 mL), distilled water (25 mL) and brine (25 mL). The organic layer was then dried over anhydrous $MgSO_4$, filtered and concentrated under reduced pressure to give an yellow oil that was purified by flash chromatography (1:9 diethyl ether:40-60° C. petroleum ether). The title compound was obtained as a colourless oil (3.3 g, 87%).

6-(4-Amino-phenylsulfanyl)-hexanoic acid methyl ester (28d).

To a solution of 4-aminothiophenol (2.4 g, 18.9 mmol) in methanol (10 mL) was added triethylamine (2.70 mL, 19.2 mmol). A solution of 6-bromohexanoic acid methyl ester (3.0 g, 18.9 mmol) and tert-butylammonium iodide (350 mg, 0.95 mmol) in methanol (5 mL) was added. The mixture was stirred at room temperature for 16 hours and then concentrated under reduced pressure. The residue was taken up in ethyl acetate (100 mL) and water (100 mL). The organic layer was washed with saturated aqueous sodium hydrogen carbonate (100 mL), distilled water (100 mL) and brine (100 mL), dried over anhydrous $MgSO_4$, filtered and concentrated under reduced pressure to give a yellow oil that was purified by flash chromatography (2:8 to 1:1 ethyl acetate:40-60° C. petroleum ether) to give the title compound (3.0 g, 62%) as a colourless oil.

6-(4-Dimethylamino-phenylsulfanyl)-hexanoic acid methyl ester (28e).

To a solution of 6-(4-amino-phenylsulfanyl)-hexanoic acid methyl ester (2.5 g, 10 mmol) in methanol (20 mL) was added at 0° C. a 37% aqueous solution of formaldehyde (2.4 mL, 30 mmol) and a solution of sodium cyanoborohydride (2.5 g, 40 mmol) and zinc chloride (2.7 g, 20 mmol) in methanol (150 mL). The mixture was stirred at room temperature for 2 hours and concentrated under reduced pressure. The residue was taken up in ethyl acetate (250 mL) and aqueous sodium hydroxide (100 mL, 2M). The organic layer was washed consecutively with aqueous sodium hydroxide (100 mL, 2M), distilled water (2×100 mL) and brine (2×100 mL), dried over anhydrous $MgSO_4$, filtered and concentrated under reduced pressure to give a yellow oil that was purified by flash chromatography (10:90:1 to 20:80:1 ethyl acetate:40-60° C. petroleum ether:triethylamine) to give the title compound (2.2 g, 79%) as a colourless oil.

6-(4-((4-Chlorobenzyl)-methylamino)-phenylsulfanyl)-hexanoic acid methyl ester (28f).

To a solution of 6-(4-amino-phenylsulfanyl)-hexanoic acid methyl ester (1.5 g, 5.9 mmol) in methanol (60 mL) was added a solution of 4-chlorobenzaldehyde (834 mg, 5.9 mmol) in methanol (10 mL). After 1 hour of stirring at room temperature, the solution was cooled at 0° C. and a 37% aqueous solution of formaldehyde (1.44 g, 17.8 mmol) was added. A solution of sodium cyanoborohydride (1.49 g, 23.7 mmol) and zinc chloride (11.9 mmol) in methanol (60 mL) was added in a dropwise. The resulting mixture was stirred at room temperature for 1 hour and concentrated under reduced pressure. The residue was taken up in ethyl acetate (100 mL) and aqueous sodium hydroxide (75 mL, 2M). The organic layer was washed consecutively with aqueous sodium hydroxide (75 mL, 2M), distilled water (2×75 mL) and brine (75 mL), dried over anhydrous $MgSO_4$, filtered and concentrated under reduced pressure to give an yellow oil that was purified by flash chromatography (5:95:1 to 20:80:1 ethyl acetate:40-60° C. petroleum ether:triethylamine). The title compound was obtained as a colourless oil (2.2 g, 83%).

6-(4-(4-Chlorobenzenesulfonylamino)-phenylsulfanyl)-hexanoic acid methyl ester (28g).

To a solution of 6-4-amino-phenylsulfanyl)-hexanoic acid methyl ester (950 mg, 3.75 mmol) in dry pyridine (6 mL) was added 4-chlorobenzenesulfonyl chloride (1.0 g, 4.9 mmol). After stirring at room temperature for 1 hour, the solution was concentrated under reduced pressure. The residue was taken up in ethyl acetate (50 mL) and water (25 mL). The organic layer was separated and washed consecutively with hydrochloric acid (3×25 mL, 1M), water (25 mL), and brine (25 mL), dried over anhydrous $MgSO_4$, filtered and evaporated to dryness to give the title compound as a colourless oil (1.25 g, 78%).

6-(4-Bromo-phenylylsulfanyl)-hexanoic acid methyl ester (28h).

To a solution of 6-bromohexanoic acid methyl ester (2.6 g, 12.6 mmol), triethylamine (2.0 mL, 14 mmol) and tert-butylammonium iodide (232 mg, 0.63 mmol) in methanol (10 mL) was added 4-bromothiophenol (2.4 g, 12.6 mmol) under an atmosphere of argon. The mixture was stirred at room temperature for 16 hours after which it was concentrated under reduced pressure. The oil was dissolved in ethyl acetate (40 mL) and then washed with saturated aqueous sodium hydrogen carbonate (2×20 mL), distilled water (2×20 mL) and brine (20 mL). The organic layer was dried over anhydrous $MgSO_4$, filtered and concentrated under reduced pressure to give an yellow oil that was purified by flash chromatography (2:98 to 10:90 ethyl acetate:40-60° C. petroleum ether). The title compound was obtained as a colourless oil (3.5 g, 88%).

6-(4'-Chloro-biphenyl-4-ylsulfanyl)hexanoic acid methyl ester (28i).

To a degassed solution of 6-(4-bromo-phenylsulfanyl)-hexanoic acid methyl ester (500 mg, 1.58 mmol) in ethylene glycol dimethyl ether (20 mL) was added 1,1'-bis(diphenylphosphino)ferrocene-palladium(II)dichloride dichloromethane complex (131 mg, 0.16 mmol). The resulting mixture was stirred for 5 min at room temperature under an argon atmosphere. 4-Chlorophenylboronic acid (494 mg, 3.16 mmol) was added. A solution of cesium carbonate (1.8 g, 5.54 mmol) in water (3 mL) was added. The mixture was stirred at reflux for 1 hour, allowed to cool down to room temperature and concentrated under reduced pressure. The residue was taken up in ethyl acetate (75 mL). This solution was washed with saturated aqueous sodium hydrogen carbonate (2×50 mL), distilled water (2×50 mL) and brine (2×50 mL). The organic layer was dried over anhydrous $MgSO_4$, filtered and concentrated under reduced pressure. The residue was purified by flash chromatography (5:95 to 10:90 diethyl ether:40-60° C. petroleum ether) to give a solid that was recrystallised from diethyl ether/40-60° C. petroleum ether to give the title compound (465 mg, 84%) as a solid, mp 87-88° C.

6-(4-Chloro-phenylsulfanyl)-hexanoic acid hydroxyamide (29b).

To a solution of 6-(4-chlorophenylsulfanyl)-hexanoic acid methyl ester (0.59 g, 2.2 mmol) in distilled THF (13 mL) containing 50% aqueous hydroxylamine (1.3 mL, 19.6 mmol) was added at 0° C. a solution of potassium hydroxide in methanol (1M, 3.5 mL, 3.5 mmol) in a dropwise manner. After stirring at 0° C. for 1 h, distilled water (13 mL) was added and the mixture was made neutral by dropwise addition of concentrated hydrochloric acid (10 M) at 0° C. The aqueous solution was extracted with ethyl acetate (2×25 mL) and the combined extracts were washed with brine (20 mL), dried over anhydrous $MgSO_4$, filtered and evaporated to dryness. The residue was recrystallised from acetone to give the title compound (0.54 g, 90%) as a white powder, mp 83-85° C.

6-(4Dimethylamino-phenylsulfanyl)hexanoic acid hydroxamide (29c).

To a solution of 6-(4-dimethylamino-phenylsulfanyl)-hexanoic acid methyl ester (722 mg, 2.6 mmol) in distilled THF (20 mL) containing 50% aqueous hydroxylamine (1.7 mL, 25.7 mmol) was added at 0° C. a solution of potassium hydroxide in methanol (1M, 4.4 mL, 4.4 mmol) in a dropwise manner. After stirring at 0° C. for 1 h, distilled water (20 mL) was added and the mixture was made neutral by dropwise addition of concentrated hydrochloric acid (10 M) at 0° C. The aqueous solution was extracted with ethyl acetate (2×40 mL) and the combined extracts were washed with brine (80 mL), dried over anhydrous $MgSO_4$, filtered and evaporated to dryness. The title compound was obtained as a colourless oil (377 mg, 52%).

6-(4-(4-Chlorobenzenesulfonylamino)phenylsulfanyl)-hexanoic acid hydroxamide (29g).

To a solution of the 6-(4-(4-chlorobenzenesulfonylamino)-phenylsulfanyl)-hexanoic acid methyl ester (300 mg, 0.7 mmol) in distilled THF (10 mL) containing 50% aqueous hydroxylamine (0.4 mL, 6.3 mmol) was added at 0° C. a solution of potassium hydroxide in methanol (1.2 mL, 1M, 1.2 mmol) in a dropwise manner. After stirring at 0° C. for 1 h, distilled water (10 mL) was added and the mixture was made neutral by dropwise addition of concentrated hydrochloric acid (10 M) at 0° C. The aqueous solution was extracted with ethyl acetate (2×15 mL) and the combined extracts were washed with brine (15 mL), dried over anhydrous $MgSO_4$, filtered and evaporated to dryness. The solid residue was recrystallised from ethyl acetate/diethyl ether to give the title compound (200 mg, 66%) as a white powder, mp 160-163° C.

6-(4'-Chloro-biphenyl-4-ylsulfanyl)-hexanoic acid hydroxamide (29i).

To a solution of 6-(4'-chloro-biphenyl-4-ylsulfanyl)-hexanoic acid methyl ester (1.0 g, 2.9 mmol) in distilled THF (20 mL) containing 50% aqueous hydroxylamine (1.9 mL, 28.8 mmol) was added at 0° C. a solution of potassium hydroxide in methanol (5.0 mL, 1M, 5.0 mmol) in a dropwise manner. After stirring at 0° C. for 1 h, distilled water (20 mL) was added and the mixture was made neutral by dropwise addition of concentrated hydrochloric acid (10 M) at 0° C. The aqueous solution was extracted with ethyl acetate (2×40 mL) and the combined extracts were washed with brine (80 mL), dried over anhydrous $MgSO_4$, filtered and evaporated to dryness. The residue was recrystallised from acetone to give the title compound (923 mg, 91%) as a white powder, mp 156-157° C.

6-(4-Chloro-benzenesulfinyl)-hexanoic acid methyl ester (30b).

To a solution of 6-(4-chlorophenylsulfanyl)-hexanoic acid methyl ester (2.5 g, 9.2 mmol) in methanol (100 mL) was added dropwise at 0° C. a solution of sodium metaperiodate (2.6 g, 12 mmol) in distilled water (30 mL). The mixture was heated at 60° C. for 1 hour. The solution was concentrated under reduced pressure to give an oil that was dissolved in ethyl acetate (100 mL). The organic layer was washed with saturated aqueous sodium hydrogen carbonate (50 mL), distilled water (50 mL), then with brine (50 mL). The organic layer was then dried over anhydrous $MgSO_4$, filtered and concentrated under reduced pressure to give an oil that was purified by flash chromatography (1:1 to 8:2 ethyl acetate:40-60° C. petroleum ether). The title compound was obtained as a colourless oil (2.0 g, 76%).

7-(4-Chloro-benzenesulfinyl)-heptanoic acid ethyl ester (30c).

To a solution of 7-(4-chlorophenylsulfanyl)-heptanoic acid ethyl ester (1.6 g, 5.3 mmol) in ethanol (10 mL) and tetrahydrofuran (10 mL) was added dropwise at 0° C. a solution of sodium metaperiodate (1.1 g, 5.3 mmol) in distilled water (10 mL). The mixture was heated at reflux for 1 hour. The solution was concentrated under reduced pressure to give an oil that was dissolved in ethyl acetate (100 mL). The organic layer was washed with saturated aqueous sodium hydrogen carbonate (50 mL), distilled water (50 mL), then with brine (50 mL). The organic layer was then dried over anhydrous MgSO$_4$, filtered and concentrated under reduced pressure to give an oil that was purified by flash chromatography (1:1 ethyl acetate:40-60° C. petroleum ether). The title compound was obtained as a colourless oil (1.2 g, 74%).

6-(4-Dimethylamino-benzenesulfinyl)-hexanoic acid methyl ester (30e).

To a solution of 6-(4-dimethylamino-phenylsulfanyl)-hexanoic acid methyl ester (1.4 g, 5.0 mmol) in methanol (60 mL) was added dropwise at 0° C. a solution of sodium metaperiodate (1.3 g, 6.0 mmol) in distilled water (20 mL). The mixture was heated at 60° C. for 1 hour. The solution was concentrated under reduced pressure to give an oil that was dissolved in ethyl acetate (150 mL). The organic layer was washed with saturated aqueous sodium hydrogen carbonate (100 mL), distilled water (2×50 mL), and lastly with brine (2×50 mL). The organic layer was dried over anhydrous MgSO$_4$, filtered and concentrated under reduced pressure to give an oil that was purified by flash chromatography (100:1 ethyl acetate:triethylamine) to give the title compound (1.2 g, 81%) as a colourless oil.

6-(4-((4-Chlorobenzyl)-methylamino)-benzenesulfinyl)-hexanoic acid methyl ester (30f).

To a solution of 6-(4-((4-chlorobenzyl)-methylamino)-phenylsulfanyl)-hexanoic acid methyl ester (840 mg, 2.1 mmol) in methanol (60 mL) and tetrahydrofuran (30 mL) was added dropwise at 0° C. a solution of sodium metaperiodate (504 mg, 2.3 mmol) in distilled water (20 mL). The mixture was heated at reflux for 1 hour. The solution was concentrated under reduced pressure to give an oil that was dissolved in ethyl acetate (75 mL). The organic layer was washed with saturated aqueous sodium hydrogen carbonate (50 mL), distilled water (50 mL), and brine (50 mL). The organic layer was dried over anhydrous MgSO$_4$, filtered and concentrated under reduced pressure to give an oil that was purified by flash chromatography (50:50:1 ethyl acetate:40-60° C. ether:triethylamine). The title compound was obtained as a colourless oil (759 mg, 87%).

6-(4'-Chloro-biphenyl-4-ylsulfinyl)-hexanoic acid methyl ester (30i).

To a solution of 6-(4'-chloro-biphenyl-4-ylsulfanyl)-hexanoic acid methyl ester (900 mg, 2.6 mmol) in methanol (30 mL) and tetrahydrofuran (20 mL) was added dropwise at 0° C. a solution of sodium metaperiodate (608 mg, 2.8 mmol) in distilled water (8 mL). The mixture was heated at 60° C. for 2 hours. The solution was concentrated under reduced pressure to give an oil that was dissolved in ethyl acetate (50 mL). The organic layer was washed with saturated aqueous sodium hydrogen carbonate (50 mL), distilled water (50 mL), then with brine (50 mL). The organic layer was dried over anhydrous MgSO$_4$, filtered and concentrated under reduced pressure to give an oil that was purified by flash chromatography (1:1 to 8:2 ethyl acetate:40-60° C. petroleum ether). The solid obtained was recrystallised from diethyl ether/40-60° C. petroleum ether to give the title compound (763 mg, 81%) as a solid, mp 64-65° C.

6-(4-Chloro-benzenesulfinyl)-hexanoic acid hydroxyamide (31a).

To a solution of 6-(4-chloro-benzenesulfinyl)-hexanoic acid methyl ester (2.0 g, 7 mmol) in distilled THF (40 mL) containing 50% aqueous hydroxylamine (4.1 mL, 62 mmol) was added at 0° C. a solution of potassium hydroxide in methanol (12 mL, 1M, 12 mmol) in a dropwise manner. After stirring at 0° C. for 1 h, distilled water (40 mL) was added and the mixture was made neutral by dropwise addition of concentrated hydrochloric acid (10 M) at 0° C. The aqueous solution was extracted with ethyl acetate (2×50 mL) and the combined extracts were washed with brine (75 mL), dried over anhydrous MgSO$_4$, filtered and evaporated to dryness. The residue was recrystallised from acetone to give the title compound (1.8 g, 89%) as a white powder, mp 125° C.

7-(4-Chloro-benzenesulfinyl)-heptanoic acid hydroxyamide (31c).

To a solution of 7-(4-chloro-benzenesulfinyl)-heptanoic acid ethyl ester (0.5 g, 1.6 mmol) in distilled THF (10 mL) containing 50% aqueous hydroxylamine (0.9 mL, 13.6 mmol) was added at 0° C. a solution of potassium hydroxide in methanol (2.5 mL, 1M, 2.5 mmol) in a dropwise manner. After stirring at 0° C. for 1 h, distilled water (10 mL) was added and the mixture was made neutral by dropwise addition of concentrated hydrochloric acid (10 M) at 0° C. The aqueous solution was extracted with ethyl acetate (2×25 mL) and the combined extracts were washed with brine (25 mL), dried over anhydrous MgSO$_4$, filtered and evaporated to dryness. The residue was recrystallised from ethyl acetate to give the title compound (0.4 g, 83%) as a white powder, mp 103-105° C.

6-(4-Dimethylamino-benzenesulfinyl)-hexanoic acid hydroxyamide (31e).

To a solution of the 6-(4-dimethylamino-benzenesulfinyl)-hexanoic acid methyl ester (1.2 g, 4.0 mmol) in distilled THF (30 mL) containing 50% aqueous hydroxylamine (2.65 mL, 40 mmol) was added at 0° C. a solution of potassium hydroxide in methanol (6.8 mL, 1M, 6.8 mmol) in a dropwise manner. After stirring at 0° C. for 1 h, distilled water (30 mL) was added and the mixture was made neutral by dropwise addition of concentrated hydrochloric acid (10 M) at 0° C. The aqueous solution was extracted with ethyl acetate (3×50 mL) and the combined extracts were washed with brine (100 mL), dried over anhydrous MgSO$_4$, filtered and evaporated to dryness. The solid residue was recrystallised from acetone to give the title compound (728 mg, 61%) as a white powder, mp 95-97° C.

6-(4-((4-Chlorobenzyl)-methylamino)-benzenesulfinyl)-hexanoic acid hydroxamide (31f).

To a solution of the 6-(4-((4-chlorobenzyl)-methylamino)-benzenesulfinyl)-hexanoic acid methyl ester (1.6 g, 4.0 mmol) in distilled THF (25 mL) containing 50% aqueous hydroxylamine (2.6 mL, 40 mmol) was added at 0° C. a solution of potassium hydroxide in methanol (1M, 8 mL, 8 mmol) in a dropwise manner. After stirring at 0° C. for 1 h, distilled water (25 mL) was added and the mixture was made neutral by dropwise addition of concentrated hydrochloric acid (10 M) at 0° C. The aqueous solution was extracted with ethyl acetate (2×50 mL) and the combined extracts were washed with brine (100 mL), dried over anhydrous MgSO$_4$, filtered and evaporated to dryness. The solid residue was recrystallised from acetone/40-60° C. petroleum ether to give the title compound (867 mg, 53%) as a white powder, mp 109-111° C.

6-(4'-Chloro-biphenyl-4-sulfinyl)-hexanoic acid hydroxamide (31i).

To a solution of the 6-(4'-chloro-biphenyl-4sulfinyl)-hexanoic acid methyl ester (400 mg, 1.1 mmol) in distilled THF (10 mL) containing 50% aqueous hydroxylamine (0.65 mL, 9.9 mmol) was added at 0° C. a solution of potassium hydroxide in methanol (1.9 mL, 1M, 1.9 mmol) in a dropwise manner. After stirring at 0° C. for 1 h, distilled water (10 mL) was added and the mixture was made neutral by dropwise addition of concentrated hydrochloric acid (10 M) at 0° C. The aqueous solution was extracted with ethyl acetate (2×20 mL) and the combined extracts were washed with brine (40 mL), dried over anhydrous MgSO$_4$, filtered and evaporated to dryness. The residue was recrystallised from acetone to give the title compound (315 mg, 79%) as a white powder, mp 108-110° C.

5-Nitrobenzo[b]thiophene-2-carboxylic acid ethyl ester (36a).

To a suspension of sodium hydride (60% in mineral oil, 1.3 g, 33.5 mmol) in dimethylformamide (50 mL) was added dropwise ethyl 2-mercaptoacetate (2.95 mL, 27 mmol) at 0° C. under an atmosphere of argon. After stirring at room temperature for 15 minutes, 2-chloro-5-nitrobenzaldehyde was added. The mixture was then stirred at 100° C. for 6 h, cooled to room temperature and poured into hydrochloric acid (250 mL, 1M). The precipitate was filtered off, washed with water (3×50 mL), dried under reduced pressure and recrystallised from ethyl acetate to give the title compound (5.5 g, 82%) as a solid, mp 163° C.

5-Dimethylamino-benzo[b]thiophene-2-carboxylic acid ethyl ester (37a).

A suspension of 5-nitrobenzo[b]thiophene-2-carboxylic acid ethyl ester (2.5 g, 10 mmol) and 10% palladium on carbon (250 mg) in ethanol (100 mL) was stirred at room temperature under an atmosphere of hydrogen for 16 h. The mixture was filtered through a pad of celite which was subsequently washed with dichloromethane (3×50 mL). The combined filtrates were concentrated under reduced pressure to give a colourless oil that was suspended in methanol (25 mL). To this mixture was added a 37% aqueous solution of formaldehyde (2.1 mL, 25.9 mmol). To this mixture was added at 0° C. a solution of sodium cyanoborohydride (2.2 g, 35 mmol) and zinc chloride (2.35 g, 17 mmol) in methanol (140 mL). The mixture was stirred at room temperature for 16 hours then concentrated under reduced pressure. The residue was taken up in ethyl acetate (150 mL) and aqueous solution of sodium hydroxide (100 mL, 2M). The organic layer was washed with aqueous sodium hydroxide (100 mL), distilled water (2×100 mL) and brine (3×50 mL), dried over anhydrous MgSO$_4$, filtered and concentrated under reduced pressure to give an oil that was purified by flash chromatography (20:80:1 diethyl ether:40-60° C. petroleum ether:triethylamine) to give a solid that was recrystallised from ethanol to give the title compound (1.0 g, 60%) as a solid, mp 95-96° C.

5-Dimethylamino-benzo[b]thiophen-2-yl)-methanol (38a).

To a suspension of lithium aluminium hydride (285 mg, 5.3 mmol) in dry tetrahydrofuran (10 mL) at 0° C., under an argon atmosphere, was added a solution of 5-dimethylamino-benzo[b]thiophene-2-carboxylic acid ethyl ester (1.2 g, 4.8 mmol) in dry tetrahydrofuran (20 mL) in a dropwise manner. The mixture was stirred at room temperature for 1 hour and then cooled to 0° C. Acetone (10 mL) was added dropwise and brine (40 mL) to give a slurry that was filtered through a pad of celite which was washed with ethyl acetate (3×50 mL). The organic layer was washed with brine (100 mL), dried over anhydrous MgSO$_4$, filtered and concentrated under reduced pressure to give an oil that was purified by flash chromatography (60:40:1 to 50:50:1 ethyl acetate:40-60° C. petroleum ether:triethylamine) to give a solid that was recrystallised from ethanol to give the title compound as a solid (927 mg, 93%), mp 123-125° C.

5-Dimethylamino-benzo[b]thiophene-2-carboxaldehyde (39a).

To a solution of (5-dimethylamino-benzo[b]thiophen-2-yl)-methanol (790 mg, 3.8 mmol) and triethylamine (4.9 mL, 35.1 mmol) in dimethyl sulfoxide (20 mL) was added a solution of pyridine-sulfur trioxide (1.8 g, 11.2 mmol) in dimethyl sulfoxide (20 mL). The mixture was stirred for 1 hour at room temperature followed by addition of water (50 mL) and ethyl acetate (50 mL). The organic layer was washed with water (3×50 mL) and brine (2×50 mL), dried over anhydrous MgSO$_4$, filtered and concentrated under reduced pressure to give a colourless oil that was purified by flash chromatography (10:90:1 to 50:50:1 ethyl acetate:40-60° C. petroleum ether:triethylamine) to give a solid that was recrystallised from ethanol to give the title compound (743 mg, 95%) as a solid, mp 105-106° C.

(2E,4E)-5-(5-Dimethylamino-benzo[b]thiophen-2-yl)-penta-2,4dienoic acid ethyl ester (41a).

To a mixture of sodium hydride (60% in mineral oil, 128 mg, 3.2 mmol) in ethylene glycol dimethyl ether (4 mL) was added dropwise at 0° C. a solution of triethyl phosphonocrotonate (800 mg, 3.2 mmol) in ethylene glycol dimethyl ether (2 mL). The mixture was stirred at room temperature for 45 min. A solution of 5-dimethylamino-benzo[b]thiophene-2-carboxaldehyde (596 mg, 2.9 mmol) in ethylene glycol dimethyl ether (5 mL) was added in dropwise manner. The mixture was stirred at reflux for 90 min, cooled to room temperature and diluted by addition of ethyl acetate (50 mL). The mixture was washed with water (3×25 mL) and brine (25 mL), dried over anhydrous MgSO$_4$, filtered and concentrated under reduced pressure to give an oil, that was purified by flash chromatography (10:90:1 ethyl acetate:40-60° C. petroleum ether:triethylamine) to give a solid that was recrystallised from ethanol to give the title compound (567 mg, 65%) as a solid, mp 140-142° C.

(2E,4E)-5-(5-Dimethylaminobenzo[b]thiophen-2-yl)-penta-2,4-dienoic acid hydroxamide (42a).

To a solution of (2E,4E)-5-(5-dimethylaminobenzo[b]thiophen-2-yl)-penta-2,4-dienoic acid ethyl ester (540 mg, 1.8 mmol) in dry THF (10 mL) was added at 0° C. an aqueous solution of hydroxylamine (50%, 1.1 mL, 16.6 mmol). To this mixture was added a solution of potassium hydroxide in methanol (2.9 mL, 1M, 2.9 mmol) over a period of 40 minutes at 0° C. The mixture was stirred at 20° C. for 2 hours, and water (10 mL) was then added. The solution was acidified to pH 5 by addition of concentrated hydrochloric acid (10 M, CAUTION), then extracted with ethyl acetate (50 mL). The organic layer was washed with brine (25 mL), dried over anhydrous MgSO$_4$, filtered and concentrated under reduced pressure to give a solid which was recrystallised from ethanol to give the title compound (367 mg, 71%) as an orange solid, mp 195° C. (decomp.).

3-Mercapto-benzoic acid (44a).

To a suspension of 3-(chlorosulfonyl)benzoic acid (22.0 g, 0.10 mol) and zinc powder (87.5 g, 1.3 mol) in benzene (150 mL) was added at 0° C., in a dropwise manner, concentrated hydrochloric acid (150 mL, 10 M). The mixture was heated at reflux, stirred for 1 hour, cooled to room temperature, and filtered through a pad of celite, which was subsequently washed with benzene (3×50 mL). The organic layer was separated and washed with water (100 mL), and brine (100 mL), dried over anhydrous MgSO$_4$, filtered and concentrated under reduced pressure to give a white solid which was recrystallised from aqueous ethanol (9.5 g, 62%) to give the title compound as a solid, mp 147° C.

3-Mercaptobenzoic acid methyl ester (45a).

To a solution of 3-mercaptobenzoic acid (4.8 g, 31 mmol) in methanol (50 mL) at 0° C. was added a solution of hydrochloric acid in methanol (1M, 200 mL, 0.2 mol). The mixture was heated at reflux, stirred for 1 hour and concentrated under reduced pressure. The residue was taken up in ethyl acetate and the solution was washed consecutively with saturated aqueous sodium hydrogen carbonate (100 mL), distilled water (100 mL), and brine (100 mL). The organic layer was dried over anhydrous MgSO$_4$, filtered and concentrated under reduced pressure to give the title compound as a colourless oil.

3-(4-Nitro-phenylsulfanyl)-benzoic acid methyl ester (47a).

To a solution of 3-mercaptobenzoic acid methyl ester (504 mg, 3 mmol) and 1-chloro-4-nitrobenzene (473 mg, 3 mmol) in tetrahydrofuran (4 mL) was added at 0° C., in a dropwise manner, a solution of sodium methoxide in methanol (3.3 mL, 1M). The mixture was heated at reflux for 2 hours with stirring, then cooled to room temperature. Ethyl acetate (25 mL) was added and the mixture was washed consecutively with saturated aqueous sodium hydrogen carbonate (10 mL), distilled water (2×10 mL), and brine (10 mL). The organic layer was dried over anhydrous MgSO$_4$, filtered and concentrated under reduced pressure to give a solid that was recrystallised from ethanol to give the title compound (518 mg, 60%) as a solid, mp 98-100° C.

3-(4-Dimethylamino-phenylsulfanyl)-benzoic acid methyl ester (48a).

To a solution of 3-(4-nitrophenylsulfanyl)-benzoic acid methyl ester (500 mg, 1.73 mmol) in ethyl acetate (20 mL) was added 10% palladium on carbon (50 mg). The mixture was stirred for 16 hours at room temperature under an atmosphere of hydrogen, and then filtered through a pad of celite, which was washed with ethyl acetate (2×10 mL). The filtrate was concentrated under reduced pressure to give a colourless oil (448 mg, 1.73 mmol) that was dissolved in methanol (5 mL). To this solution was added a 37% aqueous solution of formaldehyde (0.8 mL, 10.2 mmol) and the mixture was cooled down to 0° C. To this solution was added a solution of sodium cyanoborohydride (435 mg, 6.9 mmol) and zinc chloride (472 mg, 3.45 mmol) in methanol (15 mL). The mixture was stirred at room temperature for 2 hours then concentrated under reduced pressure. The residue was taken up in ethyl acetate (20 mL) and aqueous sodium hydroxide (15 mL, 2M). The organic layer was washed with aqueous sodium hydroxide (15 mL, 2M), distilled water (10 mL) and brine (2×20 mL), dried over anhydrous MgSO$_4$, filtered and concentrated under reduced pressure to give a white solid that was recrystallised from ethanol to give the title compound (397 mg, 80%) as a solid, mp 88-90° C.

(3-(4Dimethylamino-phenylsulfanyl)-phenyl)-methanol (49a).

To a suspension of lithium aluminium hydride (61 mg, 1.1 mmol) in dry tetrahydrofuran (2 mL) at 0° C., under an argon atmosphere, was added a solution of 3-(4-dimethylamino-phenylsulfanyl)-benzoic acid methyl ester (287 mg, 1.0 mmol) in dry tetrahydrofuran (4 mL) in a dropwise manner. The mixture was stirred at room temperature for 1 hour and then cooled to 0° C. Acetone (2 mL) was added dropwise followed by brine (8 mL) to give a slurry that was filtered through a pad of celite, which was washed with ethyl acetate (3×10 mL). The organic layer was washed with brine (25 mL), dried over anhydrous MgSO$_4$, filtered and concentrated under reduced pressure to give the title compound (255 mg, 98%) as a colourless oil.

(E)-3-(3-(4-Dimethylamino-phenylsulfanyl)-phenyl)-acrylic acid ethyl ester (51a).

To a solution of (3-(4-dimethylamino-phenylsulfanyl)-phenyl)-methanol (255 mg, 0.98 mmol) and triethylamine (1.3 mL, 9.2 mmol) in dimethyl sulfoxide (5 mL) was added a solution of pyridine-sulphur trioxide (469 mg, 2.95 mmol) in dimethyl sulfoxide (5 mL). The mixture was stirred for 1 hour at room temperature and water (20 mL) and ethyl acetate (40 mL) were added. The organic layer was washed with water (3×10 mL) and brine (20 mL), dried over anhydrous MgSO$_4$, filtered and concentrated under reduced pressure to give a colourless oil. This oil was dissolved in dichloromethane (10 mL) and (triphenylphosphoranylidene)-acetic acid ethyl ester (700 mg, 2.0 mmol) was added. The mixture was stirred at reflux for 3 hours and concentrated under reduced pressure. The residue was purified by flash chromatography (20:80:1 ethyl acetate:40-60° C. petroleum ether: triethylamine) to give the title compound as a colourless oil (240 mg, 74%).

(E)-3-(3-(4-Dimethylamino-phenylsulfanyl)-phenyl-N-hydroxy-acrylamide (52a).

To a solution of the (E)-3-(3-(4dimethylamino-phenylsulfanyl)-phenyl)-acrylic acid ethyl ester (327 mg, 1.0 mmol) in distilled THF (15 mL) containing 50% aqueous hydroxylamine (0.6 mL, 9.0 mmol) was added at 0° C. a solution of potassium hydroxide in methanol (1M, 1.6 mL, 1.6 mmol) in a dropwise manner. After stirring at 0° C. for 1 h, distilled water (15 mL) was added and the mixture was made neutral by dropwise addition of concentrated hydrochloric acid (10 M) at 0° C. The aqueous solution was extracted with ethyl acetate (2×20 mL) and the combined extracts were washed with brine (20 mL), dried over anhydrous MgSO$_4$, filtered and evaporated to dryness. The solid residue was recrystallised from ethanol to give the title compound (257 mg, 82%) as a yellow solid, mp 170° C. (decomp.).

Activity Assay:

The activity of the compounds as inhibitors of histone deacetylase was investigated using a modified assay based on a rapid in vitro HDAC activity assay (based on the deacetylation of an Ω-acetylated lysine (MAL)) and described by Hoffman et al. in *Nucl. Acids. Res.* 27 2057-2058 (1999).

The HDAC substrate N-(-4-methyl-7-coumarinyl)-N-α-(tert-butyloxy-carbonyl)-N-Ω abbreviated as MAL was synthesised as described in Hoffman et al (1999). HDAC inhibitors and substrate (MAL) were made up in Hepes buffer (50 mM, pH 7.4). Purified HDAC (100 μL), inhibitor or Hepes buffer (100 μl), substrate (MAL, 100 μL 5 μg/mL) and assay buffer (100 μL, tris-HCl (10 mM), NaCl (10 mM), MgCl$_2$ (15 mM), EGTA (0.1 mM), 10% (v/v) glycerol, and mercaptoethanol (0.007%)) were incubated at 37° C. The reaction was terminated with 100 μl acetonitrile, and MAL and the deacetylated produce (ML) were determined in the supernatant.

The fluorescent substrate MAL has been used in a novel assay established and validated by Dr. Joel for the determination of HDAC activity in intact cells. This assay has been used to determine whole cell HDAC activity in the presence of known or novel HDAC inhibitors, with a single time-point reaction.

1×10$^6$ CEM cells in 1 ml medium were exposed to inhibitors at 6 concentrations for 60 minutes, after which MAL at 20 μg/ml (5 μg/mL final concentration) was added for a further 30 minutes, all at 37° C. Cells were then rapidly washed at 4° C., lysed by sonication, the reaction stopped with acetonitrile, and MAL and the deacetylated product determined in the supernatant by rapid HPLC.

For assays with partially purified rat liver HDAC enzyme, substrate (5 μg/ml MAL) and inhibitor at 6 concentrations were incubated at 37° C. for 60 minutes, after which the reaction was stopped and MAL and ML determined in the supernatant.

Chromatographic separation of MAL and ML was carried out using a 15 cm Apex ODS 5 μM column with acetonitrile/distilled water (40:60), 2% trifluoracetic acid (TFA) v/v mobile phase at a flow rate of 1.2 ml/minute. MAL and ML were quantified by fluorescence detection at excitation/emission wavelengths of 330/395 nm.

The activity of each inhibitor was assessed at a minimum of 5 non-zero concentrations. MAL and ML peak heights were used to derive the percentage MAL in the mixture as the ration of MAL: MAL+ML. The percentage MAL in the absence of inhibitor (typically 22-25%) was taken as 100% HDAC activity, and the percentage HDAC activity at higher concentrations derived from (100%−% MALdrug/100−% MALnodrug×100). These data (minimum of n=4 at each concentration for each inhibitor) were fitted to a sigmoidal EMAX model (Graphpad Prism ver 2.01) to derive the $IC_{50}$ concentration for each inhibitor.

These assays have been used to investigate the activity of known and novel HDAC inhibitors. The requirement for a hydroxamic acid moiety for potent HDAC inhibition was confirmed in the activity of sodium phenylbutyrate (NAPB) (HDAC activity $IC_{50}$; rat liver HDAC 153±51 μM, CEM cells 5572±2001 μM) and its hydroxamic acid (NaPBHA) derivative (rat liver HDAC 6.2±2.0 μM, CEM cells 158±99 μM).

IC50 values for percentage viability (3-day exposure) in CEM cells for NAPB (7800±2100 μM) and NaPBHA (138±28 μM) agreed much more closely with the whole cell HDAC activity values than with rat liver enzyme values, suggesting the whole cell assay gives a much better indication of potential biological activity.

TABLE 1

| Inhibitor | HDAC inhibitory activity ($IC_{50}$) μM Liver preparation | HDAC inhibitory activity ($IC_{50}$) μM CEM cells | % viability ($IC_{50}$) μM |
|---|---|---|---|
| sodium phenylbutyrate (NaPB) | 153 ± 51 | 5572 ± 2001 | 7800 ± 2100 |
| sodium phenyl-butyrohydroxamic acid (NaPBHA) | 6.2 ± 2.0 | 158 ± 99 | 138 ± 28 |
| trichostatin | 0.016 ± 0.005 | 0.019 ± 0.003 | 0.082 ± 0.011 |
| hexa-2,4-dienic acid hydroxamide | 0.8 ± 0.7 | 47 ± 17 | ND |
| 6-benzenesulfonyl-hexa-2,4-dienoic acid hydroxamide (CM4) | 0.8 ± 0.3 | 3.3 ± 1.3 | ND |
| 6-(-4-chloro-benzenesulfinyl)-hexa-2,4-dienoic acid hydroxamide (CM5) | 0.4 ± 0.1 | 1.2 ± 0.4 | ND |

Investigation of a number of simple, unsaturated hydroxamic acids found the straight chain hexa-2,4-dienic acid hydroxamide to have good HDAC inhibitory activity (rat liver HDAC $IC_{50}$ 0.8±0.7 μM), but the HDAC inhibitory activity was substantially lower in intact cells ($IC_{50}$ 47±17 μM).

However, increased activity resulted from the novel addition of a phenyl or chlorophenyl group to the hexa-2,4-dienic acid hydroxamide backbone via a sulphur atom as represented by compounds of the present invention 6-benzenesulfonyl-hexa-2,4-dienoic acid hydroxamide (CM4) and 6-(-4-chloro-benzenesulfinyl)-hexa-2,4-dienoic acid hydroxamide (CM5).

The whole cell assay has been further modified for the determination of the HDAC inhibitory activity of specific compounds during a 24-hour incubation with CEM cells as an indicator of in vitro compound stability. TSA exhibited a greater than 90% decrease in activity between 1 and 24 hours incubation, confirming the poor stability previously reported. SAHA activity decreased by 60% over 24 hours, while the novel compounds UCL2002 and UCL2007 showed no decrease in activity over the same period.

TABLE 2

| | HDAC inhibitory activity | | |
|---|---|---|---|
| Inhibitor | Purified liver ($IC_{50}$) μM | CEM cells ($IC_{50}$) μM | % Viability ($IC_{50}$) μM |
| TSA | .007 | .019 | |
| SAHA | 0.44 | 0.33 | 1.87 |
| UCL 2002 | 0.31 | 1.58 | 1.57 |
| UCL 2007 | 0.15 | 1.28 | 2.56 |

UCL 2002 is compound 9a - 6-(4-Chlorobenzenesulfinyl)-hexa-2,4-dienoic acid hydroxyamide
UCL 2007 is compound 31a - 6-(4-Chloro-benzenesulfinyl)-hexanoic acid hydroxyamide

The invention claimed is:
1. A compound of general formula (A)

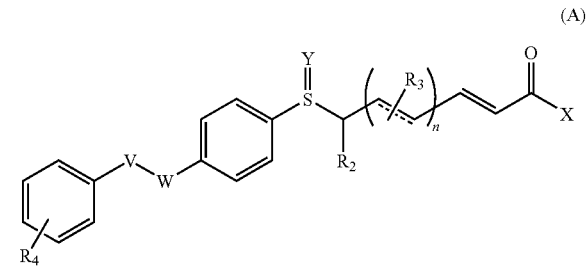

in which:

$R^2$ and $R^3$ are independently hydrogen, ($C_1$-$C_{12}$) alkyl, substituted ($C_1$-$C_{12}$) alkyl, or unsaturated ($C_2$-$C_{12}$) comprising one or more C=C bond or C≡C bond, ($C_6$ or $C_{10}$) aryl or ($C_6$ or $C_{10}$) heteroaryl, or a combination thereof to form a linked or fused ring system, or ($C_1$-$C_{10}$) alkoxy, ($C_1$-$C_{10}$) thioalkoxy, hydroxyl, ($C_1$-$C_{10}$) hydroxylalkyl, halo, ($C_1$-$C_{10}$) haloalkyl, cyano, nitro, amino, amido, ($C_1$-$C_{10}$) alkylamino, ($C_1$-$C_{10}$) alkylcarbonyloxy, ($C_1$-$C_{10}$) alkoxycarbonyl, ($C_1$-$C_{10}$) alkylcarbonyl, ($C_1$-$C_{10}$) alkylthiocarbonyl, ($C_1$-$C_{10}$) alkylsulfonylamino, aminosulfonyl, ($C_1$-$C_{10}$) alkylsulfinyl, or ($C_1$-$C_{10}$) alkylsulfonyl, in which the saturated or an unsaturated hydrocarbon chain is optionally interrupted by O, S, NR, CO, C(NR), N(R)$SO_2$, $SO_2$N(R), N(R)C (O)O, OC(O)N(R), N(R)C(O)N(R), OC(O), C(O)O, $OSO_2$, $SO_2$O, or OC(O)O, where R is independently hydrogen, ($C_1$-$C_{10}$) alkyl, ($C_1$-$C_{10}$) alkenyl, ($C_1$-$C_{10}$) alkynyl, ($C_1$-$C_{10}$) alkoxy, ($C_1$-$C_{10}$) hydroxylalkyl, hydroxyl, ($C_1$-$C_{10}$) haloalkyl, where each of the saturated or unsaturated hydrocarbon chains are optionally substituted with ($C_1$-$C_{10}$) alkyl, ($C_1$-$C_{10}$) alkenyl, ($C_1$-$C_{10}$) alkynyl, ($C_1$-$C_{10}$) alkoxy, hydroxyl, hydroxyl, ($C_1$-$C_{10}$) hydroxylalkyl, halo, ($C_1$-$C_{10}$) haloalkyl, amino, ($C_1$-$C_{10}$) alkylcarbonyloxy, ($C_1$-$C_{10}$) alkoxycarbonyl, ($C_1$-$C_{10}$) alkylcarbonyl, ($C_1$-$C_{10}$) alkylsulfonylamino, aminosulfonyl, or ($C_1$-$C_{10}$) alkylsulfonyl, or $R^2$ and $R^3$ optionally form a ($C_6$ or $C_{10}$) aryl, ($C_6$ or $C_{10}$) arylalkyl, a 6- or 10-membered ring system having one or more heteroatoms in the ring, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl linked or fused ring system, optionally containing up to 3 heteroatoms selected from oxygen, nitrogen, sulphur, and phosphorous;

$R_4$ is hydrogen, unsubstituted or substituted $C_1$-$C_{10}$ alkyl, an unsaturated hydrocarbon chain of up to ten carbon atoms comprising one or more carbon-carbon double bonds, $C_6$ or $C_{10}$ aryl, a 5 to 10 membered heterocyclic group, $C_1$-$C_{10}$ alkoxy, $C_1$-$C_{10}$ thioalkoxy, hydroxyl, halo, cyano, nitro, amino, amido, ($C_1$-$C_{10}$ alkyl)thiocarbonyl, ($C_1$-$C_{10}$ alkyl)sulfonylamino, aminosulfonyl, $C_1$-$C_{10}$ alkylsufinyl, $C_1$-$C_{10}$ alkylsulfonyl, or a saturated or unsaturated $C_3$-$C_{12}$ hydrocarbon chain interrupted by O, S, NR, CO, C(NR), C(R)SO$_2$, or OC(O)O, wherein R is as defined above and the saturated or unsaturated hydrocarbon chain is optionally substituted as defined above;

n is equal to 0, 1 or 2;

X is hydroxyl (—OH), —OR, NHR, hydroxamate (—NHOH), NHOR, NROR, NRNHR, or SR, where each R is independently hydrogen, $C_1$-$C_6$ alkyl or substituted $C_1$-$C_6$ alkyl; and Y is 0, 1 or 2 oxygen atoms;

in which V and W are as follows:
a single carbon-carbon bond;
V is CR and W is N, saturated or unsaturated;
V is N and W is CR, saturated or unsaturated;
a linkage of the form VW or WV=RRC—O or RRC—S, wherein each R is independently selected from hydrogen, ($C_1$-$C_6$) alkyl, $C_6$ aryl or heterocycle.

2. A compound of general formula (B1)

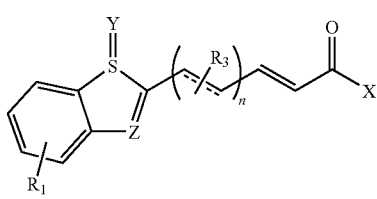

in which:
$R^1$ is ($C_6$ or $C_{10}$) aryl, ($C_6$ or $C_{10}$) arylalkyl, a 6- or 10-membered ring system having one or more heteroatoms in the ring, ($C_6$ or $C_{10}$) heteroaryl, ($C_3$-$C_8$) heterocycloalkenyl, ($C_5$-$C_8$) cycloalkene ring, $C_5$-$C_8$) cycloalkyl, ($C_5$-$C_8$) heterocycloalkyl or a combination thereof to form a linked or fused ring system, the cyclic moiety being optionally substituted with ($C_1$-$C_{10}$) alkyl, ($C_1$-$C_{10}$) alkenyl, ($C_1$-$C_{10}$) alkynyl, ($C_1$-$C_{10}$) alkoxy, ($C_1$-$C_{10}$) thioalkoxy, hydroxyl, ($C_1$-$C_{10}$) hydroxylalkyl, halo, ($C_1$-$C_{10}$) haloalkyl, amino, amido, ($C_1$-$C_{10}$) alkylamino, ($C_1$-$C_{10}$) alkylcarbonyloxy, ($C_1$-$C_{10}$) alkoxycarbonyl, ($C_1$-$C_{10}$)alkylcarbonyl, ($C_1$-$C_{10}$) alkylthiocarbonyl, ($C_1$-$C_{10}$) alkylsulfonylamino, aminosulfonyl, ($C_1$-$C_{10}$) alkylsulfinyl, or ($C_1$-$C_{10}$) alkylsulfonyl, $R^3$ is hydrogen, ($C_1$-$C_{12}$) alkyl, substituted ($C_1$-$C_{12}$) alkyl, or unsaturated ($C_2$-$C_{12}$) comprising one or more C=C bond or C≡C bond, ($C_6$ or $C_{10}$) aryl or ($C_6$ or $C_{10}$) heteroaryl, or a combination thereof to form a linked or fused ring system, or ($C_1$-$C_{10}$) alkoxy, ($C_1$-$C_{10}$) thioalkoxy, hydroxyl, ($C_1$-$C_{10}$) hydroxylalkyl, halo, ($C_1$-$C_{10}$) haloalkyl, cyano, nitro, amino, amido, ($C_1$-$C_{10}$) alkylamino, ($C_1$-$C_{10}$) alkylcarbonyloxy, ($C_1$-$C_{10}$) alkoxycarbonyl, ($C_1$-$C_{10}$) alkylcarbonyl, ($C_1$-$C_{10}$) alkylthiocarbonyl, ($C_1$-$C_{10}$) alkylsulfonylamino, aminosulfonyl, ($C_1$-$C_{10}$) alkylsulfinyl, or ($C_1$-$C_{10}$) alkylsulfonyl, in which the saturated or an unsaturated hydrocarbon chain is optionally interrupted by O, S, NR, CO, C(NR), N(R)SO$_2$, SO$_2$N(R), N(R)C(O)O, OC(O)N(R), N(R)C(O)N(R), OC(O), C(O)O, OSO$_2$, SO$_2$O, or OC(O)O, where R is independently hydrogen, ($C_1$-$C_{10}$) alkyl, ($C_1$-$C_{10}$) alkenyl, ($C_1$-$C_{10}$) alkynyl, ($C_1$-$C_{10}$) alkoxy, ($C_1$-$C_{10}$) hydroxylalkyl, hydroxyl, ($C_1$-$C_{10}$) halolalkyl, where each of the saturated or unsaturated hydrocarbon chains are optionally substituted with ($C_1$-$C_{10}$)alkyl, ($C_1$-$C_{10}$) alkenyl, ($C_1$-$C_{10}$) alkynyl, ($C_1$-$C_{10}$) alkoxy, hydroxyl, hydroxyl, ($C_1$-$C_{10}$) hydroxylalkyl, halo, ($C_1$-$C_{10}$) haloalkyl, amino, ($C_1$-$C_{10}$) alkylcarbonyloxy, ($C_1$-$C_{10}$) alkoxycarbonyl, ($C_1$-$C_{10}$) alkylcarbonyl, ($C_1$-$C_{10}$) alkylsulfonylamino, aminosulfonyl, or ($C_1$-$C_{10}$) alkylsulfonyl, n is equal to 0, 1 or 2;

X is hydroxyl (—OH), —OR, NHR, hydroxamate (—NHOH), NHOR, NROR, NRNHR, or SR, where each R is independently hydrogen, $C_1$-$C_6$ alkyl or substituted $C_1$-$C_6$ alkyl; and Y is 0, 1 or 2 oxygen atoms; and Z is a one atom linkage of N, CH, or CR or a two-atom linkage of varying combinations of atoms of CH, CR, O, N, S, SO, SO$_2$, wherein R is $C_1$-$C_6$ alkyl or substituted $C_1$-$C_6$ alkyl.

3. A compound of general formula:

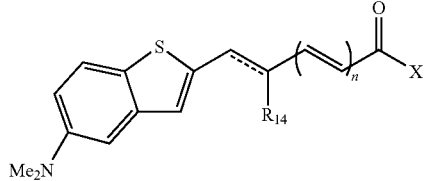

in which:
$R^{14}$ is hydrogen or ($C_1$-$C_6$)alkyl;

n is equal to 1 or 2; and

X is hydroxyl (—OH), —OR, or hydroxamate (—NHOH), where R is hydrogen, $C_1$-$C_6$ alkyl or substituted $C_1$-$C_6$ alkyl.

4. A compound of general formula (C)

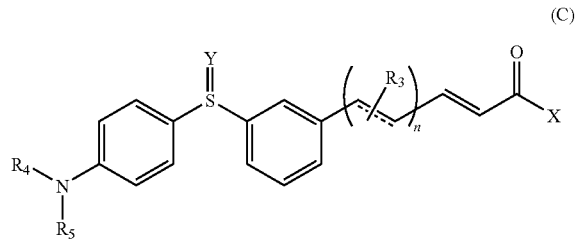

in which:
$R^3$ is hydrogen, ($C_1$-$C_{12}$) alkyl, substituted ($C_1$-$C_{12}$) alkyl, or unsaturated ($C_2$-$C_{12}$) comprising one or more C=C bond or C≡C bond, ($C_6$ or $C_{10}$) aryl or ($C_6$ or $C_{10}$) heteroaryl, or a combination thereof to form a linked or fused ring system, or ($C_1$-$C_{10}$) alkoxy, ($C_1$-$C_{10}$) thioalkoxy, hydroxyl, (C₁-C₁₀) hydroxylalkyl, halo, (C₁-C₁₀) haloalkyl, cyano, nitro, amino, amido, (C₁-C₁₀) alkylamino, (C₁-C₁₀) alkylcarbonyloxy, (C₁-C₁₀) alkoxycarbonyl, (C₁-C₁₀) alkylcarbonyl, (C₁-C₁₀) alkylthiocarbonyl, (C₁-C₁₀) alkylsulfonylamino, aminosulfonyl, (C₁-C₁₀) alkylsulfinyl, or (C₁-C₁₀) alkylsulfonyl, in which the saturated or an unsaturated hydrocarbon chain is optionally interrupted by O, S, NR, CO, C(NR), N(R)SO₂, SO₂N(R), N(R)C(O)O, OC(O)N(R), N(R)C(O)N(R), OC(O), C(O)O, OSO₂, SO₂O, or OC(O)O, where R is independently hydrogen, (C₁-C₁₀) alkyl, (C₁-C₁₀) alkenyl, (C₁-C₁₀) alkynyl, (C₁-C₁₀) alkoxy, (C₁-C₁₀) hydroxylalkyl, hydroxyl, (C₁-C₁₀) halolalkyl, where each of the saturated or unsaturated hydrocarbon chains are optionally substituted with (C₁-C₁₀) alkyl, (C₁-C₁₀) alkenyl, (C₁-C₁₀) alkynyl, (C₁-C₁₀) alkoxy, hydroxyl, hydroxyl, (C₁-C₁₀) hydroxylalkyl, halo, (C₁-C₁₀) haloalkyl, amino, (C₁-C₁₀) alkylcarbonyloxy, (C₁-C₁₀) alkoxycarbonyl, (C₁-C₁₀) alkylcarbonyl, (C₁-C₁₀) alkylsulfonylamino, aminosulfonyl, or (C₁-C₁₀) alkylsulfonyl;

n is equal to 0, 1 or 2;

X is hydroxyl (—OH), —OR, NHR, hydroxamate (—NHOH), NHOR, NROR, NRNHR, or SR, where each R is independently hydrogen, $C_1$-$C_6$ alkyl or substituted $C_1$-$C_6$ alkyl;

Y is 0, 1 or 2 oxygen atoms; and $R^4$ and $R^5$ are each independently hydrogen, unsubstituted or substituted $C_1$-$C_{10}$ alkyl, an unsaturated hydrocarbon chain of up to ten carbon atoms comprising one or more carbon-carbon double bonds, $C_6$ or $C_{10}$ aryl, a 5-to 10-membered heterocyclic group, $C_1$-$C_{10}$ alkoxy, $C_1$-$C_{10}$ thioalkoxy, hydroxyl, halo, cyano, nitro, amino, amido, ($C_1$-$C_{10}$ alkyl)carbonyloxy, ($C_1$-$C_{10}$ alkoxy)carbonyl, ($C_1$-$C_{10}$ alkyl)carbonyl, ($C_1$-$C_{10}$ alkyl)thiocarbonyl, ($C_1$-$C_{10}$ alkyl)suflonylamino, aminosulfonyl, $C_1$-$C_{10}$ a alkylsulfinyl, $C_1$-$C_{10}$ alkylsulfonyl, or a saturated or unsaturated $C_3$-$C_{12}$ hydrocarbon chain interrupted by O, S, NR, CO, C(NR), N(R)SO₂, SO₂N(R), N(R)C(O)O, OC(O)N(R), N(R)C(O)N(R), OC(O), C(O)O, OSO₂, SO₂O or OC(O)O, where R is as defined above and the saturated or unsaturated hydrocarbon chain is optionally substituted as defined above.

5. A compound as claimed in claim 1, in which $R^2$ and $R^3$ are both Hydrogen.

6. A compound as claimed in claim 1, in which $R^2$ is methyl (CH₃) and $R^3$ Hydrogen.

7. A compound as claimed in claim 1, in which $R^2$ is Hydrogen and $R^3$ is methyl (CH₃).

8. A compound as claimed in claim 1, in which $R^2$ and $R^3$ are both methyl (CH₃).

9. A compound as claimed in claim 1, in which X is —OH, —OC₂H₅, —OCH₃, or NHOH.

10. A compound as claimed in claim 1, in which Y is represented by one or two oxygen atoms.

11. A compound of general formula (Ia)

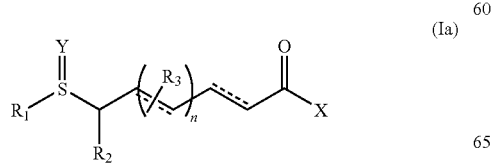

(Ia)

wherein:
$R^2$ and $R^3$ are both Hydrogen (H);
Y is two oxygen atoms;
n is 1;
$R^1$ is

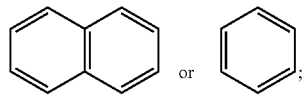

and
X is —OH, —CH₃, —OC₂H₅ or NHOH.

12. A compound of general formula (B)

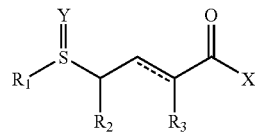

(B)

wherein:
$R^2$ and $R^3$ are both methyl (CH₃);
Y is zero oxygen atoms;
R₁ is

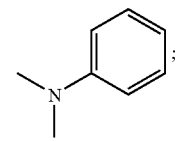

and
X is —OCH₃, —OC₂H₅ or —OH.

13. A compound which is:
6-(4-Dimethylamino-phenylsulfanyl)-hexa-2,4-dienoic acid methyl ester (6d),
6-(4-Methoxy-phenylsulfanyl)-hexa-2,4-dienoic acid methyl ester (6e),
6-(4-Chloro-phenylsulfanyl)-hexa-2,4-dienoic acid hydroxyamide (7b),
6-(4-Dimethylamino-phenylsulfanyl)-hexa-2,4-dienoic acid hydroxyamide (7c),
6-(4-Chloro-benzenesulfinyl)-hexa-2,4-dienoic acid methyl ester (8c),
6-(4-Methoxy-benzenesulfinyl)-hexa-2,4-dienoic acid methyl ester (8c),
6-Benzenesulfinyl-hexa-2,4-dienoic acid (8d),
6-(4-Chloro-benzenesulfinyl)-hexa-2,4-dienoic acid hydroxyamide (9a),
6(4-Methoxy-benzenesulfinyl)-hexa-2,4-dienoic acid hydroxyamide (9b),
6-Benzenesulfonyl-hexa-2,4-dienoic acid (10a),
6-Benzenesulfonyl-hexa-2,4-dienoic acid methyl ester (10b),
6-Benzenesulfonyl-hexa-2,4-dienoic acid hydroxyamide (11a),
6-(Naphthalen-2-ylsulfanyl)-hexa-2,4-dienoic acid methyl ester (13b),
6-(Naphthalen-2-ylsulfanyl)-hexa-2,4-dienoic acid hydroxyamide (14a), 4-(4-Dimethylamino-phenylsulfanyl)-2-methyl-pent-2-dienoic acid methyl ester (21b), 6-(4-Dimethylamino-phenylsulfanyl)-4-methyl-hepta-2,4-dienoic acid ethyl ester (24c), 6-(4-Dimethylamino-phenylsulfanyl)-4-methyl-hepta-2,4-dienoic acid hydroxyamide (25c)

6-(4-Chloro-phenylsulfanyl)-hexanoic acid methyl ester (28b), 7-(4-Chloro-phenylsulfanyl)-heptanoic acid ethyl ester (28c), 6-(4-Dimethylamino-phenylsulfanyl)-hexanoic acid methyl ester (28e), 6-(4-((4-Chlorobenzyl)-methylamino)-phenylsulfanyl)-hexanoic acid methyl ester (28f), 6-(4-(4-Chlorobenzenesulfonylamino)-phenylsulfanyl)-hexanoic acid methyl ester (28g), 6-(4-Bromo-phenylylsulfanyl)-hexanoic acid methyl ester (28h), 6-(4'-Chloro-biphenyl-4-ylsulfanyl)-hexanoic acid methyl ester (28i), 6-(4-Chloro-phenylsulfanyl)-hexanoic acid hydroxyamide (29b), 6-(4-Dimethylamino-phenylsulfanyl)-hexanoic acid hydroxyamide (29c), 6-(4-(4-Chlorobenzenesulfonylamino)-phenylsulfanyl)-hexanoic acid hydroxamide (29g), 6-(4'-Chloro-biphenyl-4-ylsulfanyl)-hexanoic acid hydroxamide (29 i), 6-(4-Chloro-benzenesulfinyl)-hexanoic acid methyl ester (30b), 7-(4-Chloro-benzenesulfinyl)-heptanoic acid ethyl ester (30c), 6-(4-Dimethylamino-benzenesulfinyl)-hexanoic acid methyl ester (30e), 6-(4-((4-Chlorobenzyl)-methylamino)-benzenesulfinyl)-hexanoic acid methyl ester (30f), 6-(4'-Chloro-biphenyl-4-ylsulfinyl)-hexanoic acid methyl ester (30i), 6-(4-Chloro-benzenesulfinyl)-hexanoic acid hydroxyamide (31a), 7-(4-Chloro-benzenesulfinyl)-heptanoic acid hydroxyamide (31c), 6-(4-Dimethylamino-benzenesulfinyl)-hexanoic acid hydroxyamide (31e), 6-(4-((4-Chlorobenzyl)-methylamino)-benzenesulfinyl)-hexanoic acid hydroxamide (31f)

6-(4'-Chloro-biphenyl-4-sulfinyl)-hexanoic acid hydroxyamide (31i), (2E,4E)-5 -(5-Dimethylamino-benzo[b]thiophen-2-yl)-penta-2,4-dienoic acid ethyl ester (41a), (2E,4E)-5-(5-Dimethylaminobenzo[b]thiophen-2-yl)-penta-2,4dienoic acid hydroxamide (42a), (E)-3-(3-(4-Dimethylamino-phenylsulfanyl)-phenyl)-acrylic acid ethyl ester (51 a), or (E)-3-(3-(4-Dimethylamino-phenylsulfanyl)-phenyl)-N-hydroxy-acrylamide (52a).

14. A pharmaceutical composition comprising a compound of claims 1 to 10, or 11 to 13, and optionally a pharmaceutically acceptable adjuvant and/or diluent.

15. A method of inhibiting HDAC activity in an individual comprising administering to said individual a therapeutically effective amount of a compound of general formula (I):

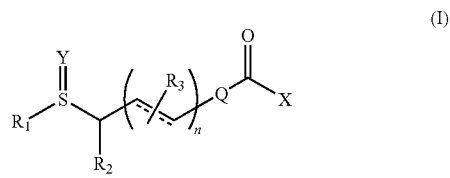

in which:

$R^1$ is ($C_6$ or $C_{10}$) aryl, ($C_6$ or $C_{10}$) arylalkyl, a 6- or 10-membered ring system having one or more heteroatoms in the ring, ($C_6$ or $C_{10}$) heteroaryl, $C_3$-$C_8$ heterocycloalkenyl, ($C_5$-$C_8$) cycloalkene ring, ($C_5$-$C_8$) cycloalkyl, ($C_5$-$C_8$) heterocycloalkyl or a combination thereof to form a linked or fused ring system, the cyclic moiety being optionally substituted with ($C_1$-$C_{10}$) alkyl, ($C_1$-$C_{10}$) alkenyl, ($C_1$-$C_{10}$) alkynyl, ($C_1$-$C_{10}$) alkoxy, ($C_1$-$C_{10}$) thioalkoxy, hydroxyl, ($C_1$-$C_{10}$) hydroxylalkyl, halo, ($C_1$-$C_{10}$) haloalkyl, amino, amido, ($C_1$-$C_{10}$) alkylamino, ($C_1$-$C_{10}$) alkylcarbonyloxy, ($C_1$-$C_{10}$) alkoxycarbonyl, ($C_1$-$C_{10}$) alkylcarbonyl, ($C_1$-$C_{10}$) alkylthiocarbonyl, ($C_1$-$C_{10}$) alkylsulfonylamino, aminosulfonyl, ($C_1$-$C_{10}$) alkylsulfinyl, or ($C_1$-$C_{10}$) alkylsulfonyl, $R^2$ and $R^3$ are each independently hydrogen, ($C_1$-$C_{12}$) alkyl, unsaturated ($C_2$-$C_{12}$) comprising one or more C=C bond or C≡C bond, ($C_1$-$C_{10}$) alkoxy, ($C_1$-$C_{10}$) thioalkoxy, hydroxyl, ($C_1$-$C_{10}$) hydroxylalkyl, halo, or ($C_1$-$C_{10}$) haloalkyl; or $R^2$ and $R^3$ optionally form a ($C_6$ or $C_{10}$) aryl, ($C_6$ or $C_{10}$) arylalkyl, a 6- or 10-membered ring system having one or more heteroatoms in the ring, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl linked or fused ring system, optionally containing up to 3 heteroatoms selected from oxygen, nitrogen, sulphur, and phosphorous; or $R^1$ and $R^2$ optionally form a ($C_6$ or $C_{10}$) aryl, ($C_6$ or $C_{10}$) arylalkyl, ($C_6$ or $C_{10}$) heteroaryl, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl linked or fused ring system, optionally the ring formed is further substituted with a group $R^1$ as defined above, or the ring formed is fused to a further $C_6$ aryl group which is optionally substituted with a group $R^1$ as defined above, or a group $R^1R^2N$, with $R^1$ and $R^2$ as defined above;

n is equal to 0, 1 or 2;

X is hydroxyl (—OH), —OR, NHR, hydroxamate (—NHOH), NHOR, NROR, NRNHR, or SR, wherein each R is independently hydrogen, $C_1$-$C_6$ alkyl or substituted $C_1$-$C_6$ alkyl;

Y is 0, 1 or 2 oxygen atoms;

Q represents

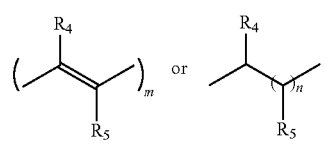

wherein:
  m is an integer from 1 to 4;
  n is an integer from 1 to 8; and
  R⁴ and R⁵ each independently represent hydrogen, or unsubstituted or substituted ($C_1$-$C_{10}$) alkyl;
or a pharmaceutically acceptable salt thereof.

16. A compound of claim 3, wherein:
  X is NHOH, OH, NROR, or CRROH; and
  Z is CR or N.

17. The method of claim 15, wherein:
  $R^1$ is ($C_6$ or $C_{10}$) aryl, optionally substituted by ($C_1$-$C_{10}$) alkoxy, halo or ($C_1$-$C_{10}$) alkylamino;
  $R^2$ and $R^3$ are each independently hydrogen or methyl, or $R^2$ and $R^3$ optionally form a $C_6$ aryl;
  n is equal to 0, 1 or 2;
  X is hydroxyl (—OH), —OR, NHR, hydroxamate (—NHOH), NHOR, NROR, NRNHR, or SR, wherein each R is independently selected from hydrogen, $C_1$-$C_6$ alkyl or substituted $C_1$-$C_6$ alkyl;
  Y is 0, 1, or 2 oxygen atoms;
  Q represents

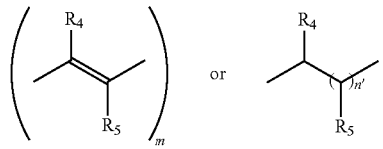

wherein:
  m is an integer from 1 to 4;
  n' is an integer from 1 to 8; and
  R⁴ and R⁵ each independently represent hydrogen or methyl.

18. The method of claim 15, wherein said compound of general formula (I) is:
  6-Phenylsulfanyl-hexa-2,4-dienoic acid (6a),
  6-(4-Chloro-phenylsulfanyl)-hexa-2,4-dienoic acid methyl ester (6b), or
  6-Phenylsulfanyl-hexa-2,4-dienoic acid methyl ester (6c).

19. A method of stimulating hematopoietic cells ex vivo, comprising administering an effective amount of a compound of general formula (I).

20. A compound of general formula (Ib)

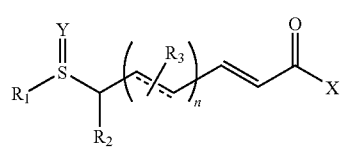

wherein:
  $R^1$ is ($C_6$ or $C_{10}$) aryl, ($C_6$ or $C_{10}$) arylalkyl, a 6- or 10-membered ring system having one or more heteroatoms in the ring, ($C_6$ or $C_{10}$) heteroaryl, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl or a combination thereof to form a linked or fused ring system, the cyclic moiety being optionally substituted with ($C_1$-$C_{10}$) alkyl, ($C_1$-$C_{10}$) alkenyl, ($C_1$-$C_{10}$) alkynyl, ($C_1$-$C_{10}$) alkoxy, ($C_1$-$C_{10}$) thioalkoxy, hydroxyl, ($C_1$-$C_{10}$) hydroxylalkyl, halo, ($C_1$-$C_{10}$) haloalkyl, amino, amido, ($C_1$-$C_{10}$) alkylamino, ($C_1$-$C_{10}$) alkylcarbonyloxy, ($C_1$-$C_{10}$) alkoxycarbonyl, ($C_1$-$C_{10}$) alkylcarbonyl, ($C_1$-$C_{10}$) alkylthiocarbonyl, ($C_1$-$C_{10}$) alkylsulfonylamino, aminosulfonyl, ($C_1$-$C_{10}$) alkylsulfinyl, or ($C_1$-$C_{10}$) alkylsulfonyl;
  $R^2$ and $R^3$ are each independently hydrogen or methyl, or $R^2$ and $R^3$ optionally form a ($C_6$ or $C_{10}$) aryl;
  n is 0, 1 or 2;
  X is hydroxamate (—NHOH); and
  Y is 0, 1 or 2 oxygen atoms;
or a pharmaceutically acceptable salt thereof.

21. The method of claim 15, wherein the compound of formula (I) has a structure of general formula (Ia):

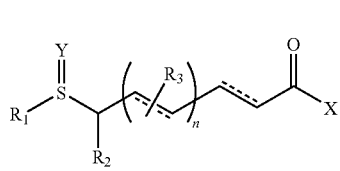

wherein:
  $R^1$ is ($C_6$ or $C_{10}$) aryl, ($C_6$ or $C_{10}$) arylalkyl, a 6- or 10-membered ring system having one or more heteroatoms in the ring, ($C_6$ or $C_{10}$) heteroaryl, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl or a combination thereof to form a linked or fused ring system, the cyclic moiety being optionally substituted with ($C_1$-$C_{10}$) alkyl, ($C_1$-$C_{10}$) alkenyl, ($C_1$-$C_{10}$) alkynyl, ($C_1$-$C_{10}$) alkoxy, ($C_1$-$C_{10}$) thioalkoxy, hydroxyl, ($C_1$-$C_{10}$) hydroxylalkyl, halo, ($C_1$-$C_{10}$) haloalkyl, amino, amido, ($C_1$-$C_{10}$) alkylamino, ($C_1$-$C_{10}$) alkylcarbonyloxy, ($C_1$-$C_{10}$) alkoxycarbonyl, ($C_1$-$C_{10}$) alkylcarbonyl, ($C_1$-$C_{10}$) alkylthiocarbonyl, ($C_1$-$C_{10}$) alkylsulfonylamino, aminosulfonyl, ($C_1$-$C_{10}$) alkylsulfinyl, or ($C_1$-$C_{10}$) alkylsulfonyl;
  $R^2$ and $R^3$ are each independently hydrogen, ($C_1$-$C_{12}$) alkyl, unsaturated ($C_2$-$C_{12}$) comprising one or more C═C bond or C≡C bond, ($C_1$-$C_{10}$) alkoxy, ($C_1$-$C_{10}$) thioalkoxy, hydroxyl, ($C_1$-$C_{10}$) hydroxylalkyl, halo, or ($C_1$-$C_{10}$) haloalkyl; or
  $R^2$ and $R^3$ optionally form a ($C_6$ or $C_{10}$) aryl, ($C_6$ or $C_{10}$) arylalkyl, a 6- or 10-membered ring system having one or more heteroatoms in the ring, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl linked or fused ring system, optionally containing up to 3 heteroatoms, e.g. oxygen, nitrogen, sulphur or phosphorous; or
  $R^1$ and $R^2$ optionally form a ($C_6$ or $C_{10}$) aryl, ($C_6$ or $C_{10}$) arylalkyl, ($C_6$ or $C_{10}$) heteroaryl, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl linked or fused ring system, optionally the ring fanned is further substituted with a group $R^1$ as defined above, or the ring formed is fused to a further $C_6$ aryl group which is optionally substituted with a group $R^1$ as defined above, or a group $R^1R^2N$, with $R^1$ and $R^2$ as defined above;
  n is 0, 1 or 2;
  X is hydroxyl (—OH), —OR, NHR, hydroxamate (—NHOH), NHOR, NROR, NRNHR, or SR, wherein each R is independently hydrogen, $C_1$-$C_6$ alkyl or substituted $C_1$-$C_6$ alkyl; and
  Y is 0, 1 or 2 oxygen atoms;
or a pharmaceutically acceptable salt thereof.

22. The compound of claim 20, in which $R^2$ and $R^3$ are both Hydrogen (H), Y is equal to zero oxygen atoms, n is equal to 1, and $R^1$ is one of

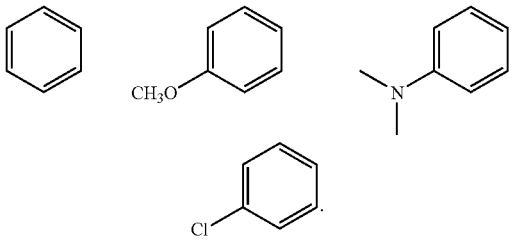

23. The compound of claim 20, wherein the compound is 6-(4-chloro-phenylsulfanyl)-hexa-2,4-dienoic acid hydroxamide (7b).

24. The method of claim 21, in which $R^2$ and $R^3$ are both Hydrogen; $R^2$ is methyl ($CH_3$) and $R^3$ is Hydrogen; $R^2$ Hydrogen and $R^3$ is methyl ($CH_3$); or $R^2$ and $R^3$ are both methyl ($CH_3$).

25. The method of claim 21, in which $R^1$ is ($C_6$ or $C_{10}$) aryl, optionally substituted by halo, ($C_1$-$C_{10}$) alkoxy or ($C_1$-$C_{10}$) alkylamino.

26. The method of claim 25 in which $R^1$ is ($C_6$ or $C_{10}$) aryl, optionally substituted by chlorine, methoxy or dimethylamino.

27. The method of claim 21, in which X is —OH, —$OC_2H_5$, —$OCH_3$, or NHOH.

28. The method of claim 21, in which $R^2$ and $R^3$ are both Hydrogen (H), Y is equal to zero oxygen atoms, and n is equal to 1, $R^1$ is one of

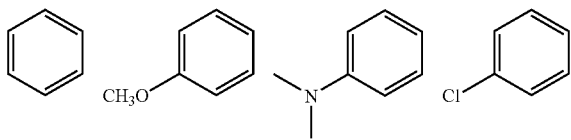

and X is one of —OH, —$OCH_3$, —$OC_2H_5$ or NHOH.

29. The method of claim 21, in which $R^2$ and $R^3$ are both Hydrogen (H), Y is equal to one oxygen atom, and n is equal to 1, $R^1$ is one of

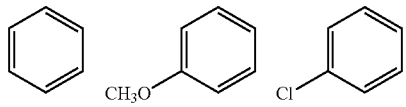

and X is one of —OH, —$OCH_3$, —$OC_2H_5$ or NHOH.

30. The method of claim 21, in which $R^2$ and $R^3$ are both Hydrogen (H), Y is equal to two oxygen atoms, n is equal to 1, $R^1$ is one of

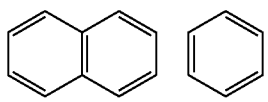

and X is one of —OH, —$CH_3$, —$OC_2H_5$ or NHOH.

31. The method of claim 15, wherein said compound of general formula (I) is:
6-(4-Dimethylamino-phenylsulfanyl)-hexa-2,4-dienoic acid methyl ester (6d);
6-(4-Methoxy-phenylsulfanyl)-hexa-2,4-dienoic acid methyl ester (6e);
6-(4-Chloro-phenylsulfanyl)-hexa-2,4-dienoic acid hydroxyamide (7b);
6-(4-Dimethylamino-phenylsulfanyl)-hexa-2,4-dienoic acid hydroxyamide (7c);
6-Phenylsulfinyl-hexa-2,4-dienoic acid methyl ester (8a);
6-(4-Chloro-benzenesulfinyl)-hexa-2,4-dienoic acid methyl ester (8b);
6-(4-Methoxy-benzetiesulfinyl)-hexa-2,4-dienoic acid methyl ester (8c);
6-Benzenesulfinyl-hexa-2,4-dienoic acid (8d);
6-(4-Chloro-benzenesulfinyl)-hexa-2,4-dienoic acid hydroxyamide (9a);
6-(4-Methoxy-benzenesulfinyl)-hexa-2,4-dienoic acid hydroxyamide (9b);
6-Benzenesulfonyl-hexa-2,4-dienoic acid (10a);
6-Benzenesulfonyl-hexa-2,4-dienoic acid methyl ester (10b);
6-Benzenesulfonyl-hexa-2,4-dienoic acid hydroxyamide (11a);
6-(Naphthalen-2-ylsulfanyl)-hexa-2,4-dienoic acid methyl ester (13b);
6-(Naphthalen-2-ylsulfanyl)-hexa-2,4-dienoic acid hydroxyamide (14a);
4-(4-Dimethylamino-phenylsulfanyl)-2-methyl-pent-2-dienoic acid methyl ester (21 b);
6-(4-Dimethylamino-phenylsulfanyl)-4-methyl-hepta-2,4-dienoic acid ethyl ester (24c);
6-(4-Dimethylamino-phenylsulfanyl)-4-methyl-hepta-2,4-dienoic acid hydroxyamide (25c);
6-(4-Chloro-phenylsulfanyl)-hexanoic acid methyl ester (28b);
7-(4-Chloro-phenylsulfanyl)-heptanoic acid ethyl ester (28c);
6-(4-Amino-phenylsulfanyl)-hexanoic acid methyl ester (28d);
6-(4-Dimethylamino-phenylsulfanyl)-hexanoic add methyl ester (28e);
6-(4-((4-Chlorobenzyl)-methylamino)-phenylsulfanyl)-hexanoic acid methyl ester (28f);
6-(4-(4-Chlorobenzenesulfonylamino)-phenylsulfanyl)-hexanoic acid methyl ester (28g);
6-(4-Bromo-phenylylsulfanyl)-hexanoic acid methyl ester (28h);
6-(4'-Chloro-biphenyl-4-ylsulfanyl)-hexanoic acid methyl ester (28i);
6-(4-Chloro-phenylsulfanyl)-hexanoic acid hydroxyamide (29b);
6-(4-Dimethylamino-phenylsulfanyl)-hexanoic acid hydroxamide (29c);
6-(4-(4-Chlorobenzenesulfonylamino)-phenylsulfanyl)-hexanoic acid hydroxamide (29g);
6-(4'-Chloro-biphenyl-4-ylsulfanyl)-hexanoic acid hydroxamide (29i);
6-(4-Chloro-benzenesulfinyl)-hexanoic acid methyl ester (30b);
7-(4-Chloro-benzenesulfinyl)-heptanoic acid ethyl ester (30c);
6-(4-Dimethylamino-benzenesulfinyl)-hexanoic acid methyl ester (30e);
6-(4-((4-Chlorobenzyl)-methylamino)-benzenesulfinyl)-hexanoic acid methyl ester (30f;

6-(4'-Chloro-biphenyl-4-ylsulfinyl)-hexanoic acid methyl ester (30i);

6-(4-Chloro-benzenesulfinyl)-hexanoic acid hydroxyamide (31a);

7-(4-Chloro-benzenesulfinyl)-heptanoic acid hydroxyamide (31c);

6-(4-Dimethylamino-benzenesulfinyl)-hexanoic acid hydroxyamide (31e);

6-(4-((4-Chlorobenzyl)-methylamino)-benzenesulfinyl)-hexanoic acid hydroxamide (31f);

6-(4'-Chloro-biphenyl-4-sulfinyl)-hexanoic acid hydroxyamide (31i);

(2E, 4E)-5-(5-Dimethylamino-benzo[b]thiophen-2-yl)-penta-2,4-dienoic acid ethyl ester (41a);

(2E,4E)-5-(5-Dimethylaminobenzo[b]thiophen-2-yl)-penta-2,4-dienoic acid hydroxamide (42a);

(E)-3-(3-(4-Dimethylamino-phenylsulfanyl)-phenyl)-acrylic acid ethyl ester (51a); or (E)-3-(3-(4-Dimethylamino-phenylsulfanyl)-phenyl)-N-hydroxy-acrylamide (52a).

32. A pharmaceutical composition comprising a compound of claims 20, 22 or 23, and optionally a pharmaceutically acceptable adjuvant and/or diluent.

* * * * *